(12) United States Patent
Beigelman et al.

(10) Patent No.: US 11,149,049 B2
(45) Date of Patent: Oct. 19, 2021

(54) SUBSTITUTED NUCLEOSIDES, NUCLEOTIDES AND ANALOGS THEREOF

(71) Applicant: JANSSEN BIOPHARMA, INC., South San Francisco, CA (US)

(72) Inventors: Leonid Beigelman, San Mateo, CA (US); Jerome Deval, El Granada, CA (US); Marija Prhavc, Encinitas, CA (US)

(73) Assignee: JANSSEN BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 16/648,405

(22) PCT Filed: Sep. 18, 2018

(86) PCT No.: PCT/IB2018/057188
§ 371 (c)(1),
(2) Date: Mar. 18, 2020

(87) PCT Pub. No.: WO2019/053696
PCT Pub. Date: Mar. 21, 2019

(65) Prior Publication Data
US 2020/0277321 A1    Sep. 3, 2020

Related U.S. Application Data

(60) Provisional application No. 62/560,110, filed on Sep. 18, 2017.

(51) Int. Cl.
| | |
|---|---|
| *C07H 7/06* | (2006.01) |
| *A61P 31/14* | (2006.01) |
| *A61P 31/16* | (2006.01) |
| *C07H 9/04* | (2006.01) |

(52) U.S. Cl.
CPC .............. *C07H 7/06* (2013.01); *A61P 31/14* (2018.01); *A61P 31/16* (2018.01); *C07H 9/04* (2013.01)

(58) Field of Classification Search
None
See application file for complete search history.

(56) References Cited

U.S. PATENT DOCUMENTS

| | | | |
|---|---|---|---|
| 5,432,272 A | 7/1995 | Benner | |
| 7,125,855 B2 | 10/2006 | Bhat | |
| 2015/0152116 A1* | 6/2015 | Mackman | A61P 31/14 536/29.2 |
| 2015/0274767 A1* | 10/2015 | Girijavallabhan | A61P 1/16 514/43 |

FOREIGN PATENT DOCUMENTS

| | | |
|---|---|---|
| WO | 2005020884 A2 | 3/2005 |
| WO | 2012012776 A1 | 1/2012 |
| WO | 2012040127 A1 | 3/2012 |
| WO | 2015/054465 A1 | 8/2016 |
| WO | 2017049060 A1 | 3/2017 |

OTHER PUBLICATIONS

International Search Report and Written Opinion dated Nov. 28, 2018 for PCT Application No. PCT/IB2018/057188.

* cited by examiner

*Primary Examiner* — Traviss C McIntosh, III
(74) *Attorney, Agent, or Firm* — Morrison & Foerster LLP

(57) ABSTRACT

Disclosed herein are compounds of the Formula (I) and pharmaceutically acceptable salts thereof: (I) where the variables in Formula (I) are described herein. Methods of synthesizing such compounds and methods of using them to treat diseases and/or conditions such as a Picornaviridae, Flaviviridae, Filoviridae, Pneumoviridae and/or Coronaviridae viral infections are also disclosed.

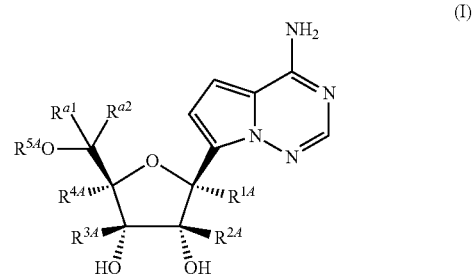

20 Claims, 8 Drawing Sheets

SUBSTITUTED NUCLEOSIDES, NUCLEOTIDES AND ANALOGS THEREOF

CROSS-REFERENCE TO RELATED APPLICATIONS

This application is a national phase entry of International Application No. PCT/IB2018/0570188, filed on Sep. 18, 2018, which claims priority to U.S. Patent Application No. 62/560,110, filed Sep. 18, 2017, each of which is incorporated herein in its entirety.

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

BACKGROUND

Field

The present application relates to the fields of chemistry, biochemistry and medicine. More particularly, disclosed herein are nucleotide analogs, pharmaceutical compositions that include one or more nucleotide analogs and methods of synthesizing the same. Also disclosed herein are methods of treating viral diseases and/or conditions with a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

The challenge of developing new antiviral compounds is complicated by the large number of different viruses and the diversity of their characteristics. Under the Hierarchical virus classification system, viruses are grouped by their shared properties according to four main characteristics: (1) nucleic acid (DNA or RNA); (2) symmetry of capsid (icosahedral, helical or complex); (3) naked or enveloped; and (4) genome architecture (positive sense or negative sense, and single stranded or double stranded). Under the Baltimore classification, viruses are grouped according to both their genome structure and method of replication: Group 1 (double-stranded DNA virus); Group II: (single stranded DNA virus); Group III (double-stranded RNA virus); Group IV (single stranded positive sense RNA virus); Group V (single stranded negative sense RNA virus); Group VI (single stranded positive sense RNA virus that replicates through a DNA intermediate); and Group VII (double stranded DNA virus that replicates through a single stranded RNA intermediate). Within the recognized groups, there are over one hundred recognized families of viruses, some of which are also classified into eight different orders (Bunyavirales, Caudovirales, Herpesvirales, Ligamenvirales, Mononegavirales, Nidovirales, Picornavirales and Tymovirales). In general, because of the differences between these recognized families, there is no expectation that an antiviral compound that is active against a virus that is classified in any particular family will also be active against viruses that are classified in one or more of the other families. For example, the viruses within the Picornaviridae, Flaviviridae, Filoviridae, Pneumoviridae and Coronaviridae families have diverse characteristics that make it very challenging to develop an antiviral that is active against viruses in two or more of the families.

The viruses within the Picornaviridae family are non-enveloped, positive sense, single-stranded, spherical RNA viruses with an icosahedral capsid. They are Group IV viruses under the Baltimore classification, in the order Picornavirales. The Picornavirus genomes are approximately 7-8 kilobases long and have an IRES (Internal Ribosomal Entry Site). These viruses are polyadenylated at the 3' end, and has a VPg protein at the 5' end in place of a cap. Genera within the Picornaviridae family include Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Rhinovirus, Salivirus, Sapelovirus, Senecavirus, Teschovirus and Tremovirus.

Enteroviruses are transmitted through the fecal-oral route and/or via aerosols of respiratory droplets, and are highly communicable. The genus of Enterovirus includes several species, including: enterovirus A, enterovirus B, enterovirus C, enterovirus D, enterovirus E, enterovirus F, enterovirus G, enterovirus Henterovirus J, rhinovirus A, rhinovirus B and rhinovirus C. Within a species of the aforementioned enteroviruses are the following serotypes: polioviruses, rhinoviruses, coxsackieviruses, echoviruses and enterovirus.

Rhinoviruses are the cause of the common cold. Rhinoviruses are named because of their transmission through the respiratory route and replication in the nose. A person can be infected with numerous rhinoviruses over their lifetime because immunity develops for each serotype. Thus, each serotype can cause a new infection.

A hepatitis A infection is the result of an infection with a Hepatitis A virus. Hepatovirus is transmitted through the fecal-oral route. Transmission can occur via person-to-person by ingestion of contaminated food or water, or through direct contact with an infectious person.

Parechovirus include human parechovirus 1 (echovirus 22), human parechovirus 2 (echovirus 23), human parechovirus 3, human parechovirus 4, human parechovirus 5 and human parechovirus 6.

The viruses with the Flaviviridae family are enveloped, positive sense, single-stranded, spherical RNA viruses with an icosahedral shaped capsid. They are Group IV viruses under the Baltimore classification, and have not been assigned to an order. These viruses are polyadenylated at the 5' end but lack a 3' polyadenylate tail. Genera within the Flaviviridae family include: Flavivirus, Pestivirus and Hepacivirus. Flaviviridae viruses are predominantly arthropod-borne, and are often transmitted via mosquitos and ticks. Effects/symptoms of a Picornaviridae viral infection depend on the species of virus, and can include, but are not limited to, fever, blisters, rash, meningitis, conjunctivitis, acute hemorrhagic conjunctivitis (AHC), sore throat, nasal congestion, runny nose, sneezing, coughing, loss of appetite, muscle aches, headache, fatigue, nausea, jaundice, encephalitis, herpangina, myocarditis, pericarditis, meningitis, Bornholm disease, myalgia, nasal congestion, muscle weakness, loss of appetite, fever, vomiting, abdominal pain, abdominal discomfort, dark urine and muscle pain.

Hepaciviruses include Hepatitis C (HCV). There are various nonstructural proteins of HCV, such as NS2, NS3, NS4, NS4A, NS4B, NS5A and NS5B. NS5B is believed to be an RNA-dependent RNA polymerase involved in the replication of HCV RNA. Flaviviruses include several encephalitis viruses (for example, Japanese Encephalitis virus (JEV), St. Louis encephalitis virus (SLEV) and tick-borne encephalitis virus (TBEV)), dengue virus 1-4 (DENV), West Nile virus (WNV), yellow fever virus (YFV), and Zika virus (ZIKV). A West Nile infection can lead to West Nile fever or severe West Nile disease (also called West Nile encephalitis or meningitis or West Nile poliomyelitis). Symptoms of West Nile fever include fever, headache, tiredness, body aches, nausea, vomiting, a skin rash (on the trunk of the body) and swollen lymph glands. Symptoms of West Nile disease include headache, high fever, neck stiffness, stupor, disorientation, coma, tremors, convulsions, muscle weakness and paralysis. Current treatment for a West Nile virus infection is supportive, and no vaccination is currently available for humans.

According to the World Health Organization (WHO), global incidence of dengue has grown dramatically in recent decades. To date, there is no treatment for a dengue virus infection. Further, recovery from an infection of one serotype of dengue virus provides only partial and temporary immunity against the other serotypes. Subsequent infection(s) with another serotypes increases the likelihood of developing severe dengue (previously known as dengue hemorrhagic fever). A dengue infection is suspected with a high fever (approx. 104° F.) accompanied by one or more of the following symptoms: severe headache, pain behind the eyes, muscle and joint pain, nausea, vomiting, swollen glands and rash.

Yellow fever is an acute viral hemorrhagic disease. As provided by the WHO, up to 50% of severely affected persons without treatment die from yellow fever. An estimated 200,000 cases of yellow fever, causing 30,000 deaths, worldwide occur each year. As with other Flaviviruses, there is no cure or specific treatment for yellow fever, and treatment with ribavirin and interferons are insufficient. Symptoms of a yellow fever infection include fever, muscle pain with prominent backache, headache, shivers, loss of appetite, nausea, vomiting, jaundice and bleeding (for example from the mouth, nose, eyes and/or stomach). Viruses within the Pestivirus genus include bovine viral diarrhea 1, bovine viral diarrhea 2, and classic swine fever virus. Viral encephalitis causes inflammation of the brain and/or meninges. Symptoms include high fever, headache, sensitivity to light, stiff neck and back, vomiting, confusion, seizures, paralysis and coma. There is no specific treatment for an encephalitis infection, such as Japanese encephalitis, St. Louis encephalitis and tick borne encephalitis. According to the Centers for Disease Control, Zika is spread mostly by the bite of an infected Aedes species mosquito (Ae. aegypti and Ae. albopictus) and can be passed from a pregnant woman to her fetus. Infection during pregnancy can cause certain birth defects. Many people infected with Zika virus will not have symptoms or will only have mild symptoms. The most common symptoms of Zika are fever, rash, joint pain, and conjunctivitis. Zika is usually mild with symptoms lasting for several days to a week. People usually do not get sick enough to go to the hospital, and they very rarely die of Zika. For this reason, many people might not realize they have been infected. Symptoms of Zika are similar to other viruses spread through mosquito bites, like dengue and chikungunya.

The viruses of the Filoviridae family are enveloped, negative sense, single-stranded, linear RNA viruses. They are Group V viruses under the Baltimore classification, in the order Mononegavirales. Three genera within the Filoviridae family are Ebolavirus, Marburgvirus and "Cuevavirus" (tentative). The five recognized species of Ebolavirus are Ebola virus (EBOV), Reston ebolavirus (REBOV), Sudan ebolavirus (SEBOV), Taï Forest ebolavirus (TAFV) and Bundibugyo ebolavirus (BEBOV). The two recognized species of Marburgvirus are Marburg virus (MARV) and Ravn virus (RAVV). Ebolavirus and Marburgvirus are highly infectious and contagious. Both viruses are transmitted by direct contact with the blood, body fluids and/or tissues of infected persons. Ebolavirus and Marburgvirus can also be transmitted by handling sick or dead infected wild animals. Ebola hemorrhagic fever (EHF) is caused by an Ebolavirus infection. Marburg virus disease (MVD) is a human disease caused by a Marburgvirus, and causes Marburgvirus hemorrhagic fever (MHF). Ebolavirus and Marburgvirus cause viral hemorrhagic fever in various primates, including humans.

Pneumoviridae is a relatively new virus family that was created by elevating the paramyxoviral subfamily Pneumovirinae. The viruses of the Pneumoviridae family are negative sense, single-stranded, RNA viruses. They are Group V viruses under the Baltimore classification, in the order Mononegavirales. Two genera within the Pneumoviridae family are Metapneumovirus and Orthopneumovirus. The two recognized species of Metapneumovirus are avian metapneumovirus (AMPV) and human metapneumovirus (HMPV). The three recognized species of Orthopneumovirus are Bovine respiratory syncytial virus (BRSV), Human respiratory syncytial virus (HRSV, including HRSV-A2, HRSV-B1 and HRSV-S2) and Murine pneumonia virus (MPV). Viruses in the Pneumoviridae family are typically transmitted through respiratory secretions and are often associated with respiratory infections.

Coronaviridae viruses are a family of enveloped, positive-stranded, single-stranded, spherical RNA viruses. They are Group IV viruses under the Baltimore classification, in the order Nidovirales. Coronaviruses are named for the crown-like spikes on their surface. The Coronaviridae family includes two sub-families, Coronavirus and Torovirus. The Coronavirus genus has a helical nucleocapsid, and Torovirus genus has a tubular nucleocapsid. Within the Coronavirus sub-family are the following genera: Alphacoronavirus, Betacoronavirus, Gammacoronavirus and Deltacoronavirus. Genera within the Torovirus sub-family are Bafinivirus and Torovirus.

Human coronaviruses usually cause mild to moderate upper-respiratory tract illnesses, like the common cold, that last for a short amount of time (although some coronaviruses can be deadly). Symptoms may include runny nose, cough, sore throat, and fever. These viruses can sometimes cause lower-respiratory tract illnesses, such as pneumonia. This is more common in people with cardiopulmonary disease or compromised immune systems, or the elderly.

Middle East respiratory syndrome coronavirus (MERS-CoV) is a member of the Betacoronavirus genus, and causes Middle East Respiratory Syndrome (MERS). MERS is an acute respiratory illness. About half of the individuals confirmed to have been infected with MERS died. There is no current treatment or vaccine for MERS.

Another member of the Betacornavirus genus is SARS coronavirus (SARS-CoV). SARS-Co-V is the virus that causes severe acute respiratory syndrome (SARS). SARS was first reported in Asia in February 2003. SARS is an airborne virus, and can spread by the inhalation of small droplets of water that an infected individuals releases into the air (for example, by coughing and/or sneezing), touching a contaminated surface and/or by being in close proximity of an infected individual (for example, cared for or lived with a person known to have SARS or having a high likelihood of direct contact with respiratory secretions and/or body fluids of a patient known to have SARS, including kissing or embracing, sharing eating or drinking utensils, close conversation (within 3 feet), physical examination, and any other direct physical contact between people).

The two genera within the Togaviridae family are Alphavirus and Rubivirus. Viruses within this family are enveloped, positive-sense, single-stranded, linear RNA viruses. To date, Rubivirus has one species, Rubella virus. Viruses classified in the Alphavirus genus include Venezuelan equine encephalitis (VEE) viruses. VEE viruses are mainly transmitted by mosquitos and cause Venezuelan equine encephalitis and encephalomyelitis. The VEE complex of viruses includes six antigenic subtypes (I-VI) divided by antigenic variants. Additionally, VEE viruses are divided into two groups, epizootic (or epidemic) and enzootic (or endemic). Within subtype I, the Venezuelan equine encephalomyelitis virus (VEEV), is divided into five antigenic variants (variants AB-F). Subtype II is known as Everglades virus, subtype III as Mucambo virus, and subtype IV as Pixuna virus. Equine species along with humans can be infected with VEE viruses. Currently, there is no vaccine available for horses or humans.

Another member of the Alphavirus genus is Chikungunya (CHIKV). Chikungunya is an arthropod-borne virus and can be transmitted to humans by mosquitoes (such as Aedes mosquitos). Currently, there are no specific treatments for Chikungunya, and no vaccine is currently available.

Other Alphaviruses are Barmah Forest virus, Mayaro virus (MAYV), O'nyong'nyong virus, Ross River virus (RRV), Semliki Forest virus, Sindbis virus (SINV), Una virus, Eastern equine encephalitis virus (EEE) and Western equine encephalomyelitis (WEE). These Alphaviruses are mainly arthropod-borne, and transmitted via mosquitos.

The lack of expectation that a newly developed nucleoside analog will be panviral, e.g., active against two or more viruses that are classified in different virus families, is based in part on the observation that panviral activity has been found for relatively few of the many known nucleoside analogs. Although panviral activity is generally considered to be desirable, the activity of such compounds against diverse viruses also raises the prospect that increased off-target effects might also be observed, leading to potential toxicity concerns that tend to slow clinical development. Thus, there remains a long-felt need for panviral nucleoside analogs, and particularly those having low toxicity.

SUMMARY

Some embodiments disclosed herein relate to a compound of Formula (I), or a pharmaceutically acceptable salt thereof. In various embodiments, compounds of Formula (I) and/or pharmaceutically acceptable salts thereof exhibit panviral activity. Such panviral activity is surprising because of the diversity of viruses against which they are active. For example, in some embodiments a compound of Formula (I), or a pharmaceutically acceptable salt thereof, exhibits activity against viruses that are in two or more different virus families. In some embodiments, a compound of Formula (I), or a pharmaceutically acceptable salt thereof exhibits activity against a virus in two of more of the Picornaviridae, Flaviviridae, Filoviridae, Pneumoviridae and/or Coronaviridae families.

In some embodiments, a compound of Formula (I), or a pharmaceutically acceptable salt thereof, has low toxicity. In some embodiments, a compound of Formula (I), or a pharmaceutically acceptable salt thereof, has both low toxicity and is panviral, unexpectedly exhibiting activity against viruses that are in two or more different virus families despite its low toxicity.

Some embodiments disclosed herein relate to a method of ameliorating and/or treating a Picornaviridae viral infection that can include administering to a subject identified as suffering from the Picornaviridae viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a Picornaviridae viral infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a Picornaviridae viral infection.

Some embodiments disclosed herein relate to a method of ameliorating and/or treating a Picornaviridae viral infection that can include contacting a cell infected with the picornavirus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for ameliorating and/or treating a Picornaviridae viral infection that can include contacting a cell infected with the picornavirus with an effective amount of said compound(s). Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for ameliorating and/or treating a Picornaviridae viral infection by contacting a cell infected with the picornavirus with an effective amount of said compound(s).

Some embodiments disclosed herein relate to a method of inhibiting replication of a Picornaviridae virus that can include contacting a cell infected with the picornavirus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a Picornaviridae virus that can include contacting a cell infected with the Picornaviridae virus with an effective amount of said compound(s). Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for inhibiting replication of a Picornaviridae virus by contacting a cell infected with the picornavirus with an effective amount of said compound(s). In some embodiments, the Picornaviridae virus can be selected from a rhinovirus, hepatitis A virus, a coxasackie virus and an enterovirus.

Some embodiments disclosed herein relate to a method of ameliorating and/or treating a Flaviviridae viral infection that can include administering to a subject identified as suffering from the Flaviviridae viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments disclosed herein relate to a method of ameliorating and/or treating a Flaviviridae viral infection that can include contacting a cell infected with the Flaviviridae virus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Still other embodiments described herein relate to using one or more compounds of Formula (I), or a pharmaceutically acceptable salt thereof, in the manufacture of a medicament for ameliorating and/or treating a Flaviviridae viral infection. Yet still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a Flaviviridae viral infection. Some embodiments disclosed herein relate to a method of inhibiting replication of a Flaviviridae virus that can include contacting a cell infected with the Flaviviridae with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a Flaviviridae virus. Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for inhibiting replication of a Flaviviridae virus. In some embodiments, the Flaviviridae virus can be selected from Hepatitis C (HCV), dengue and Zika.

Some embodiments disclosed herein relate to a method of ameliorating and/or treating a Filoviridae viral infection that can include administering to a subject identified as suffering from the Filoviridae viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments disclosed herein relate to a method of ameliorating and/or treating a Filoviridae viral infection that can include contacting a cell infected with the Filoviridae virus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Still other embodiments described herein relate to using one or more compounds of Formula (I), or a pharmaceutically acceptable salt thereof, in the manufacture of a medicament for ameliorating and/or treating a Filoviridae viral infection. Yet still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a Filoviridae viral infection. Some embodiments disclosed herein relate to a method of inhibiting replication of a Filoviridae virus that can include contacting a cell infected with the Filoviridae with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a Filoviridae virus. Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for inhibiting replication of a Filoviridae virus. In some embodiments, the Filoviridae virus can be an Ebolavirus or a Marburgvirus.

Some embodiments disclosed herein relate to a method of ameliorating and/or treating a Pneumoviridae viral infection that can include administering to a subject identified as suffering from the Pneumoviridae viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments disclosed herein relate to a method of ameliorating and/or treating a Pneumoviridae viral infection that can include contacting a cell infected with the Pneumoviridae virus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Still other embodiments described herein relate to using one or more compounds of Formula (I), or a pharmaceutically acceptable salt thereof, in the manufacture of a medicament for ameliorating and/or treating a Pneumoviridae viral infection. Yet still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a Pneumoviridae viral infection. Some embodiments disclosed herein relate to a method of inhibiting replication of a Pneumoviridae virus that can include contacting a cell infected with the Pneumoviridae with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a Pneumoviridae virus. Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for inhibiting replication of a Pneumoviridae virus. In some embodiments, the Pneumoviridae virus can be a human respiratory syncytial virus.

Some embodiments disclosed herein relate to a method of ameliorating and/or treating a Coronaviridae viral infection that can include administering to a subject identified as suffering from the Coronaviridae viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments disclosed herein relate to a method of ameliorating and/or treating a Coronaviridae viral infection that can include contacting a cell infected with the Coronaviridae virus with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Still other embodiments described herein relate to using one or more compounds of Formula (I), or a pharmaceutically acceptable salt thereof, in the manufacture of a medicament for ameliorating and/or treating a Coronaviridae viral infection. Yet still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a Coronaviridae viral infection. Some embodiments disclosed herein relate to a method of inhibiting replication of a Coronaviridae virus that can include contacting a cell infected with the Coronaviridae with an effective amount of one or more compounds described herein (for example, a compound of Formula (I), or a pharmaceutically acceptable salt thereof), or a pharmaceutical composition that includes one or more compounds described herein, or a pharmaceutically acceptable salt thereof. Other embodiments described herein relate to using one or more compounds described herein (for example, a compound of Formula (I), or a pharmaceutically acceptable salt thereof) in the manufacture of a medicament for inhibiting replication of a Coronaviridae virus. Still other embodiments described herein relate to one or more compounds described herein (for example, a compound of Formula (I), or a pharmaceutically acceptable salt thereof), or a pharmaceutical composition that includes one or more compounds described herein, or a pharmaceutically acceptable salt thereof, that can be used for inhibiting replication of a Coronaviridae virus. In some embodiments, the Coronaviridae virus can be a human α-coronavirus viral infection or a human β-coronavirus viral infection.

These and other embodiments are described in greater detail below.

DETAILED DESCRIPTION

Definitions

Figure 1:
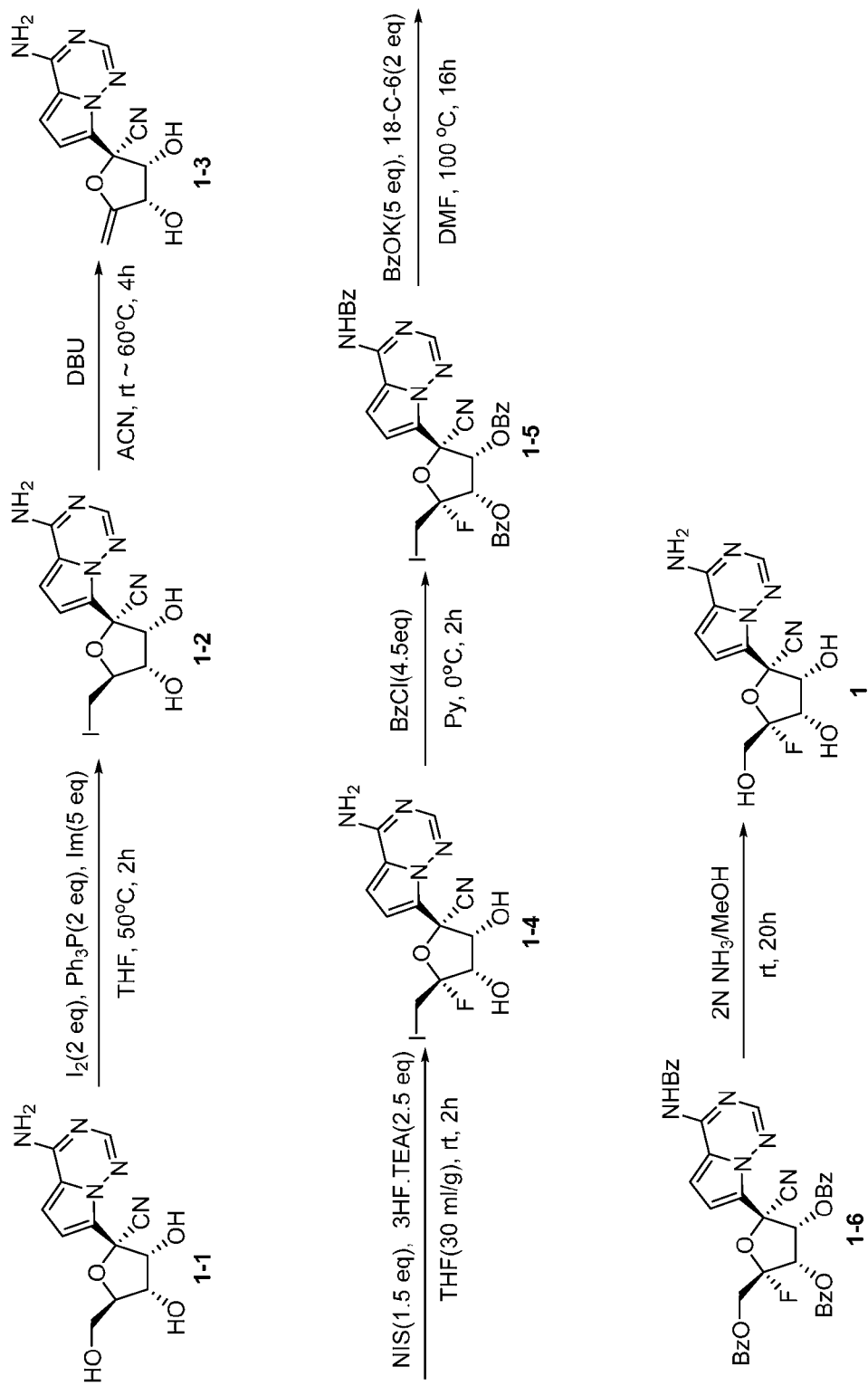
FIG. 1 illustrates a reaction scheme for making compound 1.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^A$, $R^{1A}R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, $R^{22A}$, $R^{23A}$, $R^{24A}$, $R^{25A}$, $R^{26A}$, $R^{27A}$, $R^{28A}$, $R^{29A}$, $R^{30A}$, $R^{31A}$, $R^{a1}$ and $R^{a2}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

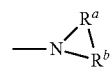

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, an asterisk ("*") used with respect to a chemical group indicates a point of attachment. For example, the asterisk in the chemical group "*—$(CR^{15A}R^{16A})_p$—O—$C_{1-24}$ alkyl" indicates the point of attachment for that chemical group to another group or molecule.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl) and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen or deuterium of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), (heteroaryl)alkyl or (heterocyclyl)alkyl is defined herein. A non-limiting list of alkoxys is methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, deuterium, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen or deuterium atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen or deuterium atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an —O-alkyl group in which one or more of the hydrogen or deuterium atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl.

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An S-sulfonamido may be substituted or unsubstituted.

An "N-sulfonamido" group refers to a "RSO$_2$N(R$_A$)—" group in which R and R$_A$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-sulfonamido may be substituted or unsubstituted.

An "O-carbamyl" group refers to a "—OC(=O)N($R_A R_B$)" group in which $R_A$ and $R_B$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-carbamyl may be substituted or unsubstituted.

An "N-carbamyl" group refers to an "ROC(=O)N($R_A$)—" group in which R and $R_A$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-carbamyl may be substituted or unsubstituted.

An "O-thiocarbamyl" group refers to a "—OC(=S)—N($R_A R_B$)" group in which $R_A$ and $R_B$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-thiocarbamyl may be substituted or unsubstituted.

A "C-amido" group refers to a "—C(=O)N($R_A R_B$)" group in which $R_A$ and $R_B$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. A C-amido may be substituted or unsubstituted.

An "N-amido" group refers to a "RC(=O)N($R_A$)—" group in which R and $R_A$ can be independently hydrogen, deuterium, alkyl, alkenyl, alkynyl, cycloalkyl, cycloalkenyl, aryl, heteroaryl, heterocyclyl, aryl(alkyl), (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the number of substituents is not specified (e.g. haloalkyl), there may be one or more substituents present. For example, "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom.

A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4$,$N^4$-ethanocytosin, $N^6$,$N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogen or deuteriums that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen or deuterium that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

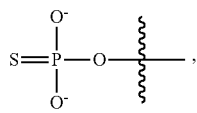

its protonated forms (for example,

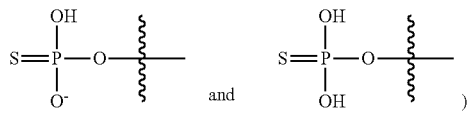

and its tautomers (such as

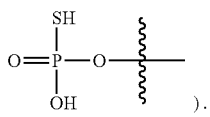

).

As used herein, the term "phosphate" is used in its ordinary sense as understood by those skilled in the art, and includes its protonated forms (for example,

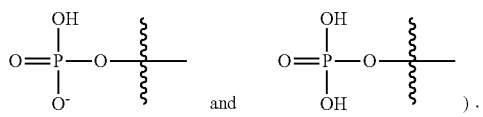

).

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of any of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may be independently of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may be independently E or Z, or a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

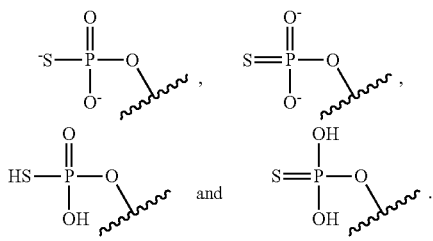

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled as needed with hydrogen (also referred to as protium, hydrogen-1 or $^1$H) or isotopes thereof. A suitable isotope of hydrogen is deuterium (also referred to as hydrogen-2 or $^2$H).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. Thus, reference herein to a compound encompasses all potential isotopic forms unless the context clearly dictates otherwise or an isotope is already explicitly specified.

It is understood that the compounds, methods and combinations described herein include crystalline forms (also known as polymorphs, which include the different crystal packing arrangements of the same elemental composition of a compound), amorphous phases, salts, solvates and hydrates. In some embodiments, the compounds described herein (including those described in methods and combinations) exist in solvated forms with pharmaceutically acceptable solvents such as water, ethanol, or the like. In other embodiments, the compounds described herein (including those described in methods and combinations) exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

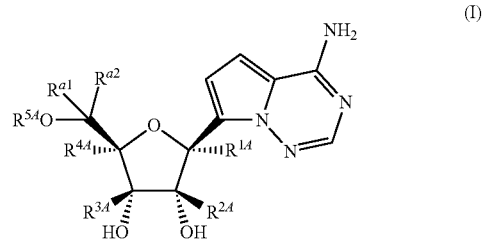

In various embodiments of compounds of the Formula (I), $R^{1A}$ can be selected from the group consisting of fluoro, cyano, azido, an unsubstituted $C_{2-4}$ alkenyl, an unsubstituted $C_{2-4}$ alkynyl, an unsubstituted $C_{1-4}$ alkoxy, an unsubstituted $C_{1-4}$ alkyl, and a substituted $C_{1-4}$ alkyl. In some embodiments, the unsubstituted $C_{1-4}$ alkoxy is methoxy. In some embodiments, the unsubstituted $C_{1-4}$ alkyl is methyl. In various embodiments, when $R^{1A}$ is a substituted $C_{1-4}$ alkyl, it is substituted with one or more substituents selected from fluoro and chloro. For example, in some embodiments $R^{1A}$ can be a substituted $C_{1-4}$ alkyl that is selected from the group consisting of —(CH$_2$)$_{1-4}$Cl, —(CH$_2$)$_{1-4}$F, and —CHF$_2$.

Non-limiting examples of substituted $C_{1-4}$ alkyl thus include chloromethyl, fluoromethyl and difluoromethyl.

In some embodiments of compounds of the Formula (I), $R^{1A}$ can be cyano. The following Formulae (Ia1) is an example of embodiments of compounds of the Formula (I) in which the variable $R^{1A}$ is cyano and the variables $R^{2A}$, $R^{3A}$, $R^{4A}$, $R^{5A}$, $R^{a1}$ and $R^{a2}$ are as described elsewhere herein.

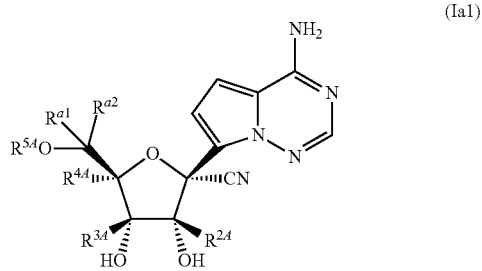

(Ia1)

For example, the following Formula (Ia2) is an example of an embodiment of compounds of the Formula (I):

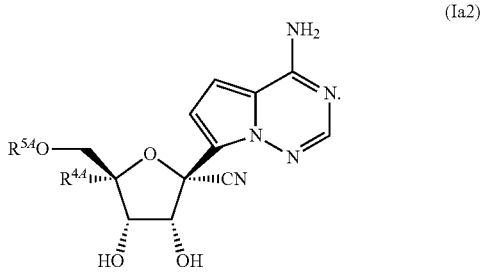

(Ia2)

In various embodiments of compounds of the Formula (I), $R^{4A}$ can be selected from the group consisting of fluoro, cyano, azido, an unsubstituted $C_{2-4}$ alkenyl, an unsubstituted $C_{2-4}$ alkynyl, an unsubstituted $C_{1-4}$ alkoxy, an unsubstituted $C_{1-4}$ alkyl, and a substituted $C_{1-4}$ alkyl, wherein said substituted $C_{1-4}$ alkyl is substituted with one or more substituents selected from fluoro and chloro. In some embodiments, $R^{4A}$ is selected from the group consisting of fluoro, cyano, azido, and an unsubstituted $C_{1-4}$ alkyl. In some embodiments, $R^{4A}$ is selected from the group consisting of fluoro, cyano, azido, and $C_{1-4}$ alkyl substituted with one or more substituents selected from fluoro and chloro. In an embodiment, $R^{4A}$ is fluoro. In another embodiment, $R^{4A}$ is cyano. In another embodiment, $R^{4A}$ is azido. In another embodiment, $R^{4A}$ is an unsubstituted $C_{1-4}$ alkyl. For example, in an embodiment, $R^{4A}$ is methyl. In various embodiments, when $R^{4A}$ is a substituted $C_{1-4}$ alkyl, it is substituted with one or more substituents selected from fluoro and chloro. For example, in some embodiments $R^{4A}$ can be a substituted $C_{1-4}$ alkyl that is selected from the group consisting of $—(CH_2)_{1-4}C_1$, $—(CH_2)_{1-4}F$ and $—CHF_2$. Non-limiting examples of substituted $C_{1-4}$ alkyl thus include chloromethyl, fluoromethyl and difluoromethyl. Thus, in an embodiment, the substituted $C_{1-4}$ alkyl is chloromethyl. In another embodiment, the substituted $C_{1-4}$ alkyl is fluoromethyl.

In various embodiments, the variables $R^{2A}$ and $R^{3A}$ of the formula (I) are each independently hydrogen or deuterium. In an embodiment, $R^{2A}$ and $R^{3A}$ are both hydrogen. In an embodiment, $R^{2A}$ and $R^{3A}$ are both deuterium. In an embodiment, one of $R^{2A}$ and $R^{3A}$ is hydrogen and the other is deuterium.

In various embodiments, the variables $R^{a1}$ and $R^{a2}$ of the formula (I) are each independently hydrogen or deuterium. In an embodiment, $R^{a1}$ and $R^{a2}$ are both hydrogen. In an embodiment, $R^{a1}$ and $R^{a2}$ are both deuterium. In an embodiment, one of $R^{a1}$ and $R^{a2}$ is hydrogen and the other is deuterium.

In some embodiments of compounds of the Formula (I), $R^{1A}$ is selected from the group consisting of fluoro, cyano, azido, an unsubstituted $C_{2-4}$ alkenyl, an unsubstituted $C_{2-4}$ alkynyl, an unsubstituted $C_{1-4}$ alkoxy, an unsubstituted $C_{1-4}$ alkyl, and a substituted $C_{1-4}$ alkyl, and $R^{4A}$ is selected from the group consisting of fluoro, cyano, azido, an unsubstituted $C_{2-4}$ alkenyl, an unsubstituted $C_{2-4}$ alkynyl, an unsubstituted $C_{1-4}$ alkoxy, an unsubstituted $C_{1-4}$ alkyl, and a substituted $C_{1-4}$ alkyl, wherein said substituted $C_{1-4}$ alkyl is substituted with one or more substituents selected from fluoro and chloro. For example, in some embodiments, $R^{1A}$ is cyano, and $R^{4A}$ is selected from the group consisting of fluoro, cyano, azido, an unsubstituted $C_{2-4}$ alkenyl, an unsubstituted $C_{2-4}$ alkynyl, chloromethyl, fluoromethyl, and difluoromethyl. In some embodiments, $R^{1A}$ is cyano, and $R^{4A}$ is fluoro. In some embodiments, $R^{1A}$ is cyano, and $R^{4A}$ is fluoromethyl. In some embodiments, $R^{1A}$ is cyano, and $R^{4A}$ is chloromethyl. In some embodiments, $R^{1A}$ is cyano, and $R^{4A}$ is azido. In some embodiments, both $R^{1A}$ and $R^{4A}$ are cyano.

In various embodiments, the variable $R^{5A}$ of the Formula (I) is selected from the group consisting of hydrogen, an optionally substituted acyl, an optionally substituted O-linked amino acid,

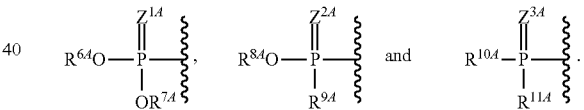

$R^{6A}$, $R^{7A}$ and $R^{8A}$ can be independently selected from absent, hydrogen, an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—$(CR^{15A}R^{16A})_p$—O—$C_{1-24}$ alkyl, an optionally substituted *—$(CR^{17A}R^{18A})_q$—O—$C_{1-24}$ alkenyl,

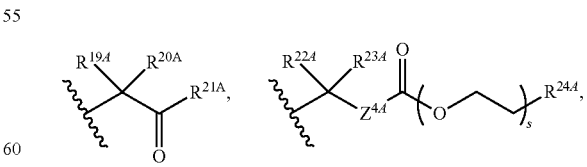

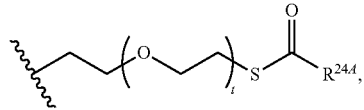

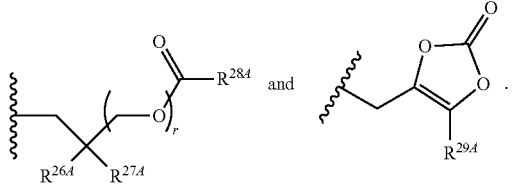

In other embodiments, $R^{6A}$ can be

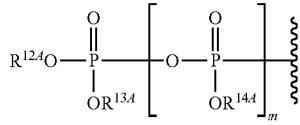

and $R^{7A}$ can be absent or hydrogen. In other embodiments, $R^{6A}$ and $R^{7A}$ can be taken together to form a moiety selected from an optionally substituted

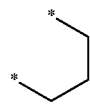 [SMILES: *CCC*]

and an optionally substituted

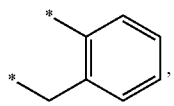

wherein the oxygens connected to $R^{6A}$ and $R^{7A}$, the phosphorus and the moiety form a six-membered to ten-membered ring system.

In some embodiments, $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative. The amino acid portion (of the optionally substituted N-linked amino acid and the optionally substituted N-linked amino acid ester derivative) can have various stereochemical configurations. For example, the amino acid portion can be racemic, an L-stereoisomer, a D-stereoisomer or a mixture of L- and D-stereoisomers that is enriched in one or the other of the stereoisomers. In an embodiment, the L-stereoisomer content of the amino acid portion is at least about 90%, at least about 95%, or at least about 99%, by weight based on the mixture of L- and D-stereoisomers.

In some embodiments, $R^{10A}$ and $R^{11A}$ can be independently an optionally substituted N-linked amino acid or an optionally substituted N-linked amino acid ester derivative; $R^{12A}$, $R^{13A}$ and $R^{14A}$ can be independently absent or hydrogen; each $R^{15A}$, each $R^{16A}$, each $R^{17A}$ and each $R^{18A}$ can be independently hydrogen, an optionally substituted $C_{1-24}$ alkyl or alkoxy; $R^{19A}$, $R^{20A}$, $R^{22A}$ and $R^{23A}$ can be independently selected from hydrogen, an optionally substituted $C_{1-24}$ alkyl and an optionally substituted aryl; $R^{21A}$ and $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

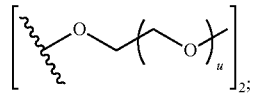

$R^{25A}$ and $R^{29A}$ can be independently selected from hydrogen, an optionally substituted $C_{1-24}$ alkyl and an optionally substituted aryl; $R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R'''^{A}$ can be an optionally substituted $C_{1-24}$-alkyl; m and t can be independently 0 or 1; p and q can be independently selected from 1, 2 and 3; r can be 1 or 2; s can be 0, 1, 2 or 3; u can be 1 or 2; and $Z^{1A}$, $Z^{2A}$, $Z^{3A}$ and $Z^{4A}$ can each independently be O or S.

In some embodiments, $R^{5A}$ can be

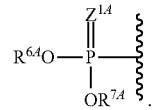

In some embodiments, $R^{6A}$ and $R^{7A}$ can be both hydrogen. In other embodiments, $R^{6A}$ and $R^{7A}$ can be both absent. In still other embodiments, at least one $R^{6A}$ and $R^{7A}$ can be absent. In yet still other embodiments, at least one $R^{6A}$ and $R^{7A}$ can be hydrogen. Those skilled in the art understand that when $R^{6A}$ and/or $R^{7A}$ are absent, the associated oxygen(s) will have a negative charge. For example, when $R^{6A}$ is absent, the oxygen associated with $R^{6A}$ will have a negative charge. In some embodiments, $Z^{1A}$ can be O (oxygen). In other embodiments, $Z^{1A}$ can be S (sulfur). In some embodiments, $R^{5A}$ can be a monophosphate. In other embodiments, $R^{5A}$ can be a monothiophosphate.

In some embodiments, when $R^{5A}$ is

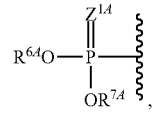

one of $R^{6A}$ and $R^{7A}$ can be hydrogen, and the other of $R^{6A}$ and $R^{7A}$ can be selected from an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6A}$ and $R^{7A}$ can be hydrogen, and the other of $R^{6A}$ and $R^{7A}$ can be an optionally substituted $C_{1-24}$ alkyl. In other embodiments, both $R^{6A}$ and $R^{7A}$ can be independently selected from an optionally substituted $C_{1-24}$ alkyl, an optionally substituted $C_{3-24}$ alkenyl, an optionally substituted $C_{3-24}$ alkynyl, an optionally substituted $C_3$-6 cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6A}$ and $R^{7A}$ can be an optionally substituted $C_{1-24}$ alkyl. In other embodiments, both $R^{6A}$ and $R^{7A}$ can be an optionally substituted $C_{3-24}$ alkenyl. In some embodiments, $R^{6A}$ and $R^{7A}$ can be independently an optionally substituted version of the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl.

In some embodiments, at least one of $R^{6A}$ and $R^{7A}$ can be *—$(CR^{15A}R^{16A})_p$—O—$C_{1-24}$ alkyl. In other embodiments, $R^{6A}$ and $R^{7A}$ can be both *—$(CR^{15A}R^{16A})_p$—O—$C_{1-24}$ alkyl. In some embodiments, each $R^{15A}$ and each $R^{16A}$ can be hydrogen. In other embodiments, at least one of $R^{15A}$ and $R^{16A}$ can be an optionally substituted $C_{1-24}$ alkyl. In other embodiments, at least one of $R^{15A}$ and $R^{16A}$ can be an alkoxy (for example, benzoxy). In some embodiments, p can be 1. In other embodiments, p can be 2. In still other embodiments, p can be 3.

In some embodiments, at least one of $R^{6A}$ and $R^{7A}$ can be *—$(CR^{17A}R^{18A})_q$—O—$C_{2-24}$ alkenyl. In other embodiments, $R^{6A}$ and $R^{7A}$ can be both *—$(CR^{17A}R^{18A})_q$—O—$C_{2-24}$ alkenyl. In some embodiments, each $R^{17A}$ and each $R^{18A}$ can be hydrogen. In other embodiments, at least one of $R^{17A}$ and $R^{18A}$ can be an optionally substituted $C_{1-24}$ alkyl. In some embodiments, q can be 1. In other embodiments, q can be 2. In still other embodiments, q can be 3. When at least one of $R^{6A}$ and $R^{7A}$ is *—$(CR^{15A}R^{16A})_p$—O—$C_{1-24}$ alkyl or *—$(CR^{17A}R^{18A})_q$—O—$C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{5A}$ is

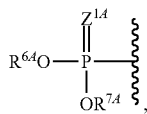

at least one of $R^{6A}$ and $R^{7A}$ can be selected from

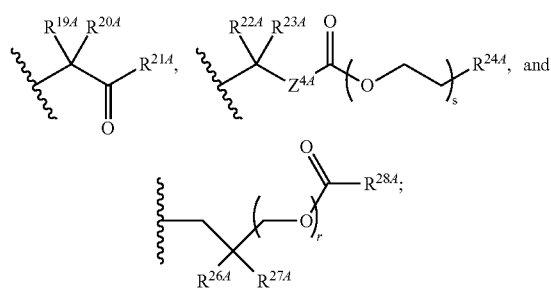

and the other of $R^{6A}$ and $R^{7A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6A}$ and $R^{7A}$ can be

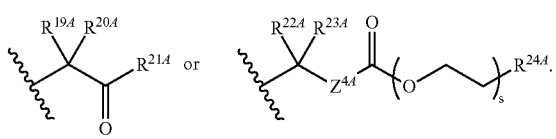

In some embodiments, both $R^{6A}$ and $R^{7A}$ can be

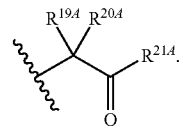

When one or both of $R^{6A}$ and $R^{7A}$ are

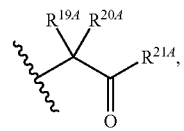

$R^{19A}$ and $R^{20A}$ can be independently selected from hydrogen, an optionally substituted $C_{1-24}$ alkyl and an optionally substituted aryl; and $R^{21A}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

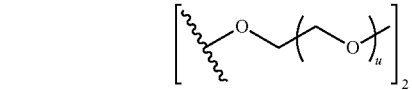

In some embodiments, $R^{19A}$ and $R^{20A}$ can be hydrogen. In other embodiments, at least one of $R^{19A}$ and $R^{20A}$ can be an optionally substituted $C_{1-24}$ alkyl or an optionally substituted aryl. In some embodiments, $R^{21A}$ can be an optionally substituted $C_{1-24}$ alkyl. In other embodiments, $R^{21A}$ can be an optionally substituted aryl. In still other embodiments, $R^{21A}$ can be an optionally substituted —O—$C_{1-24}$ alkyl or an optionally substituted —O-aryl. In some embodiments, $R^{21A}$ can be an optionally substituted —O—$C_{1-24}$ alkyl, an optionally substituted —O-aryl, an optionally substituted —O-heteroaryl or an optionally substituted —O-monocyclic heterocyclyl.

In some embodiments, both $R^{6A}$ and $R^{7A}$ can be

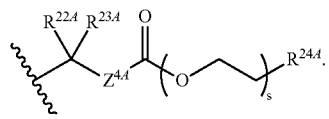

When one or both of $R^{6A}$ and $R^{7A}$ are

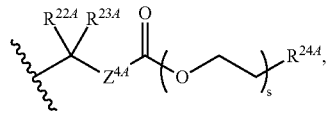

$R^{22A}$ and $R^{23A}$ can be independently selected from hydrogen, an optionally substituted $C_{1-24}$ alkyl and an optionally substituted aryl; $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

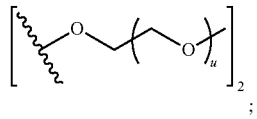

and $Z^{4A}$ can be independently O (oxygen) or S (sulfur). In some embodiments, $R^{22A}$ and $R^{23A}$ can be hydrogen. In other embodiments, at least one of $R^{22A}$ and $R^{23A}$ can be an optionally substituted $C_{1-24}$ alkyl or an optionally substituted aryl. In some embodiments, $R^{24A}$ can be an optionally substituted $C_{1-24}$ alkyl. In other embodiments, $R^{24A}$ can be an optionally substituted aryl. In still other embodiments, $R^{24A}$ can be an optionally substituted —O—$C_{1-24}$ alkyl or an optionally substituted —O-aryl. In some embodiments, $Z^{4A}$ can be O (oxygen). In other embodiments, $Z^{4A}$ can be or S (sulfur). In some embodiments, s can be 0. In other embodiments, s can be 1. In still other embodiments, s can be 2. In yet still embodiments, s can be 3. In some embodiments, s can be 0, and $R^{24A}$ can be

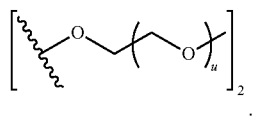

In some embodiments, u can be 1. In other embodiments, u can be 2. In some embodiments, one or both of $R^{6A}$ and $R^{7A}$ can be isopropyloxycarbonyloxymethyl (POC). In some embodiments, one or both of $R^{6A}$ and $R^{7A}$ can be pivaloyloxymethyl (POM). In some embodiments, $R^{6A}$ and $R^{7A}$ can be both a isopropyloxycarbonyloxymethyl group, and form a bis(isopropyloxycarbonyloxymethyl) (bis(POC)) prodrug. In some embodiments, $R^{6A}$ and $R^{7A}$ can be both a pivaloyloxymethyl group, and form a bis(pivaloyloxymethyl) (bis(POM)) prodrug.

In some embodiments, both $R^{6A}$ and $R^{7A}$ can be

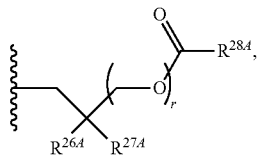

wherein $R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and r can be 1 or 2.

In some embodiments, $R^{6A}$ and $R^{7A}$ can be both an optionally substituted aryl. In some embodiments, at least one of $R^{6A}$ and $R^{7A}$ can be an optionally substituted aryl. For example, both $R^{6A}$ and $R^{7A}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6A}$ and $R^{7A}$ is a substituted phenyl, the substituted phenyl can be a para-, ortho- or meta-substituted phenyl.

In some embodiments, $R^{6A}$ and $R^{7A}$ can be both an optionally substituted aryl($C_{1-6}$ alkyl). In some embodiments, at least one of $R^{6A}$ and $R^{7A}$ can be an optionally substituted aryl($C_{1-6}$ alkyl). For example, both $R^{6A}$ and $R^{7A}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6A}$ and $R^{7A}$ can be both

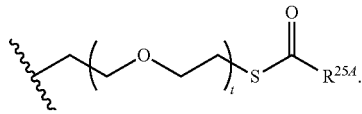

In some embodiments, at least one of $R^{6A}$ and $R^{7A}$ can be

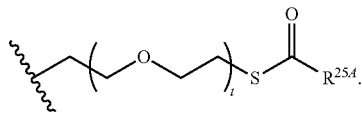

In some embodiments, $R^{25A}$ can be hydrogen. In other embodiments, $R^{25A}$ can be an optionally substituted $C_{1-24}$ alkyl. In still other embodiments, $R^{25A}$ can be an optionally substituted aryl. In some embodiments, $R^{25A}$ can be a $C_{1-6}$ alkyl, for example, methyl, ethyl, n-propyl, isopropyl, n-butyl, isobutyl, tert-butyl, pentyl (branched and straight-chained) and hexyl (branched and straight-chained). In some embodiments, t can be 0. In other embodiments, t can be 1. In some embodiments, one or both of $R^{6A}$ and $R^{7A}$ can be a S-acylthioethyl (SATE).

In some embodiments, $R^{6A}$ and $R^{7A}$ can be both

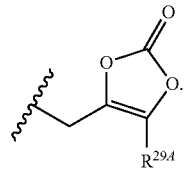

In some embodiments, at least one of $R^{6A}$ and $R^{7A}$ can be

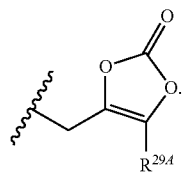

In some embodiments, $R^{29A}$ can be hydrogen. In other embodiments, $R^{29A}$ can be an optionally substituted $C_{1-24}$ alkyl. In some embodiments, $R^{29A}$ can be a $C_{1-4}$ alkyl, such as methyl, ethyl, n-propyl, iso-propyl, n-butyl, iso-butyl and t-butyl. In still other embodiments, $R^{29A}$ can be an optionally substituted aryl, such as an optionally substituted phenyl or an optionally substituted naphthyl. In some embodiments, $R^{6A}$ and $R^{7A}$ can be both a dioxolenone group and form a dioxolenone prodrug.

In some embodiments, $R^{5A}$ can be

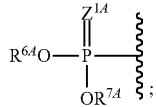

$R^{6A}$ can be

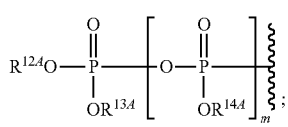

$R^{7A}$ can be absent or hydrogen; $R^{12A}$, $R^{13A}$ and $R^{14A}$ can be independently absent or hydrogen; and m can be 0 or 1. In some embodiments, m can be 0, and $R^{7A}$, $R^{12A}$ and $R^{13A}$ can be independently absent or hydrogen. In other embodiments, m can be 1, and $R^{7A}$, $R^{12A}$, $R^{13A}$ and $R^{14A}$ can be independently absent or hydrogen. Those skilled in the art understand that when m is 0, $R^{6A}$ can be diphosphate, when $Z^{1A}$ is oxygen, or an alpha-thiodiphosphate, when $Z^{1A}$ is sulfur. Likewise, those skilled in the art understand that when m is 1, $R^{6A}$ can be triphosphate, when $Z^{1A}$ is oxygen, or an alpha-thiotriphosphate, when $Z^{1A}$ is sulfur.

In some embodiments, $R^{6A}$ and $R^{7A}$ can be taken together to form an optionally substituted

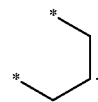

For example, $R^{5A}$ can be an optionally substituted

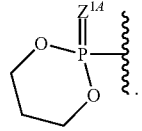

When substituted, the ring can be substituted 1, 2, 3 or 3 or more times. When substituted with multiple substituents, the substituents can be the same or different. In some embodiments, when $R^{5A}$ is

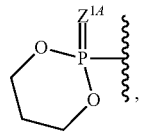

the ring can be substituted with an optionally substituted aryl group and/or an optionally substituted heteroaryl. An example of a suitable heteroaryl is pyridinyl. In some embodiments, $R^{6A}$ and $R^{7A}$ can be taken together to form an optionally substituted

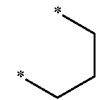

such as

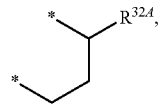

wherein $R^{32A}$ can be an optionally substituted aryl, an optionally substituted heteroaryl or an optionally substituted heterocyclyl. In some embodiments, $R^{6A}$ and $R^{7A}$ can form a cyclic 1-aryl-1,3-propanyl ester (HepDirect) prodrug moiety.

In some embodiments, $R^{6A}$ and $R^{7A}$ can be taken together to form an optionally substituted

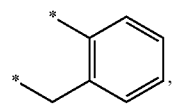 [SMILES: *Cc1ccccc1*]

wherein the oxygens connected to $R^{6A}$ and $R^{7A}$, the phosphorus and the moiety form a six-membered to ten-membered ring system. Example of an optionally substituted include

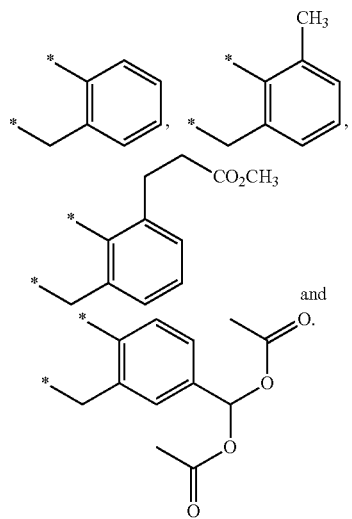

In some embodiments, $R^{6A}$ and $R^{7A}$ can form a cyclosaligenyl (cycloSal) prodrug.

In some embodiments, $R^{6A}$ and $R^{7A}$ can be the same. In some embodiments, $R^{6A}$ and $R^{7A}$ can be different.

In some embodiments, $Z^{1A}$ can be oxygen. In other embodiments, $Z^{1A}$ can be sulfur.

In some embodiments, $R^{5A}$ can be

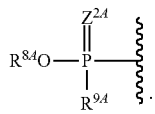

In some embodiments, $R^{8A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl. In an embodiment, $R^{5A}$ is hydrogen,

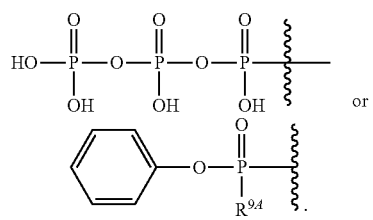

In some embodiments, $R^A$ can be hydrogen, and $R^{9A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained) and hexyl (branched and straight-chained). In other embodiments, $R^{8A}$ can be hydrogen, and $R^{9A}$ can be $NR^{30A}R^{31A}$, wherein $R^{30}$ and $R^{31}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^A$ can be absent or hydrogen; and $R^{9A}$ can be an optionally substituted N-linked amino acid or an optionally substituted N-linked amino acid ester derivative. In other embodiments, $R^A$ can be an optionally substituted aryl; and $R^{9A}$ can be an optionally substituted N-linked amino acid or an optionally substituted N-linked amino acid ester derivative. In still other embodiments, $R^A$ can be an optionally substituted heteroaryl; and $R^{9A}$ can be an optionally substituted N-linked amino acid or an optionally substituted N-linked amino acid ester derivative. In some embodiments, $R^{9A}$ can be an amino acid selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. The amino acid can have various stereochemical configurations. For example, the amino acid can be racemic, an L-stereoisomer, a D-stereoisomer or a mixture of L- and D-stereoisomers that is enriched in one or the other of the stereoisomers. In an embodiment, the L-stereoisomer content of the amino acid is at least about 90%, at least about 95%, or at least about 99%, by weight based on the mixture of L- and D-stereoisomers. Examples of an optionally substituted N-linked amino acid ester derivatives include optionally substituted versions of the following: alanine isopropyl ester, alanine cyclohexyl ester, alanine neopentyl ester, valine isopropyl ester and leucine isopropyl ester. In some embodiments, $R^{9A}$ can have the structure

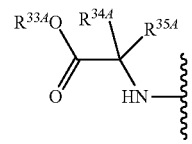

wherein $R^{33A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{34A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{35A}$ can be hydrogen or an optionally substituted $C_{1-4}$-alkyl; or $R^{34A}$ and $R^{35A}$ can be taken together to form an optionally substituted $C_{3-6}$ cycloalkyl. The amino acid portion of the optionally substituted N-linked amino acid ester derivatives can have the various stereochemical configurations that are described above for amino acids. In an embodiment, $R^{9A}$ is

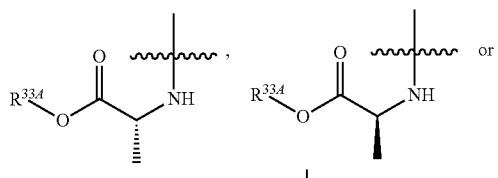, 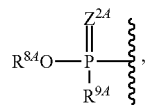 or

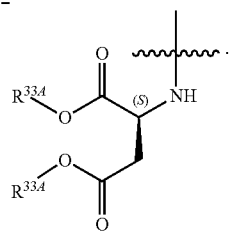.

In an embodiment, $R^{33A}$ is $C_{1-6}$ alkyl.

When $R^{34A}$ is substituted, $R^{34A}$ can be substituted with one or more substituents selected from N-amido, mercapto, alkylthio, an optionally substituted aryl, hydroxy, an optionally substituted heteroaryl, O-carboxy and amino. In some embodiments, $R^{34A}$ can be an unsubstituted $C_{1-6}$-alkyl, such as those described herein. In some embodiments, $R^{34A}$ can be hydrogen. In other embodiments, $R^{34A}$ can be methyl. In some embodiments, $R^{33A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{33A}$ can be methyl or isopropyl. In some embodiments, $R^{33A}$ can be ethyl or neopentyl. In other embodiments, $R^{33A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{33A}$ can be an optionally substituted cyclohexyl. In still other embodiments, $R^{33A}$ can be an optionally substituted aryl, such as phenyl and naphthyl. In yet still other embodiments, $R^{33A}$ can be an optionally substituted aryl($C_{1-6}$ alkyl). In some embodiments, $R^{33A}$ can be an optionally substituted benzyl. In some embodiments, $R^{33A}$ can be an optionally substituted $C_{1-6}$ haloalkyl, for example, $CF_3$. In some embodiments, $R^{35A}$ can be hydrogen. In other embodiments, $R^{35A}$ can be an optionally substituted $C_{1-4}$-alkyl, such as methyl, ethyl, n-propyl, isopropyl, n-butyl, isobutyl and tert-butyl. In an embodiment, $R^{35A}$ can be methyl. In some embodiments, $R^{34A}$ and $R^{35A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{34A}$ and $R^{35A}$, the carbon to which $R^{34A}$ and $R^{35A}$ are attached may be a chiral center. In some embodiment, the carbon to which $R^{34A}$ and $R^{35A}$ are attached may be a (R)-chiral center. In other embodiments, the carbon to which $R^{34A}$ and $R^{35A}$ are attached may be a (S)-chiral center.

In some embodiments, when $R^{5A}$ is

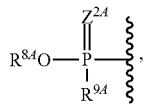, $Z^{2A}$ can be O (oxygen). In other embodiments, when $R^{5A}$ is

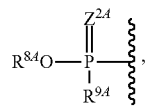, $Z^{2A}$ can be S (sulfur). In some embodiments, when $R^{5A}$ is

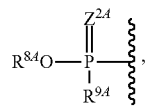, a compound of Formula (I) can be a phosphoramidate prodrug, such as an aryl phosphoramidate prodrug.

In some embodiments, $R^{5A}$ can be

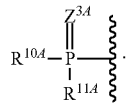.

In some embodiments, $R^{10A}$ and $R^{11A}$ can be both an optionally substituted N-linked amino acid or an optionally substituted N-linked amino acid ester derivative. In some embodiments, one or both of $R^{10A}$ and $R^{11A}$ can be an amino acid independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. The amino acid can have various stereochemical configurations. For example, the amino acid can be racemic, an L-stereoisomer, a D-stereoisomer or a mixture of L- and D-stereoisomers that is enriched in one or the other of the stereoisomers. In an embodiment, the L-stereoisomer content of the amino acid is at least about 90%, at least about 95%, or at least about 99%, by weight based on the mixture of L- and D-stereoisomers. In some embodiments, $R^{10A}$ and $R^{11A}$ can be an optionally substituted version of the following: alanine isopropyl ester, alanine cyclohexyl ester, alanine neopentyl ester, valine isopropyl ester and leucine isopropyl ester. In some embodiments, $R^{10A}$ and $R^{11A}$ can independently have the structure

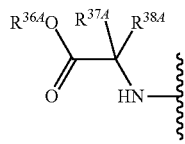

wherein $R^{36A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{37A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{38A}$ can be hydrogen or an optionally substituted $C_{1-4}$-alkyl; or $R^{37A}$ and $R^{38A}$ can be taken together to form an optionally substituted $C_{3-6}$ cycloalkyl.

When $R^{37A}$ is substituted, $R^{37A}$ can be substituted with one or more substituents selected from N-amido, mercapto, alkylthio, an optionally substituted aryl, hydroxy, an optionally substituted heteroaryl, O-carboxy and amino. In some embodiments, $R^{37A}$ can be an unsubstituted $C_{1-6}$-alkyl, such as those described herein. In some embodiments, $R^{37A}$ can be hydrogen. In other embodiments, $R^{37A}$ can be methyl. In some embodiments, $R^{36A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{36A}$ can be methyl or isopropyl. In some embodiments, $R^{36A}$ can be ethyl or neopentyl. In other embodiments, $R^{36A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{36A}$ can be an optionally substituted cyclohexyl. In still other embodiments, $R^{36A}$ can be an optionally substituted aryl, such as phenyl and naphthyl. In yet still other embodiments, $R^{36A}$ can be an optionally substituted aryl($C_{1-6}$ alkyl). In some embodiments, $R^{36A}$ can be an optionally substituted benzyl. In some embodiments, $R^{36A}$ can be an optionally substituted $C_{1-6}$ haloalkyl, for example, $CF_3$. In some embodiments, $R^{38A}$ can be hydrogen. In other embodiments, $R^{38A}$ can be an optionally substituted $C_{1-4}$-alkyl, such as methyl, ethyl, n-propyl, isopropyl, n-butyl, isobutyl and tert-butyl. In an embodiment, $R^{38A}$ can be methyl. In some embodiments, $R^{37A}$ and $R^{38A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{37A}$ and $R^{38A}$, the carbon to which $R^{37A}$ and $R^{38A}$ are attached may be a chiral center. In some embodiment, the carbon to which $R^{37A}$ and $R^{38A}$ are attached may be a (R)-chiral center. In other embodiments, the carbon to which $R^{37A}$ and $R^{38A}$ are attached may be a (S)-chiral center.

Examples of suitable

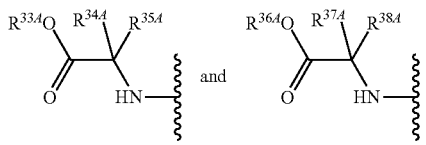

groups include the following:

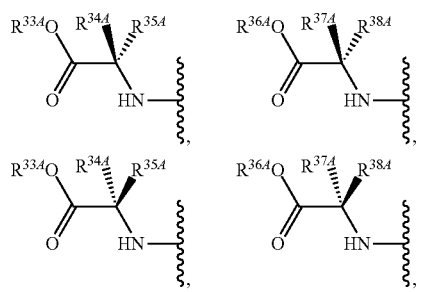

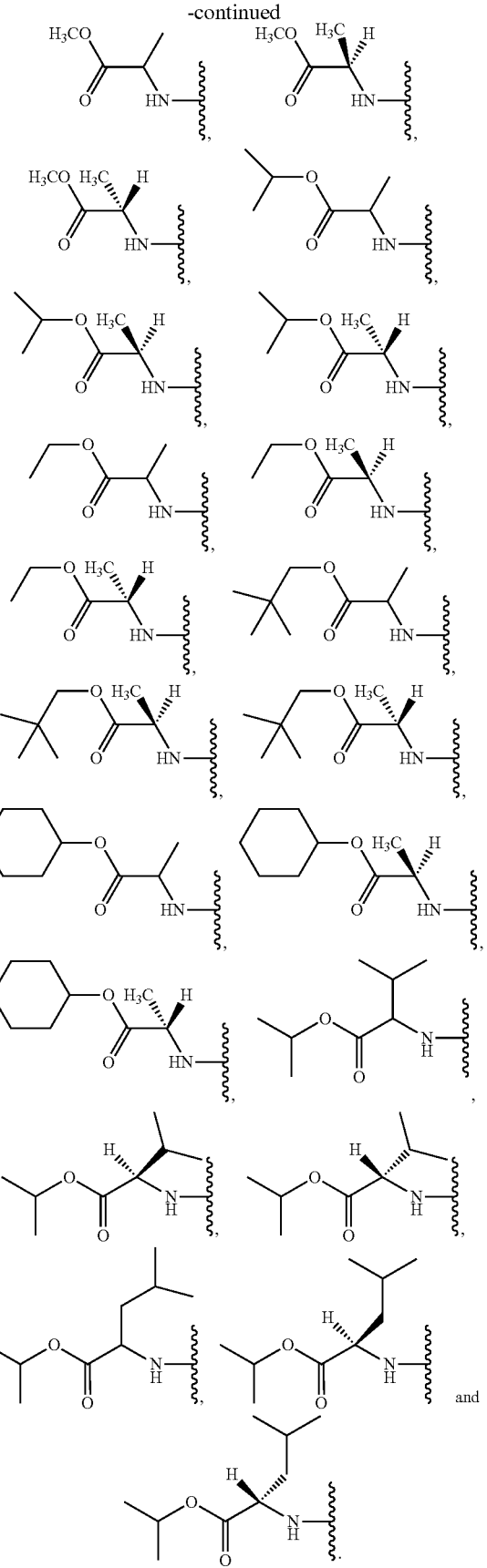

In some embodiments, $R^{10A}$ and $R^{11A}$ can be the same. In some embodiments, $R^{10A}$ and $R^{11A}$ can be different.

In some embodiments, $Z^{3A}$ can be O (oxygen). In other embodiments, $Z^{3A}$ can be S (sulfur). In some embodiments, when $R^{5A}$ is

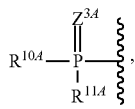

a compound of Formula (I) can be a phosphonic diamide prodrug.

Those skilled in the art understand that when $R^{8A}$, $R^{9A}$, and/or $R^{10A}$ are absent, the associated oxygen(s) will have a negative charge. For example, when $R^{8A}$ is absent, the oxygen associated with $R^{8A}$ will have a negative charge. The variable m in $R^{7A}$ can be 0, 1 or 2. Thus, in an embodiment, $R^{7A}$ can be a monophosphate (m=0), in which case $R^{10A}$ is absent. In another embodiment, $R^{7A}$ can be a diphosphate (m=1). In yet another embodiment, $R^{7A}$ can be a triphosphate (m=2).

By neutralizing the charge on the phosphorus moiety of the compounds of Formulae (I), penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Furthermore, in some embodiments, varying the substituents on a compound described herein, such as a compound of Formula (I), or a pharmaceutically acceptable salt of any of the foregoing, can help maintain the efficacy of the compound by reducing undesirable effects.

In some embodiments, $R^{5A}$ can be hydrogen. In some embodiments, $R^{5A}$ can be an optionally substituted acyl. In other embodiments, $R^{5A}$ can be —C(=O)$R^{39A}$ wherein $R^{39A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{39A}$ can be a substituted $C_{1-12}$ alkyl. In other embodiments, $R^{39A}$ can be an unsubstituted $C_{1-12}$ alkyl.

In still other embodiments, $R^{5A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can be selected such that —O$R^{5A}$ has the structure

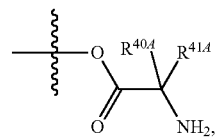

wherein $R^{40A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{41A}$ can be hydrogen or an optionally substituted $C_{1-4}$-alkyl; or $R^{40A}$ and $R^{41A}$ can be taken together to form an optionally substituted $C_{3-6}$ cycloalkyl.

When $R^{40A}$ is substituted, $R^{40A}$ can be substituted with one or more substituents selected from N-amido, mercapto, alkylthio, an optionally substituted aryl, hydroxy, an optionally substituted heteroaryl, O-carboxy and amino. In some embodiments, $R^{40A}$ can be an unsubstituted $C_{1-6}$-alkyl, such as those described herein. In some embodiments, $R^{40A}$ can be hydrogen. In other embodiments, $R^{40A}$ can be methyl. In some embodiments, $R^{41A}$ can be hydrogen. In other embodiments, $R^{41A}$ can be an optionally substituted $C_{1-4}$-alkyl, such as methyl, ethyl, n-propyl, isopropyl, n-butyl, isobutyl and tert-butyl. In an embodiment, $R^{41A}$ can be methyl. Depending on the groups that are selected for $R^{40A}$ and $R^{41A}$, the carbon to which $R^{40A}$ and $R^{41A}$ are attached may be a chiral center. In some embodiment, the carbon to which $R^{40A}$ and $R^{41A}$ are attached may be a (R)-chiral center. In other embodiments, the carbon to which $R^{40A}$ and $R^{41A}$ are attached may be a (S)-chiral center.

Examples of suitable

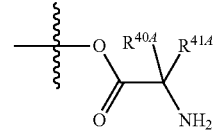

include the following:

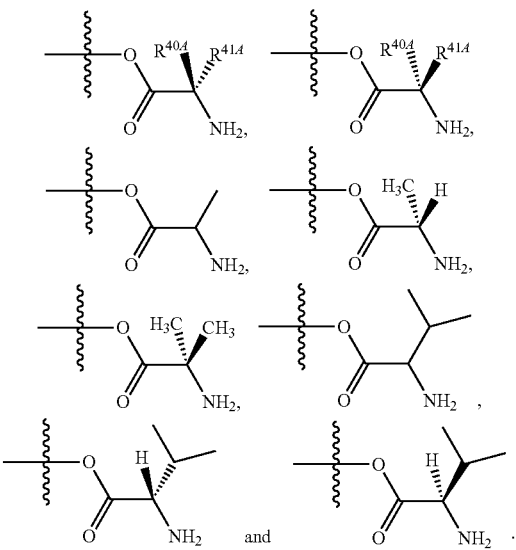

In various embodiments a compound of Formula (I), or a pharmaceutically acceptable salt thereof, is a panviral compound. As used herein in this context, the term "panviral" refers to a compound (e.g., a nucleoside analog or a nucleotide analog) that exhibits pharmaceutically significant activity against viruses in two or more families of viruses. The degree to which a compound exhibits pharmaceutically significant activity can be determined by using a validated assay that is appropriate for the virus being tested. Such assay methods are known to those skilled in the art and include the assay methods described in the Examples below. In general, a compound of Formula (I), or a pharmaceutically acceptable salt thereof, is considered to be panviral if it exhibits an $EC_{50}$ and/or $IC_{50}$ value of 100 µM or less in at least one assay for a virus in a first virus family and also exhibits an $EC_{50}$ and/or $IC_{50}$ value of 100 µM or less in at least one assay for a virus in a second virus family that is different from the first family. It will be apparent to those skilled in the art that compounds having greater activity are also considered panviral. For example, a compound of Formula (I), or a pharmaceutically acceptable salt thereof, is also considered to be panviral if it exhibits an $EC_{50}$ and/or $IC_{50}$ value of 10 µM or less in at least one assay for a virus in a first virus family and also exhibits an $EC_{50}$ and/or $IC_{50}$ value of 100 µM or less in at least one assay for a virus in a second virus family that is different from the first family.

In various embodiments a compound of Formula (I), or a pharmaceutically acceptable salt thereof, is a low toxicity compound. As used herein in this context, the term "low toxicity" refers to a compound (e.g., a nucleoside analog or a nucleotide analog) that exhibits pharmaceutically insignificant toxicity when tested using a validated toxicity assay that is appropriate for the virus being tested. Such assay methods are known to those skilled in the art and include the assay methods described in the Examples below. In general, a compound of Formula (I), or a pharmaceutically acceptable salt thereof, is considered to exhibit pharmaceutically insignificant toxicity if it exhibits a 50% cytotoxic concentration ($CC_{50}$) value of 10 µM or more. It will be apparent to those skilled in the art that less toxic compounds are also considered low toxicity. For example, a compound is also considered to exhibit pharmaceutically insignificant toxicity if it exhibits a $CC_{50}$ value of 100 µM or more.

In various embodiments a compound of Formula (I), or a pharmaceutically acceptable salt thereof, is a low toxicity panviral nucleoside analog. As used herein in this context, the term "low toxicity panviral" refers to a compound of Formula (I), or a pharmaceutically acceptable salt thereof, that is both low toxicity and panviral, as described above.

Synthesis

Compounds of Formula (I), or a pharmaceutically acceptable salt thereof may be prepared in various ways, including those known to those skilled in the art. The synthetic routes described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims. Examples of methods are described in the Examples below.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, >60%, >70%, >80%, >90%, >95%, or >98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

In an embodiment, a panviral treatment as described elsewhere herein is formulated for administration to a subject having a viral infection. For example, those skilled in the art appreciate that, depending on the type of viral infection, it may be more advantageous to administer a panviral treatment that has been formulated in a particular manner, e.g., in the form of a pharmaceutical composition that facilitates administration by a particular route (e.g., oral, aerosol, injection, etc.) and/or with appropriate labeling for treatment of the condition for which it is indicated. An embodiment provides a panviral treatment formulated for administration to a subject having a Picornaviridae, Flaviviridae, Filoviridae, Pneumoviridae and/or Coronaviridae viral infection.

Methods of Use

Some embodiments disclosed herein relate to a method of treating and/or ameliorating a Picornaviridae viral infection that can include administering to a subject infected with the Picornaviridae virus an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating a Picornaviridae viral infection that can include administering to a subject identified as suffering from the viral infection an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof).

Some embodiments described herein relate to methods of using one or more compounds described herein (such as a compound of Formula (I), or a pharmaceutically acceptable salt thereof), in the manufacture of a medicament for ameliorating and/or treating a Picornaviridae viral infection that can include administering to a subject infected with the Picornaviridae virus an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating a Picornaviridae viral infection by administering to a subject infected with the Picornaviridae virus an effective amount of one or more compounds described herein.

Some embodiments disclosed herein relate to methods of ameliorating and/or treating a Picornaviridae viral infection that can include contacting a cell infected with the Picornaviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating a Picornaviridae viral infection that can include contacting a cell infected with the Picornaviridae virus with an effective amount of said compound(s). Still other embodiments described herein relate to one or more compounds described herein (such as a compound of Formula (I), or a pharmaceutically acceptable salt thereof), that can be used for ameliorating and/or treating a Picornaviridae viral infection by contacting a cell infected with the Picornaviridae virus with an effective amount of said compound(s).

Some embodiments disclosed herein relate to methods of inhibiting replication of a Picornaviridae virus that can include contacting a cell infected with the Picornaviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Picornaviridae virus that can include contacting a cell infected with the Picornaviridae virus with an effective amount of said compound(s). Still other embodiments described herein relate to a compound described herein (such as a compound of Formula (I), or a pharmaceutically acceptable salt thereof), that can be used for inhibiting replication of a Picornaviridae virus by contacting a cell infected with the Picornaviridae virus with an effective amount of said compound(s). In some embodiments, a compound of Formula (I), or a pharmaceutically acceptable salt thereof, can inhibit a RNA dependent RNA polymerase of a Picornaviridae virus, and thus, inhibit the replication of RNA. In some embodiments, a polymerase of a Picornaviridae virus can be inhibited by contacting a cell infected with the Picornaviridae virus with a compound described herein (such as a compound of Formula (I), or a pharmaceutically acceptable salt thereof).

In some embodiments, the Picornaviridae virus can be selected from an Aphthovirus, an Enterovirus, a Rhinovirus, a Hepatovirus and a Parechovirus. In some embodiments, a compound described herein (for example, a compound of Formula (I), or a pharmaceutically acceptable salt thereof) can ameliorate and/or treat a Rhinovirus infection. For example, by administering an effective amount of a compound of Formula (I), or a pharmaceutically acceptable salt thereof, to a subject infected with the Rhinovirus and/or by contacting a cell infected with the Rhinovirus. In some embodiments, a compound described herein (for example, a compound of Formula (I), or a pharmaceutically acceptable salt thereof) can inhibit replication of a Rhinovirus. In some embodiments, a compound of Formula (I), or a pharmaceutically acceptable salt thereof, can be effective against a Rhinovirus, and thereby ameliorate one or more symptoms of a Rhinovirus infection.

Various indicators for determining the effectiveness of a method for treating a Picornaviridae viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator(s) of disease response. Further indicators include one or more overall quality of life health indicators, such as reduced illness duration, reduced illness severity, reduced time to return to normal health and normal activity, and reduced time to alleviation of one or more symptoms. In some embodiments, a compound of Formula (I), or a pharmaceutically acceptable salt thereof, can result in the reduction, alleviation or positive indication of one or more of the aforementioned indicators compared to an untreated subject. Effects/symptoms of a Picornaviridae viral infection are described herein, and include, but are not limited to, fever, blisters, rash, meningitis, conjunctivitis, acute hemorrhagic conjunctivitis (AHC), sore throat, nasal congestion, runny nose, sneezing, coughing, loss of appetite, muscle aches, headache, fatigue, nausea, jaundice, encephalitis, herpangina, myocarditis, pericarditis, meningitis, Bornholm disease, myalgia, nasal congestion, muscle weakness, loss of appetite, fever, vomiting, abdominal pain, abdominal discomfort, dark urine and muscle pain.

Some embodiments disclosed herein relate to a method of treating and/or ameliorating a Flaviviridae viral infection that can include administering to a subject infected with the Flaviviridae virus an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating a Flaviviridae viral infection that can include administering to a subject an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Some embodiments described herein relate to methods of using one or more compounds described herein (such as a compound of Formula (I), or a pharmaceutically acceptable salt thereof), in the manufacture of a medicament for ameliorating and/or treating a Flaviviridae viral infection that can include administering an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating a Flaviviridae viral infection by administering to a subject an effective amount of one or more compounds described herein.

Some embodiments disclosed herein relate to methods of ameliorating and/or treating a Flaviviridae viral infection that can include contacting a cell infected with the Flaviviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating a Flaviviridae viral infection that can include contacting a cell infected with the Flaviviridae virus with an effective amount of said compound(s). Still other embodiments described herein relate to one or more compounds described herein (such as a compound of Formula (I), or a pharmaceutically acceptable salt thereof), that can be used for ameliorating and/or treating a Flaviviridae viral infection by contacting a cell infected with the Flaviviridae virus with an effective amount of said compound(s).

Some embodiments disclosed herein relate to methods of inhibiting replication of a Flaviviridae virus that can include contacting a cell infected with the Flaviviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Flaviviridae virus that can include contacting a cell infected with the Flaviviridae virus with an effective amount of said compound(s). Still other embodiments described herein relate to a compound described herein (such as a compound of Formula (I), or a pharmaceutically acceptable salt thereof), that can be used for inhibiting replication of a Flaviviridae virus by contacting a cell infected with the Flaviviridae virus with an effective amount of said compound(s). In some embodiments, a polymerase of a Flaviviridae virus can be inhibited by contacting a cell infected with the Flaviviridae virus with a compound described herein (such as a compound of Formula (I), or a pharmaceutically acceptable salt thereof), and thereby, inhibit the replication of RNA.

Some embodiments disclosed herein relate to methods of ameliorating and/or treating a HCV infection that can include contacting a cell infected with HCV with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to methods of using one or more compounds described herein (such as a compound of Formula (I), or a pharmaceutically acceptable salt thereof), in the manufacture of a medicament for ameliorating and/or treating a HCV infection that can include contacting a cell infected with HCV with an effective amount of said compound(s). Still other embodiments described herein relate to one or more compounds described herein (such as a compound of Formula (I), or a pharmaceutically acceptable salt thereof), that can be used for ameliorating and/or treating a HCV infection by contacting a cell infected with HCV with an effective amount of said compound(s).

Some embodiments described herein relate to a method of inhibiting NS5B polymerase activity that can include contacting a cell infected with hepatitis C virus with an effective amount of a compound of Formula (I), or a pharmaceutically acceptable salt thereof. As noted above, NS5B is believed to be an RNA-dependent RNA polymerase involved in the replication of HCV RNA. Some embodiments described herein relate to a method of inhibiting NS5B polymerase activity that can include administering to a subject infected with hepatitis C virus an effective amount of a compound of Formula (I), or a pharmaceutically acceptable salt thereof. In some embodiments, a compound of Formula (I), or a pharmaceutically acceptable salt thereof, can inhibit a RNA dependent RNA polymerase, and thus, inhibit the replication of HCV RNA. In some embodiments, a compound of Formula (I), or a pharmaceutically acceptable salt thereof, can inhibit a HCV polymerase (for example, NS5B polymerase).

Some embodiments described herein relate to a method of treating a condition selected from liver fibrosis, liver cirrhosis and liver cancer in a subject suffering from one or more of the aforementioned liver conditions that can include administering to the subject an effective amount of a compound or a pharmaceutical composition described herein (for example, a compound of Formula (I), or a pharmaceutically acceptable salt thereof), wherein the liver condition is caused by a HCV infection. Some embodiments described herein relate to a method of increasing liver function in a subject having a HCV infection that can include administering to the subject an effective amount of a compound or a pharmaceutical composition described herein (for example, a compound of Formula (I), or a pharmaceutically acceptable salt thereof). Also contemplated is a method for reducing or eliminating further virus-caused liver damage in a subject having an HCV infection by administering to the subject an effective amount of a compound or a pharmaceutical composition described herein (for example, a compound of Formula (I), or a pharmaceutically acceptable salt thereof). In some embodiments, this method can include slowing or halting the progression of liver disease. In other embodiments, the course of the disease can be reversed, and stasis or improvement in liver function is contemplated. In some embodiments, liver fibrosis, liver cirrhosis and/or liver cancer can be treated; liver function can be increased; virus-caused liver damage can be reduced or eliminated; progression of liver disease can be slowed or halted; the course of the liver disease can be reversed and/or liver function can be improved or maintained by contacting a cell infected with hepatitis C virus with an effective amount of a compound described herein (for example, a compound of Formula (I), or a pharmaceutically acceptable salt thereof.)

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of a compound of Formula (I), or a pharmaceutical acceptable salt thereof, or a pharmaceutical composition that includes an effective amount of a compound of Formula (I), or a pharmaceutical acceptable salt of any of the foregoing, can be effective to treat at least one genotype of HCV. In some embodiments, a compound described herein (for example, a compound of Formula (I), or a pharmaceutically acceptable salt thereof) can be effective to treat all 11 genotypes of HCV. In some embodiments, a compound described herein (for example, a compound of Formula (I), or a pharmaceutically acceptable salt thereof) can be effective to treat 3 or more, 5 or more, 7 or more, or 9 or more genotypes of HCV. In some embodiments, a compound of Formula (I), or a pharmaceutical acceptable salt thereof, can be more effective against a larger number of HCV genotypes than the standard of care. In some embodiments, a compound of Formula (I), or a pharmaceutically acceptable salt thereof, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase and/or other indicator of disease response. Similarly, successful therapy with an effective amount of a compound or a pharmaceutical composition described herein (for example, a compound of Formula (I), or a pharmaceutically acceptable salt thereof) can reduce the incidence of liver cancer in HCV infected subjects.

In some embodiments, a compound described herein (for example, a compound of Formula (I), or a pharmaceutical acceptable salt thereof) can be used to ameliorate and/or treat a Flavivirus infection. In some embodiments, a compound described herein (for example, a compound of Formula (I), or a pharmaceutical acceptable salt thereof) can inhibit replication of a Flavivirus.

In some embodiments, the Flavivirus can be a West Nile virus. In some embodiments, a compound described herein (for example, a compound of Formula (I), or a pharmaceutical acceptable salt thereof) can treat and/or ameliorate a dengue virus, such as DENV-1, DENV-2, DENV-3 and DENV-4. A dengue virus infection can cause dengue hemorrhagic fever and/or dengue shock syndrome. In some embodiments, a compound described herein (for example, a compound of Formula (I), or a pharmaceutical acceptable salt thereof) can treat and/or ameliorate dengue hemorrhagic fever and/or dengue shock syndrome. In some embodiments, the Flavivirus can be yellow fever virus. In yet still other embodiments, the Flavivirus can be an encephalitis virus from within the Flavivirus genus. Examples of encephalitis viruses include, but are not limited to, Japanese encephalitis virus, St. Louis encephalitis virus and tick borne encephalitis. In some embodiments, the Flavivirus can be a Zika virus.

Some embodiments disclosed herein relate to a method of treating and/or ameliorating a Filoviridae viral infection that can include administering to a subject infected with the Filoviridae virus an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating a Filoviridae viral infection that can include administering to a subject identified as suffering from the viral infection an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof).

Some embodiments described herein relate to methods of using one or more compounds described herein (such as a compound of Formula (I), or a pharmaceutically acceptable salt thereof), in the manufacture of a medicament for ameliorating and/or treating a Filoviridae viral infection that can include administering to a subject infected with the Filoviridae virus an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating a Filoviridae viral infection by administering to a subject infected with the Filoviridae virus an effective amount of one or more compounds described herein.

Some embodiments disclosed herein relate to methods of ameliorating and/or treating a Filoviridae viral infection that can include contacting a cell infected with the Filoviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating a Filoviridae viral infection that can include contacting a cell infected with the Filoviridae virus with an effective amount of said compound(s). Still other embodiments described herein relate to one or more compounds described herein (such as a compound of Formula (I), or a pharmaceutically acceptable salt thereof), that can be used for ameliorating and/or treating a Filoviridae viral infection by contacting a cell infected with the Filoviridae virus with an effective amount of said compound(s).

Some embodiments disclosed herein relate to methods of inhibiting replication of a Filoviridae virus that can include contacting a cell infected with the Filoviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Filoviridae virus that can include contacting a cell infected with the Filoviridae virus with an effective amount of said compound(s). Still other embodiments described herein relate to a compound described herein (such as a compound of Formula (I), or a pharmaceutically acceptable salt thereof), that can be used for inhibiting replication of a Filoviridae virus by contacting a cell infected with the Filoviridae virus with an effective amount of said compound(s). In some embodiments, a compound of Formula (I), or a pharmaceutically acceptable salt thereof, can inhibit a RNA dependent RNA polymerase of a Filoviridae virus, and thus, inhibit the replication of RNA. In some embodiments, a polymerase of a Filoviridae virus can be inhibited by contacting a cell infected with the Filoviridae virus with a compound described herein (such as a compound of Formula (I), or a pharmaceutically acceptable salt thereof).

In some embodiments, a compound described herein (for example, a compound of Formula (I), or a pharmaceutical acceptable salt thereof) can be used to ameliorate and/or treat a Filoviridae viral infection. In some embodiments, a compound described herein (for example, a compound of Formula (I), or a pharmaceutical acceptable salt thereof) can inhibit replication of a Filovirus.

In some embodiments, the Filoviridae virus can be selected from an Ebolavirus, a Marburgvirus and a Cuevavirus. In some embodiments, a compound described herein (for example, a compound of Formula (I), or a pharmaceutically acceptable salt thereof) can ameliorate and/or treat an Ebolavirus infection. For example, by administering an effective amount of a compound of Formula (I), or a pharmaceutically acceptable salt thereof, to a subject infected with the Ebolavirus and/or by contacting a cell infected with the Ebolavirus. In some embodiments, a compound described herein (for example, a compound of Formula (I), or a pharmaceutically acceptable salt thereof) can inhibit replication of an Ebolavirus. In some embodiments, a compound of Formula (I), or a pharmaceutically acceptable salt thereof, can be effective against an Ebolavirus, and thereby ameliorate one or more symptoms of an Ebolavirus infection. The five recognized species of Ebolavirus are Ebola virus (EBOV), Reston ebolavirus (REBOV), Sudan ebolavirus (SEBOV), Taï Forest ebolavirus (TAFV) and Bundibugyo ebolavirus (BEBOV). The two recognized species of Marburgvirus are Marburg virus (MARV) and Ravn virus (RAVV).

Some embodiments disclosed herein relate to a method of treating and/or ameliorating a Pneumoviridae viral infection that can include administering to a subject infected with the Pneumoviridae virus an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating a Pneumoviridae viral infection that can include administering to a subject identified as suffering from the viral infection an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof).

Some embodiments described herein relate to methods of using one or more compounds described herein (such as a compound of Formula (I), or a pharmaceutically acceptable salt thereof), in the manufacture of a medicament for ameliorating and/or treating a Pneumoviridae viral infection that can include administering to a subject infected with the Pneumoviridae virus an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating a Pneumoviridae viral infection by administering to a subject infected with the Pneumoviridae virus an effective amount of one or more compounds described herein.

Some embodiments disclosed herein relate to methods of ameliorating and/or treating a Pneumoviridae viral infection that can include contacting a cell infected with the Pneumoviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating a Pneumoviridae viral infection that can include contacting a cell infected with the Pneumoviridae virus with an effective amount of said compound(s). Still other embodiments described herein relate to one or more compounds described herein (such as a compound of Formula (I), or a pharmaceutically acceptable salt thereof), that can be used for ameliorating and/or treating a Pneumoviridae viral infection by contacting a cell infected with the Pneumoviridae virus with an effective amount of said compound(s).

Some embodiments disclosed herein relate to methods of inhibiting replication of a Pneumoviridae virus that can include contacting a cell infected with the Pneumoviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Pneumoviridae virus that can include contacting a cell infected with the Pneumoviridae virus with an effective amount of said compound(s). Still other embodiments described herein relate to a compound described herein (such as a compound of Formula (I), or a pharmaceutically acceptable salt thereof), that can be used for inhibiting replication of a Pneumoviridae virus by contacting a cell infected with the Pneumoviridae virus with an effective amount of said compound(s). In some embodiments, a compound of Formula (I), or a pharmaceutically acceptable salt thereof, can inhibit a RNA dependent RNA polymerase of a Pneumoviridae virus, and thus, inhibit the replication of RNA. In some embodiments, a polymerase of a Pneumoviridae virus can be inhibited by contacting a cell infected with the Pneumoviridae virus with a compound described herein (such as a compound of Formula (I), or a pharmaceutically acceptable salt thereof).

In some embodiments, a compound described herein (for example, a compound of Formula (I), or a pharmaceutical acceptable salt thereof) can be used to ameliorate and/or treat a Pneumoviridae viral infection. In some embodiments, a compound described herein (for example, a compound of Formula (I), or a pharmaceutical acceptable salt thereof) can inhibit replication of a Pneumoviridae viral infection. In some embodiments, the Pneumovirus virus can be a Human respiratory syncytial virus (HRSV), such as HRSV-A2, HRSV-B1 and HRSV-S2. HRSV can cause respiratory tract infections, bronchiolitis, pneumonia and severe lower respiratory tract disease.

Some embodiments disclosed herein relate to a method of treating and/or ameliorating a Coronaviridae viral infection that can include administering to a subject infected with the Coronaviridae virus an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof). Other embodiments disclosed herein relate to a method of treating and/or ameliorating a Coronaviridae viral infection that can include administering to a subject identified as suffering from the viral infection an effective amount of one or more compounds described herein (such as a compound of Formula (I), or a pharmaceutically acceptable salt thereof), or a pharmaceutical composition that includes a compound described herein (such as a compound of Formula (I), or a pharmaceutically acceptable salt thereof).

Some embodiments described herein relate to methods of using one or more compounds described herein (such as a compound of Formula (I), or a pharmaceutically acceptable salt thereof), in the manufacture of a medicament for ameliorating and/or treating a Coronaviridae viral infection that can include administering to a subject infected with the Coronaviridae virus an effective amount of one or more compounds described herein (such as a compound of Formula (I), or a pharmaceutically acceptable salt thereof). Still other embodiments described herein relate to one or more compounds described herein (such as a compound of Formula (I), or a pharmaceutically acceptable salt thereof) that can be used for ameliorating and/or treating a Coronaviridae viral infection by administering to a subject infected with the Coronaviridae virus an effective amount of one or more compounds described herein.

Some embodiments disclosed herein relate to methods of ameliorating and/or treating a Coronaviridae viral infection that can include contacting a cell infected with the Coronaviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for ameliorating and/or treating a Coronaviridae viral infection that can include contacting a cell infected with the Coronaviridae virus with an effective amount of said compound(s). Still other embodiments described herein relate to one or more compounds described herein (such as a compound of Formula (I), or a pharmaceutically acceptable salt thereof), that can be used for ameliorating and/or treating a Coronaviridae viral infection by contacting a cell infected with the Coronaviridae virus with an effective amount of said compound(s).

Some embodiments disclosed herein relate to methods of inhibiting replication of a Coronaviridae virus that can include contacting a cell infected with the Coronaviridae virus with an effective amount of one or more compounds described herein (such as a compound of Formula (I), or a pharmaceutically acceptable salt thereof), or a pharmaceutical composition that includes one or more compounds described herein (such as a compound of Formula (I), or a pharmaceutically acceptable salt thereof). Other embodiments described herein relate to using one or more compounds described herein (such as a compound of Formula (I), or a pharmaceutically acceptable salt thereof), in the manufacture of a medicament for inhibiting replication of a Coronaviridae virus that can include contacting a cell infected with the Coronaviridae virus with an effective amount of said compound(s). Still other embodiments described herein relate to a compound described herein (such as a compound of Formula (I), or a pharmaceutically acceptable salt thereof), that can be used for inhibiting replication of a Coronaviridae virus by contacting a cell infected with the Coronaviridae virus with an effective amount of said compound(s). In some embodiments, a compound of Formula (I), or a pharmaceutically acceptable salt thereof, can inhibit a RNA dependent RNA polymerase of a Coronaviridae virus, and thus, inhibit the replication of RNA. In some embodiments, a polymerase of a Coronaviridae virus can be inhibited by contacting a cell infected with the Coronaviridae virus with a compound described herein (such as a compound of Formula (I), or a pharmaceutically acceptable salt thereof).

In some embodiments, a compound described herein (for example, a compound of Formula (I), or a pharmaceutical acceptable salt thereof) can be used ameliorate and/or treat a Coronaviridae viral infection. In some embodiments, a compound described herein (for example, a compound of Formula (I), or a pharmaceutical acceptable salt thereof) can inhibit replication of a Coronaviridae viral. In some embodiments, the Coronavirus virus can be a human alpha coronavirus (HRSV) or a human beta coronavirus. The six coronaviruses that can infect people are: alpha coronaviruses 229E and NL63, and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS).

Various indicators for determining the effectiveness of a method for treating a Picornaviridae, Flaviviridae, Filoviridae, Pneumoviridae and/or Coronaviridae viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator(s) of disease response. Further indicators include one or more overall quality of life health indicators, such as reduced illness duration, reduced illness severity, reduced time to return to normal health and normal activity, and reduced time to alleviation of one or more symptoms. In some embodiments, a compound of Formula (I), or a pharmaceutically acceptable salt thereof, can result in the reduction, alleviation or positive indication of one or more of the aforementioned indicators compared to a subject who is receiving the standard of care or an untreated subject.

In some embodiments, a compound of Formula (I), or a pharmaceutically acceptable salt thereof, can result in a reduction in the length and/or severity of one or more symptoms associated with a Picornaviridae, Flaviviridae, Filoviridae, Pneumoviridae and/or Coronaviridae viral infection compared to a subject who is receiving the standard of care or an untreated subject. Table 1 provides some embodiments of the percentage improvements obtained using a compound of Formula (I), or a pharmaceutically acceptable salt thereof, as compared to the standard of care or an untreated subject. Examples include the following: in some embodiments, a compound of Formula (I), or a pharmaceutically acceptable salt thereof, results in a percentage of non-responders that is 10% less than the percentage of non-responders receiving the standard of care; in some embodiments, a compound of Formula (I), or a pharmaceutically acceptable salt thereof, results in a duration of illness that is in the range of about 10% to about 30% less than compared to the duration of illness experienced by a subject who is untreated for the infection; and in some embodiments, a compound of Formula (I), or a pharmaceutically acceptable salt thereof, results in a severity of a symptom (such as one of those described herein) that is 25% less than compared to the severity of the same symptom experienced by a subject who is untreated for the infection. Methods of quantifying the severity of a side effect and/or symptom are known to those skilled in the art.

TABLE 1

| Percentage of non-responders | Percentage of relapsers | Percentage of resistance | Percentage of viral load rebound | Number of side effects | Severity of side effect(s) |
| --- | --- | --- | --- | --- | --- |
| 10% less | 10% less | 10% less | 10% less | 10% less | 10% less |
| 25% less | 25% less | 25% less | 25% less | 25% less | 25% less |
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |

TABLE 1-continued

| about 20% to about 80% less | about 20% to about 80% less | about 20% to about 80% less | about 20% to about 80% less | about 20% to about 80% less | about 20% to about 80% less |
|---|---|---|---|---|---|
| Duration of illness | Duration of illness | Duration of illness | Severity of symptom(s) | Severity of symptom(s) | Severity of symptom(s) |
| 10% less | 60% less | about 10% to about 30% less | 10% less | 60% less | about 10% to about 30% less |
| 25% less | 70% less | about 20% to about 50% less | 25% less | 70% less | about 20% to about 50% less |
| 40% less | 80% less | about 30% to about 70% less | 40% less | 80% less | about 30% to about 70% less |
| 50% less | 90% less | about 20% to about 80% less | 50% less | 90% less | about 20% to about 80% less |

As discussed above, in some embodiments, a compound of Formula (I), or a pharmaceutically acceptable salt thereof, is a panviral nucleoside analog. Various embodiments provide a panviral treatment that comprises a compound of Formula (I), or a pharmaceutically acceptable salt thereof. In this context, the term "panviral treatment" refers to a compound of Formula (I), or a pharmaceutically acceptable salt thereof, that is panviral as described above. Such panviral treatments are thus effective to treat two or more viral infections, where the viruses that cause the infections are caused by viruses from two or more virus families. For example, in an embodiment, the panviral treatment comprises a compound, or a pharmaceutically acceptable salt thereof, that is effective to treat viral infections caused by viruses in two or more families selected from the group consisting of Picornaviridae, Flaviviridae, Filoviridae, Pneumoviridae and Coronaviridae. Those skilled in the art are aware of numerous subfamilies, genera and species of viruses and the families in which they are categorized. For example, in an embodiment the panviral treatment comprises a compound, or a pharmaceutically acceptable salt thereof, that is effective to treat viral infections selected from a Rhinovirus infection in the Picornaviridae family; a Dengue virus infection or a Hepacivirus infection in the Flaviviridae family; an Ebolavirus infection in the Filoviridae family; a human respiratory syncytial virus (HRSV) infection in the Pneumoviridae family; and a human α-coronavirus viral infection and/or a human β-coronavirus viral infection in the Coronaviridae family. In various embodiments, the panviral treatment comprises a compound, or a pharmaceutically acceptable salt thereof, having low toxicity as described elsewhere herein. Examples of panviral treatments include those comprising compounds 1-15 as described in the Examples below, and pharmaceutically acceptable salts thereof.

In some embodiments, the compound can be a compound of Formula (I), wherein the compound of Formula (I) is a mono, di, or triphosphate, or a pharmaceutically acceptable salt of any of the foregoing. In still other embodiments, the compound can be a compound of Formula (I), wherein the compound of Formula (I) is a thiomonophosphate, alpha-thiodiphosphate, or alpha-thiotriphosphate, or a pharmaceutically acceptable salt of any of the foregoing. In some embodiments, the compound of Formula (I), or a pharmaceutical acceptable salt of any of the foregoing, that can be used to ameliorate and/or treat a Picornaviridae, Flaviviridae, Filoviridae, Pneumoviridae and/or Coronaviridae viral infection and/or inhibit replication of a Picornaviridae, Flaviviridae, Filoviridae, Pneumoviridae and/or Coronaviridae virus can be any of the embodiments described herein.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a picornavirus infection. In some embodiments, the total time of the treatment regime with a compound of Formula (I), or a pharmaceutically acceptable salt thereof, can be less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s) for treating, ameliorating and/or inhibiting a Picornaviridae, Flaviviridae, Filoviridae, Pneumoviridae and/or Coronaviridae viral infection.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) can result in an additive effect. In some embodiments, the combination of a compound of Formula (I), or a pharmaceutically acceptable salt thereof, used in combination with one or more additional agent(s) can result in a synergistic effect. In some embodiments, the combination of a compound of Formula (I), or a pharmaceutically acceptable salt thereof, used in combination with one or more additional agent(s) can result in a strongly synergistic effect. In some embodiments, the combination of a compound of Formula (I), or a pharmaceutically acceptable salt thereof, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) may be a reduction in the required amount(s) of one or more additional agent(s) that is effective in treating an a viral infection, as compared to the amount required to achieve same therapeutic result when one or more additional agent(s) are administered without a compound of Formula (I), or a pharmaceutically acceptable salt thereof. Another potential advantage of utilizing a compound of Formula (I), or a pharmaceutically acceptable salt thereof, in combination with one or more additional agent(s) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) may include little to no cross resistance between a compound of Formula (I), or a pharmaceutically acceptable salt thereof, and one or more additional agent(s) thereof; different routes for elimination of a compound of Formula (I), or a pharmaceutically acceptable salt thereof, and one or more additional agent(s); little to no overlapping toxicities between a compound of Formula (I), or a pharmaceutically acceptable salt thereof, and one or more additional agent(s); little to no significant effects on cytochrome P450; little to no pharmacokinetic interactions between a compound of Formula (I), or a pharmaceutically acceptable salt thereof, and one or more additional agent(s); greater percentage of subjects achieving a sustained viral response compared to when a compound is administered as monotherapy and/or a decrease in treatment time to achieve a sustained viral response compared to when a compound is administered as monotherapy.

For treating of a viral infection, examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, ribavirin and an interferon (including those described herein).

EXAMPLES

Additional embodiments are disclosed in further detail in the following examples, which are not in any way intended to limit the scope of the claims.

COMPOUNDS

Figure 2:
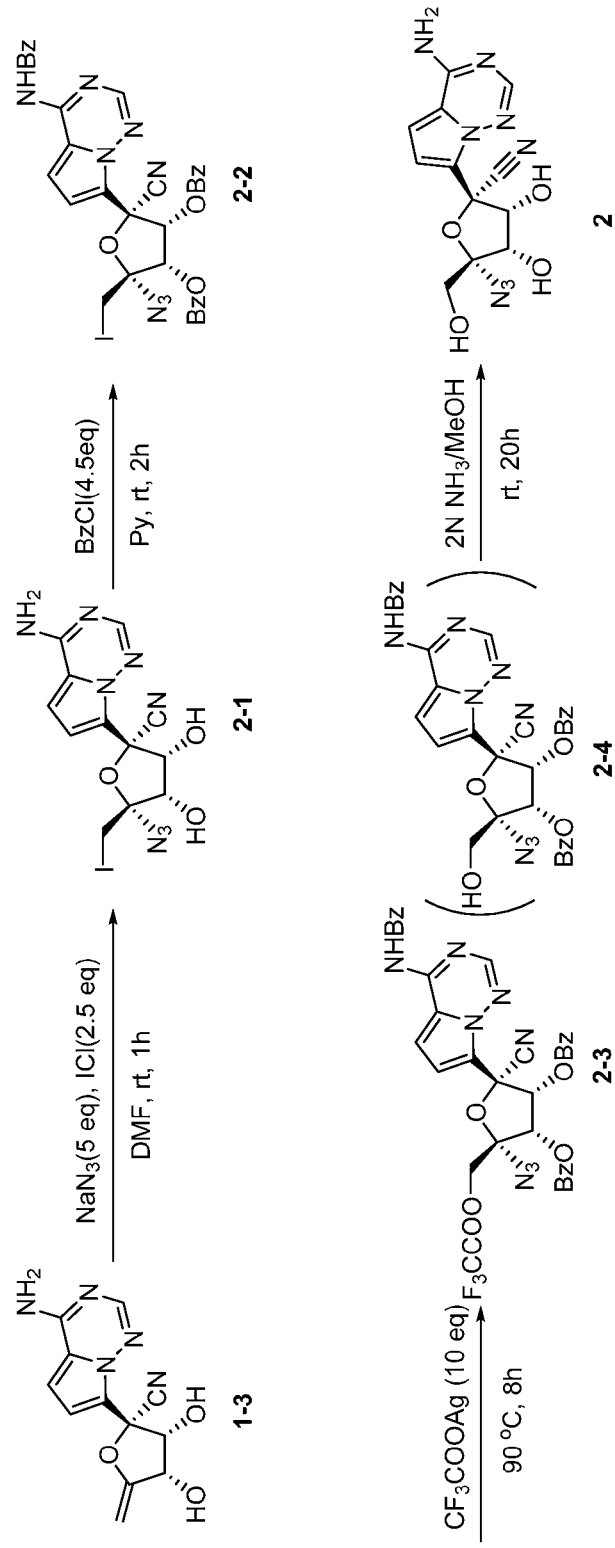
FIG. 2 illustrates a reaction scheme for making compound 2.
Figure 3:
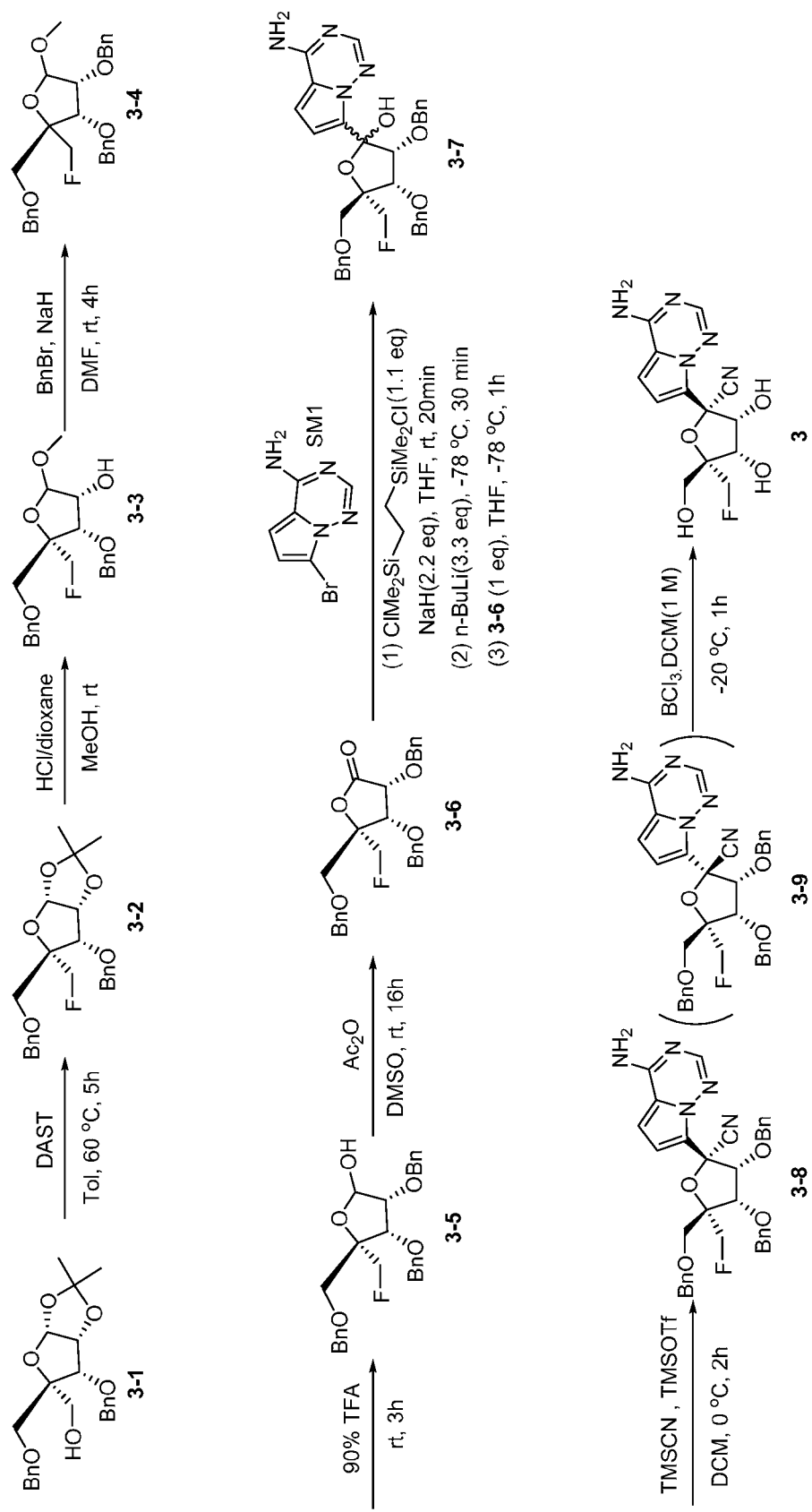
FIG. 3 illustrates a reaction scheme for making compound 3.
Figure 4:
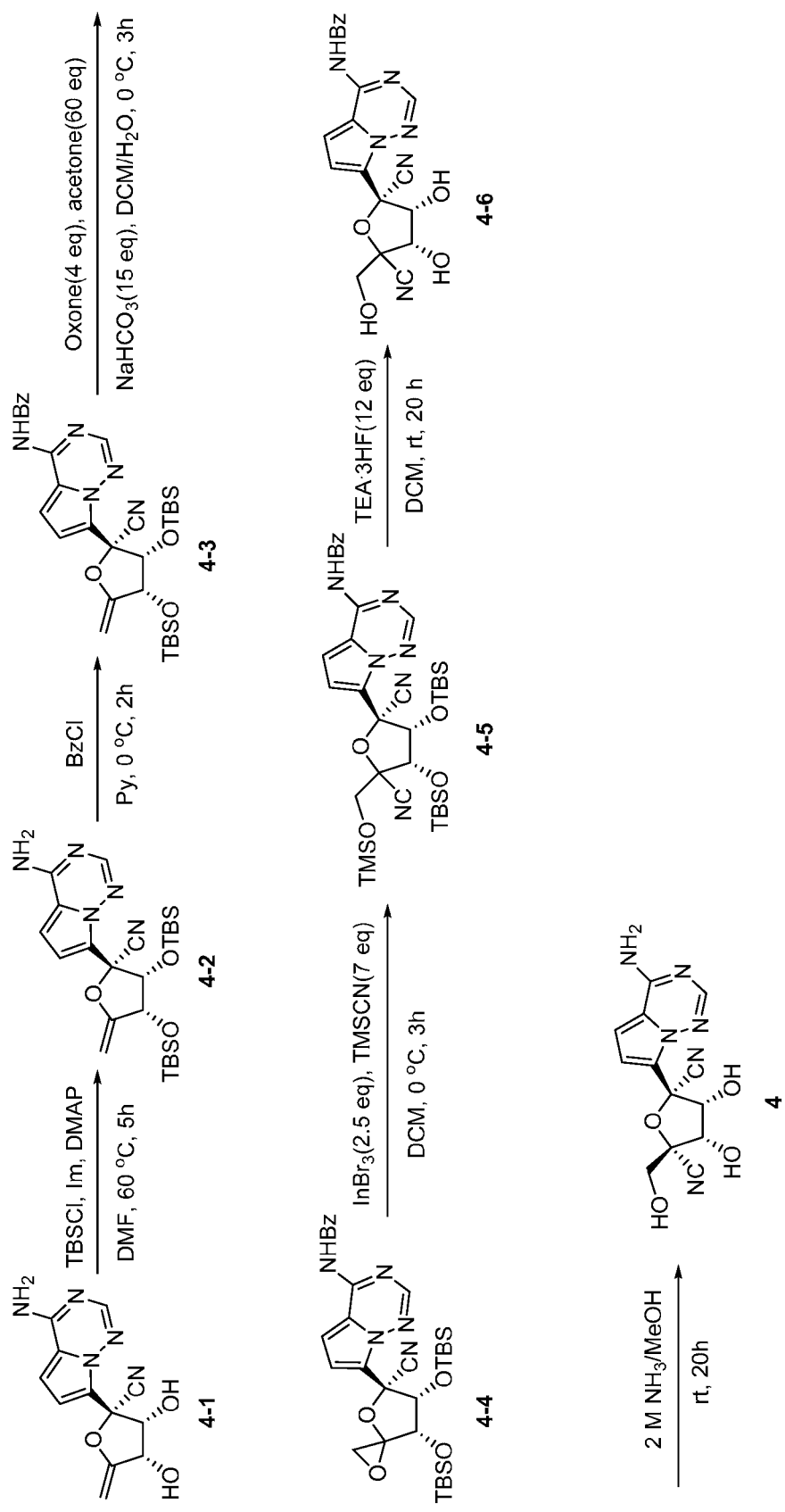
FIG. 4 illustrates a reaction scheme for making compound 4.
Figure 5:
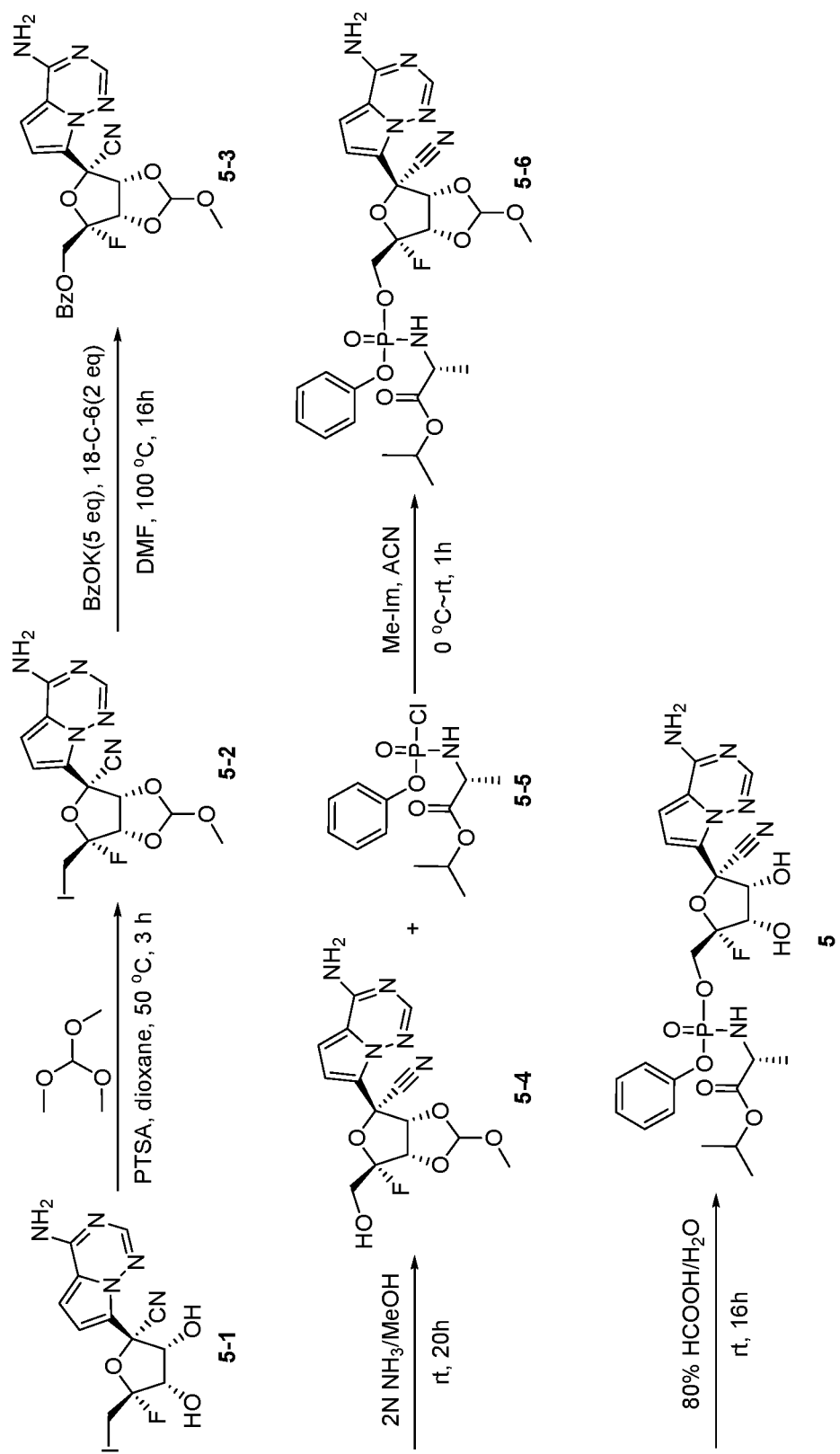
FIG. 5 illustrates a reaction scheme for making compound 5.
Figure 6:
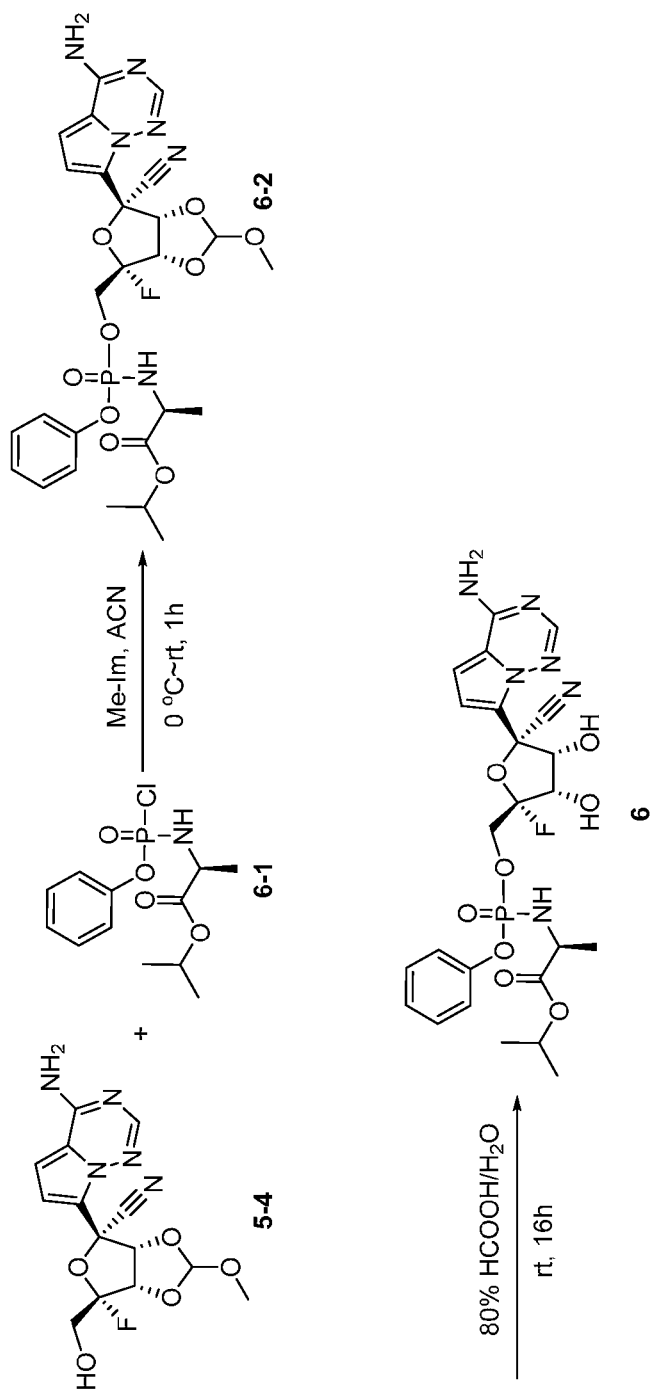
FIG. 6 illustrates a reaction scheme for making compound 6.
Figure 7:
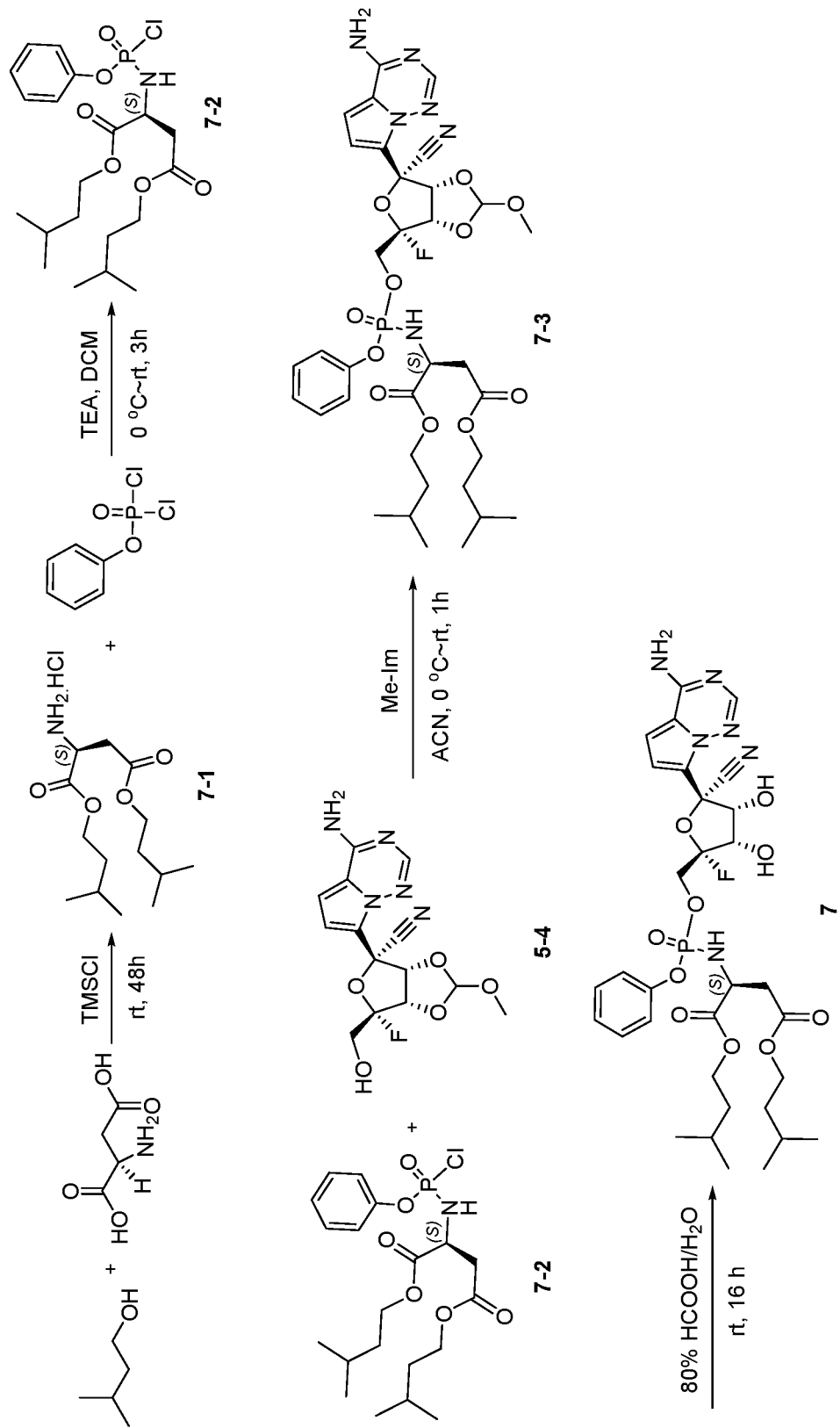
FIG. 7 illustrates a reaction scheme for making compound 7.
Figure 8:
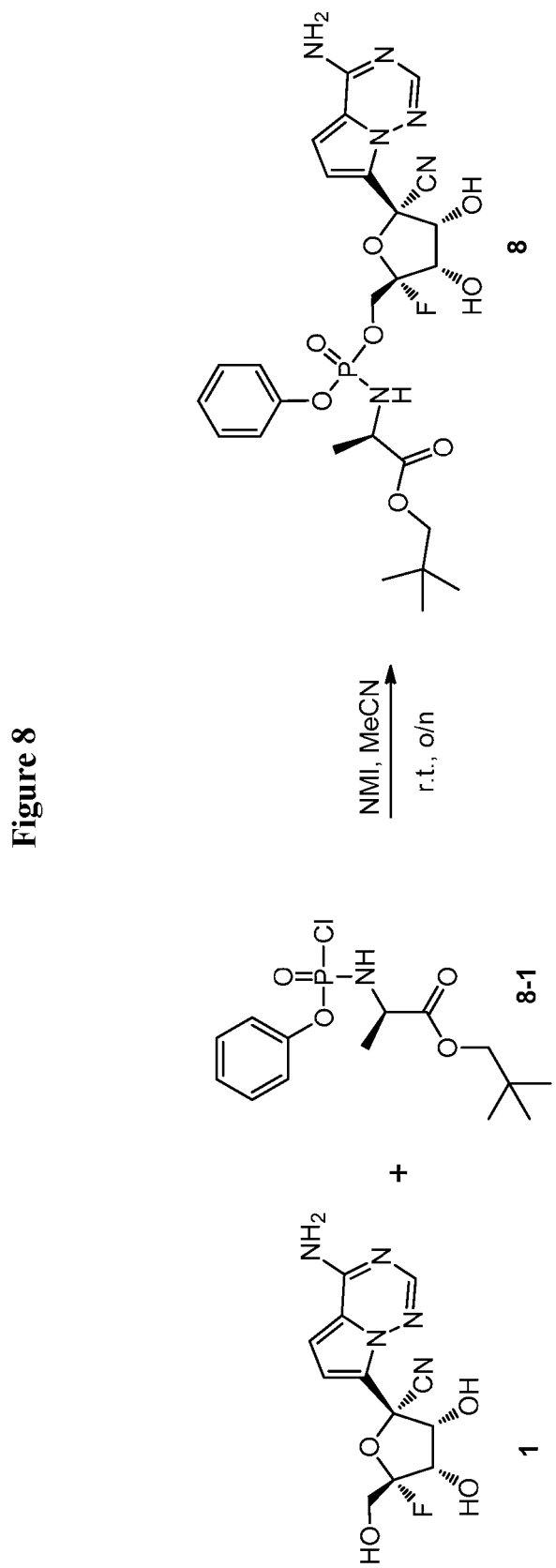
FIG. 8 illustrates a reaction scheme for making compound 8.

The compounds of Formula (I) illustrated in Tables 1-3 can be prepared in various ways, using techniques known to those skilled in the art as guided by the detailed teachings provided herein. For example, the compounds of Formula (I) illustrated in Tables 1-3 can be readily prepared in view of the detailed teachings set forth herein including Examples 1-15 below as well as the reaction schemes illustrated in FIGS. 1-8. Those skilled in the art will understand that a number of structures shown in Table 1-3 are stereospecific (or non-stereospecific) and/or are depicted as having unfilled valencies, and that isotopic and/or stereochemical variants, including racemates, diastereomers, enantiomers and/or deuterated versions, can be prepared in accordance with the guidance provided herein.

TABLE 1

| No. | Compound Structure |
|---|---|
| 1 | ![structure] |
| 2 | ![structure] |

TABLE 1-continued

| No. | Compound Structure |
|---|---|
| 3 | (structure: pyrrolo[2,1-f][1,2,4]triazin-7-yl nucleoside with HO, F (fluoromethyl), HO, OH, CN substituents) |
| 4 | (structure: pyrrolo[2,1-f][1,2,4]triazin-7-yl nucleoside with HO, NC, HO, OH, CN substituents) |

TABLE 1A

| No. | Compound Name |
|---|---|
| 1 | (2R,3R,4S,5S)-2-(4-Aminopyrrolo[2,1-f][1,2,4]triazin-7-yl)-5-fluoro-3,4-dihydroxy-5-(hydroxymethyl)tetrahydrofuran-2-carbonitrile |
| 2 | (2R,3R,4S,5R)-2-(4-Aminopyrrolo[2,1-f][1,2,4]triazin-7-yl)-5-azido-3,4-dihydroxy-5-(Hydroxymethyl)tetrahydrofuran-2-carbonitrile |
| 3 | (2R,3R,4S,5R)-2-(4-Aminopyrrolo[2,1-f][1,2,4]triazin-7-yl)-5-(fluoromethyl)-3,4-dihydroxy-5-(hydroxymethyl)tetrahydrofuran-2-carbonitrile |
| 4 | (2R,3R,4S,5R)-2-(4-Aminopyrrolo[2,1-f][1,2,4]triazin-7-yl)-3,4-dihydroxy-5-(hydroxymethyl)tetrahydrofuran-2,5-dicarbonitrile |

TABLE 2

| No. | Compound Structure |
|---|---|
| 5 | (phenoxy phosphoramidate prodrug with isopropyl ester of alanine, F-substituted nucleoside) |
| 6 | (phenoxy phosphoramidate prodrug with isopropyl ester of alanine, F-substituted nucleoside) |
| 7 | (S) (phenoxy phosphoramidate prodrug with diisoamyl aspartate, F-substituted nucleoside) |

TABLE 2-continued

| No. | Compound Structure |
|---|---|
| 8 | (phenoxy phosphoramidate prodrug with neopentyl ester of alanine, F-substituted nucleoside) |
| 9 | (phenoxy phosphoramidate prodrug with 2-ethylbutyl ester of alanine, F-substituted nucleoside) |
| 10 | (bis-phosphoramidate with propyl ester of alanine, F-substituted nucleoside) |
| 11 | (phenoxy phosphoramidate prodrug with isopropyl ester of alanine, azido-substituted nucleoside) |
| 12 | (triphosphate of F-substituted nucleoside) |
| 13 | (triphosphate of F-substituted nucleoside) |
| 14 | (triphosphate of azido-substituted nucleoside) |

TABLE 2A

| No. | Compound Name |
|---|---|
| 5 | Isopropyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-D-alaninate |
| 6 | Isopropyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-L-alaninate |
| 7 | Diisopentyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-L-aspartate |
| 8 | Neopentyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-L-alaninate |
| 9 | 2-Ethylbutyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-D-alaninate |
| 11 | Isopropyl ((((2R,3S,4R,5R)-5-(4-aminopyrrolo[2,1-f][1,2,4]triazin-7-yl)-2-azido-5-cyano-3,4-dihydroxytetrahydrofuran-2-yl)methoxy)(phenoxy)phosphoryl)-D-alaninate |
| 12 | ((2S,3S,4R,5R)-5-(4-Aminopyrrolo[2,1-f][1,2,4]triazin-7-yl)-5-cyano-2-fluoro-3,4-dihydroxytetrahydrofuran-2-yl)methyl tetrahydrogen triphosphate |
| 13 | ((2R,3S,4R,5R)-5-(4-Aminopyrrolo[2,1-f][1,2,4]triazin-7-yl)-5-cyano-2-(fluoromethyl)-3,4-dihydroxytetrahydrofuran-2-yl)methyl tetrahydrogen triphosphate |
| 14 | ((2R,3S,4R,5R)-5-(4-Aminopyrrolo[2,1-f][1,2,4]triazin-7-yl)-2-azido-5-cyano-3,4-dihydroxytetrahydrofuran-2-yl)methyl tetrahydrogen triphosphate |

TABLE 3

| No. | Compound Structure |
|---|---|
| 15 | (structure: (2R,3R,4S,5R)-2-(4-Aminopyrrolo[2,1-f][1,2,4]triazin-7-yl)-5-(chloromethyl)-3,4-dihydroxy-5-(hydroxymethyl)tetrahydrofuran-2-carbonitrile) |

TABLE 3A

| No. | Compound Name |
|---|---|
| 15 | (2R,3R,4S,5R)-2-(4-Aminopyrrolo[2,1-f][1,2,4]triazin-7-yl)-5-(chloromethyl)-3,4-dihydroxy-5-(hydroxymethyl)tetrahydrofuran-2-carbonitrile |

Synthesis

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent. Abbreviations and acronyms used herein include those used in Table 4.

TABLE 4

| Term | Acronym |
|---|---|
| Acetonitrile | ACN |
| Aqueous | aq |
| Atmosphere | atm |
| Broad | br |
| Diatomaceous Earth | Celite ® |
| 1,8-Diazabicyclo[5.4.0]undec-7-ene | DBU |
| Dichloromethane | DCM |
| Diisopropylethylamine | DIPEA, DIEA, or Hunig's base |
| 4-Dimethylaminopyridine | DMAP |
| N,N-Dimethylformamide | DMF |
| Dimethylsulfoxide | DMSO |
| Diethyl ether | Ether, $Et_2O$ |
| Ethyl Acetate | EtOAc, or EA |
| Ethanol | EtOH |
| Normal-phase silica gel chromatography | FCC |
| Grams | g |
| Hours | h |
| High-pressure liquid chromatography | HPLC |
| Hertz | Hz |
| Liquid chromatography and mass spectrometry | LCMS |
| Molar | M |
| Mass to charge ratio | m/z |
| Methanol | MeOH |
| Milligrams | mg |
| Minute | min |
| Milliliter | mL |
| Microliter | μL |
| Millimoles | mmol |
| Mass spectrometry | MS |
| Normal | N |
| N-Iodosuccinimide | NIS |
| Nuclear magnetic resonance | NMR |
| $CF_3SO_3$— or triflate | OTf |
| Parts per million | ppm |
| Retention time | $R_t$ |
| Room temperature | rt |
| Saturated | sat |
| Temperature | T |
| Triethylamine | TEA |
| Trifluoroacetic acid | TFA |

TABLE 4-continued

| Term | Acronym |
|---|---|
| Tetrahydrofuran | THF |
| Thin layer chromatography | TLC |
| Volume in milliliters of solvent per gram of substrate | V, or volumes |

Exemplary compounds useful in methods of the invention will now be described by reference to the illustrative synthetic schemes for their general preparation below and the specific examples to follow.

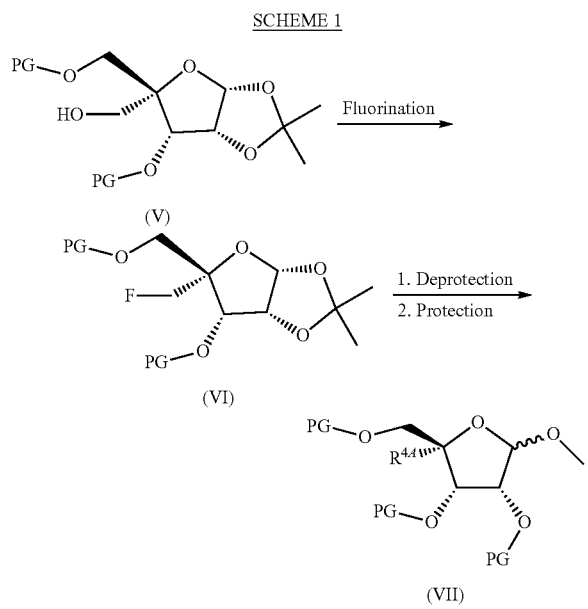

According to SCHEME 1, fluorination of a compound of formula (V), where PG is benzyl, is achieved using a fluorinating agent such as diethylaminosulfur trifluoride (DAST), and the like, in a suitable solvent such as toluene, DCM, and the like, at temperatures ranging from 0 OC to 60° C. A compound of formula (VII), is prepared in two steps from a compound of formula (VI) where PG is benzyl. Acid-catalyzed hydrolysis of the 1,2-acetonide with HCl in a dioxane-methanol mixture followed by reaction with NaH and benzyl bromide provides a compound of formula (VII), where PG is benzyl and $R^{4,4}$ is $CH_2F$.

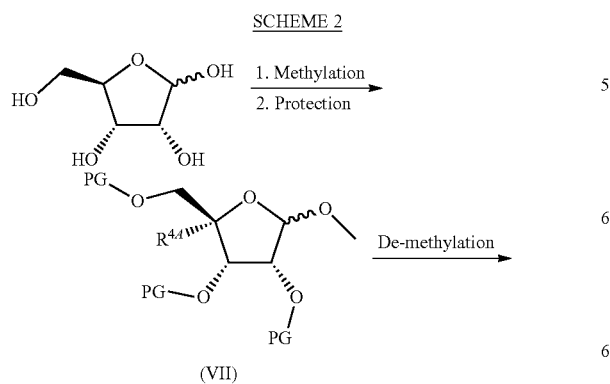

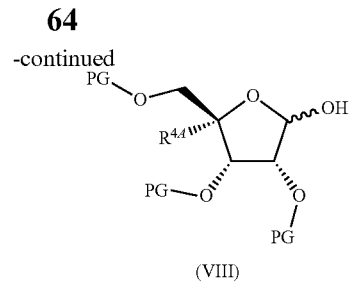

According to SCHEME 2, a compound of formula (VII), where PG is benzyl and $R^{4,4}$ is H, is prepared from D-ribofuranose in two steps. In a first step, D-ribofuranose is methylated employing an acid such as $H_2SO_4$, in MeOH. In a second step, protection with a suitable protecting group such as benzyl, employing conditions known to one skilled in the art, provides a compound of formula (VII). Removal of the methyl group in a compound of formula (VII), where $R^{4,4}$ is H is accomplished using an acid such a TFA, and the like, in water, for a period of 10-15 h, to provide a compound of formula (VIII), where PG is benzyl. Where $R^{4,4}$ is $CH_2F$, the process of Scheme 2 can be modified as indicated in Scheme 2A.

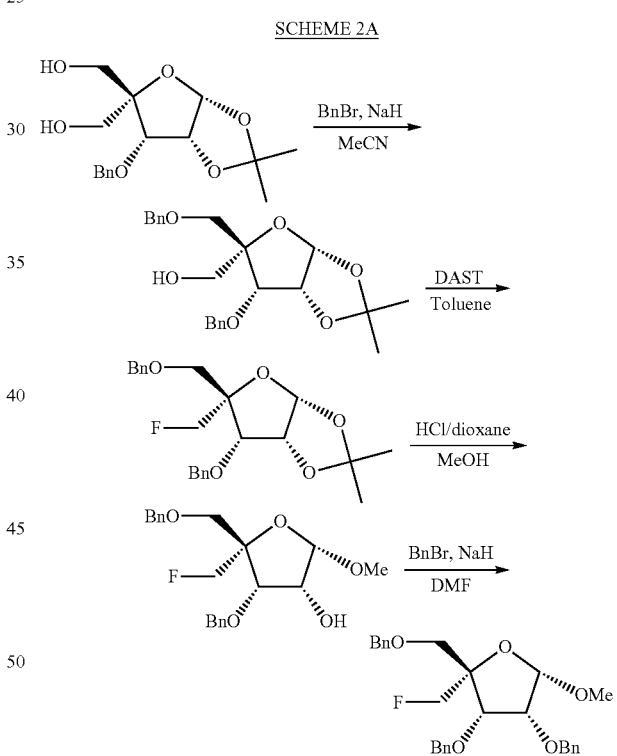

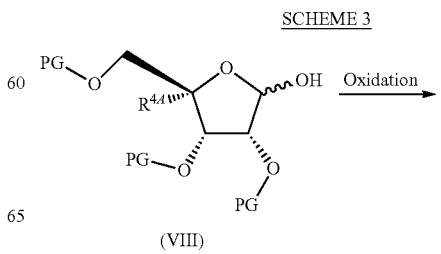

-continued

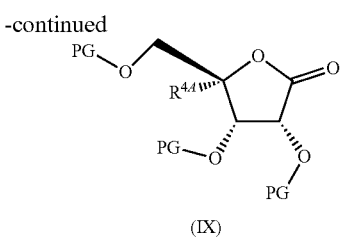

(IX)

According to SCHEME 3, a compound of formula (VIII) where PG is benzyl and $R^{4.4}$ is H or $CH_2F$, is oxidized employing chromium-mediated oxidation such as PCC, or $DMSO/Ac_2O$, to provide a ribolactone compound of formula (IX).

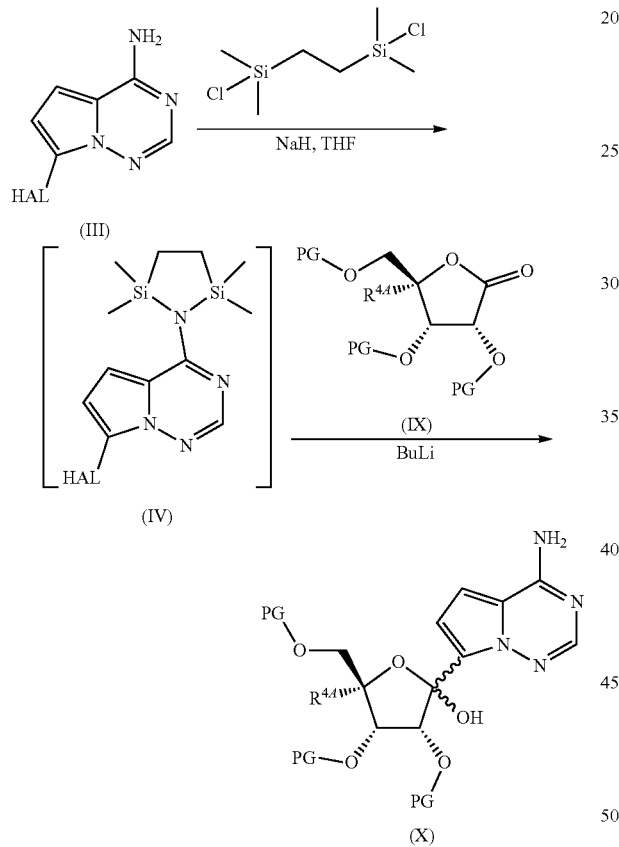

According to SCHEME 4, a compound of formula (X) is prepared in two steps from a commercially available or synthetically accessible compound of formula (III), where HAL is Br, and a commercially available or synthetically accessible compound of formula (IX), where PG is benzyl, and $R^{4.4}$ is H or $CH_2F$. For example, in a first step, a compound of formula (III) such as 7-bromopyrrolo[2,1-f][1,2,4]triazin-4-amine is reacted with a base such as NaH and the like, in a suitable solvent such as THF, and the like, and 1,2-bis(chlorodimethylsilyl)ethane to provide a compound of formula (IV) which was not isolated but used directly in the next step. In a second step, a compound of formula (IV) is reacted with a base such as n-BuLi, t-BuLi, and the like, in a suitable solvent such as THF, $Et_2O$, and the like, at a temperature of −78° C., followed by the addition of a commercially available or synthetically accessible ribolactone compound of formula (IX) such as (3R,4S,5R)-3,4-bis(benzyloxy)-5-((benzyloxy)methyl)-5-(fluoromethyl)dihydrofuran-2(3H)-one, (3R,4R,5R)-3,4-bis(benzyloxy)-5-((benzyloxy)methyl)dihydrofuran-2(3H)-one, and the like, to provide a compound of formula (X).

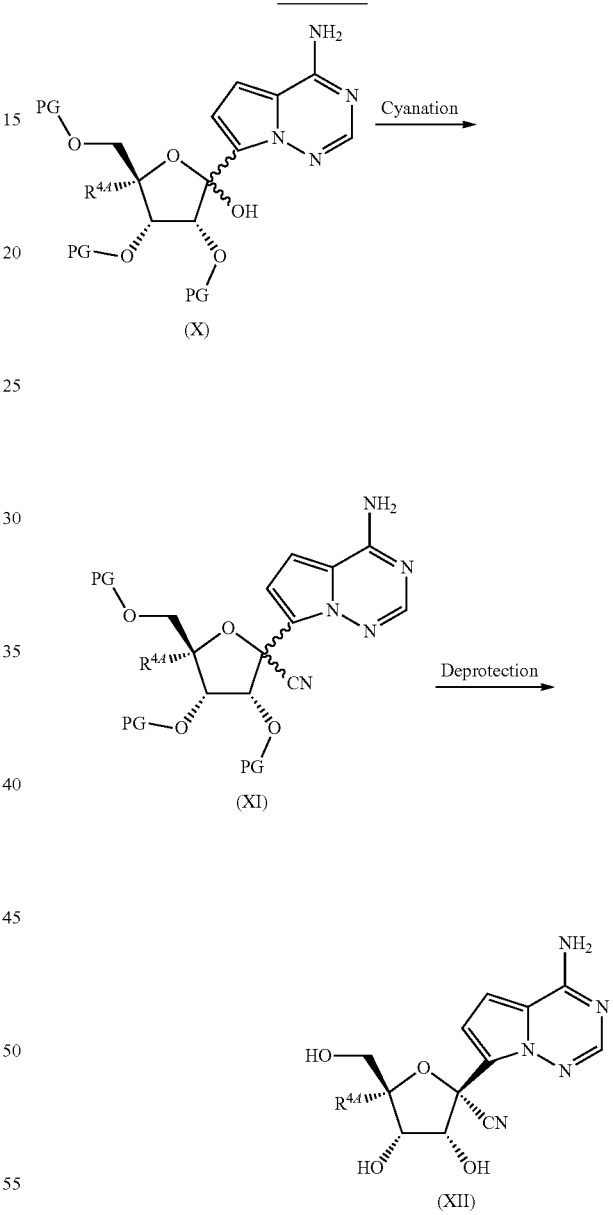

According to SCHEME 5, a cyano compound of formula (XI), where $R^{4.4}$ is H and PG is benzyl, is prepared from a compound of formula (X). For example, a compound of formula (X) is reacted with TMSCN and TMSOTf in a solvent such as DCM, and the like, at a temperature of about −78° C., to provide a compound of formula (XI). Removal of the three benzyl protecting groups is achieved with a reagent such as boron trichloride to provide a compound of formula (XII), where $R^{1.4}$ is CN and $R^{4.4}$ is H.

SCHEME 6

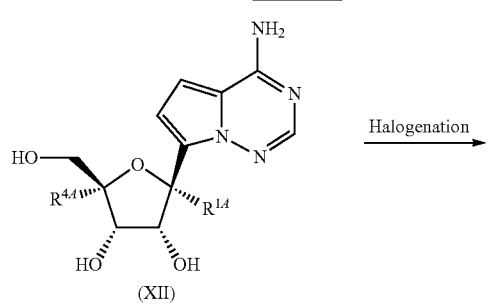

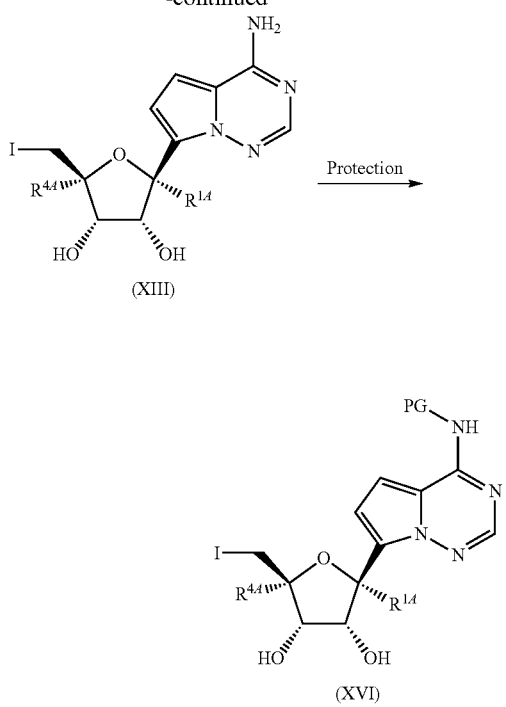

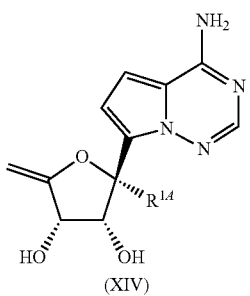

According to SCHEME 6, a compound of formula (XII) where $R^{4A}$ is H, $R^{1A}$ is CN, is halogenated employing triphenylphosphine, imidazole and iodine, to provide a compound of formula (XIII). An iodo compound of formula (XIII) undergoes a base promoted elimination to provide an olefin compound of formula (XIV).

According to SCHEME 7, treatment of an olefin compound of formula (XIV), where $R^{1A}$ is CN, is halogenated with N-iodosuccinimide (NIS) and TEA-3HF, in a suitable solvent such as ACN, to provide a fluoro iodo compound of formula (XIII), where $R^{1A}$ is CN, $R^{4A}$ is F.

An azide compound of formula (XIII), where $R^{4A}$ is $N_3$, is prepared by the addition of iodine azide to the 4'-double bond of a compound of formula (XIV) in a regio and stereospecific manner. For example, iodine azide (generated in situ from iodine monochloride and sodium azide) is added to a compound of formula (XIV), where $R^{1A}$ is CN, in a solvent suitable such as DMF, to provide an azide compound of formula (XIII), where $R^{4A}$ is $N_3$ and $R^{1A}$ is CN.

Protection, employing benzoyl chloride, in a solvent such as pyridine, at temperatures ranging from 0° C. to room temperature, affords a compound of formula (XVI), where $R^{1A}$ is CN, $R^{4A}$ is $N_3$ or F, and PG is benzoyl.

SCHEME 7

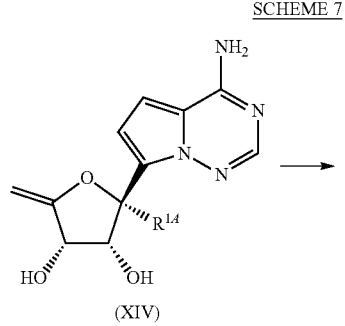

SCHEME 8

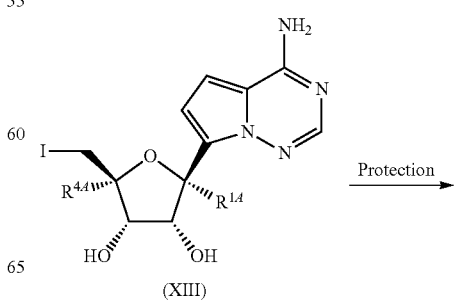

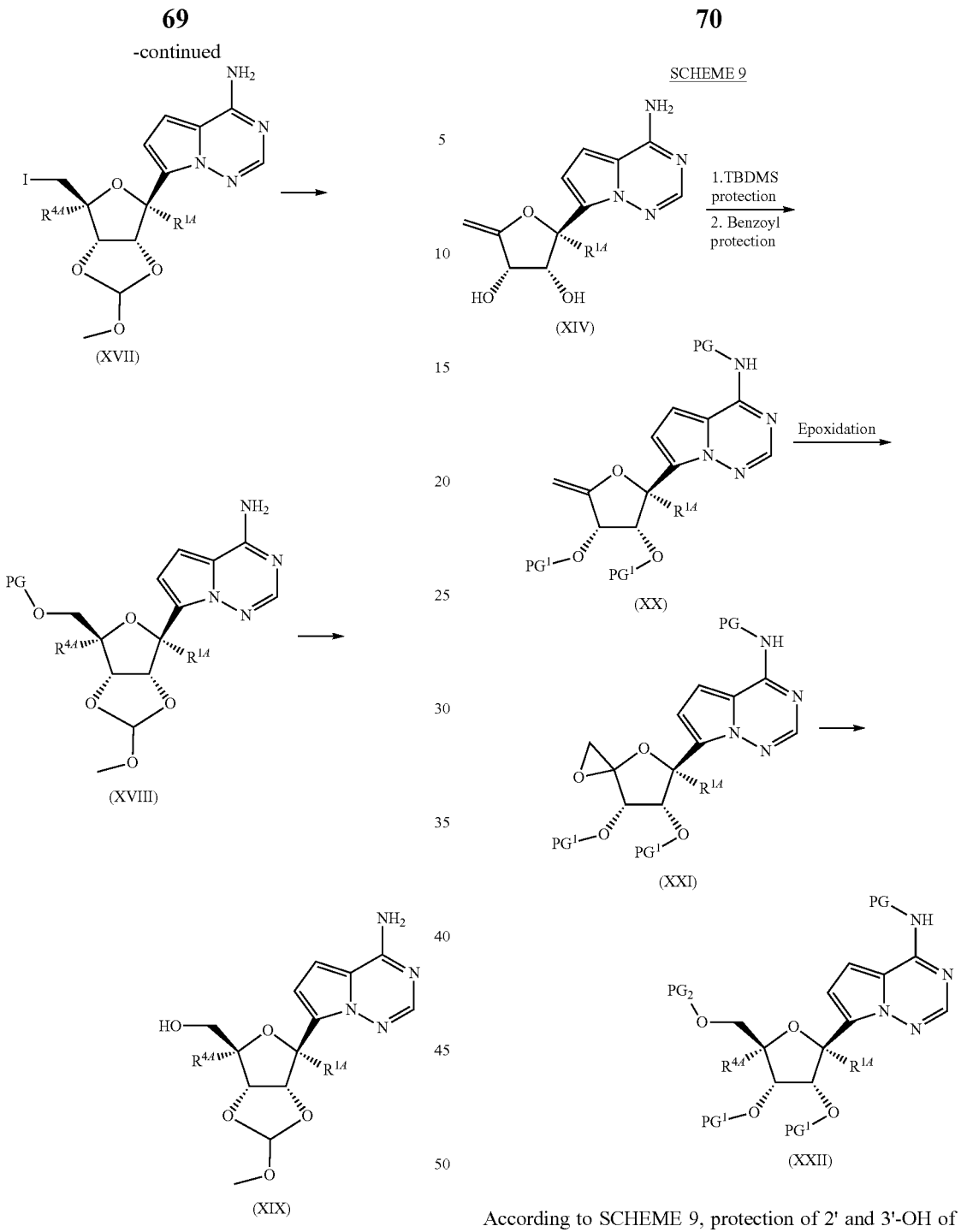

According to SCHEME 8, a compound of formula (XIII), where $R^{1A}$ is CN and $R^{4A}$ is F, is protected to provide an methoxymethylene compound of formula (XVII). Reaction of a compound of formula (XVII) in a nucleophilic substitution reaction with a nucleophile such as potassium benzoate, and the like, 18-crown-6, in a suitable solvent such as DMSO, DMF, and the like, at a temperature of about 100° C., provides a compound of formula (XVIII), where PG is benzoyl. Deprotection of the benzoyl protecting group (PG) with ammonia in methanol provides a compound of formula (XIX), where $R^{1A}$ is CN and $R^{4A}$ is F.

According to SCHEME 9, protection of 2' and 3'-OH of a compound of formula (XIV), where $R^{1A}$ is CN, with tert-butyl dimethylsilyl groups is achieved employing tert-butyl(chloro)dimethylsilane, in the presence of imidazole and DMAP, in a suitable solvent such as DMF, and the like, at a temperature of about 40-60° C. Subsequent benzoyl protection, employing conditions previously described provides a compound of formula (XX), where each $PG^1$ is TBDMS, and PG is Bz. Stereoselective epoxidation with a dioxirane such as dimethyldioxirane (DMDO, generated in situ by adding acetone to an aqueous solution containing potassium peroxymonosulfate (Oxone)), in a suitable solvent such as DCM, affords an epoxide compound of formula (XXI). A compound of formula (XXII), where $R^{1A}$ and $R^{4A}$ are CN, and $PG^2$ is trimethylsilyl, is prepared by ring opening of the epoxide of a compound of formula (XXI) in the presence of a Lewis Acid such as InBr$_3$, TiCl$_4$, and the like, and cyanotrimethylsilane (TMSCN), in a suitable solvent such as DCM, and the like.

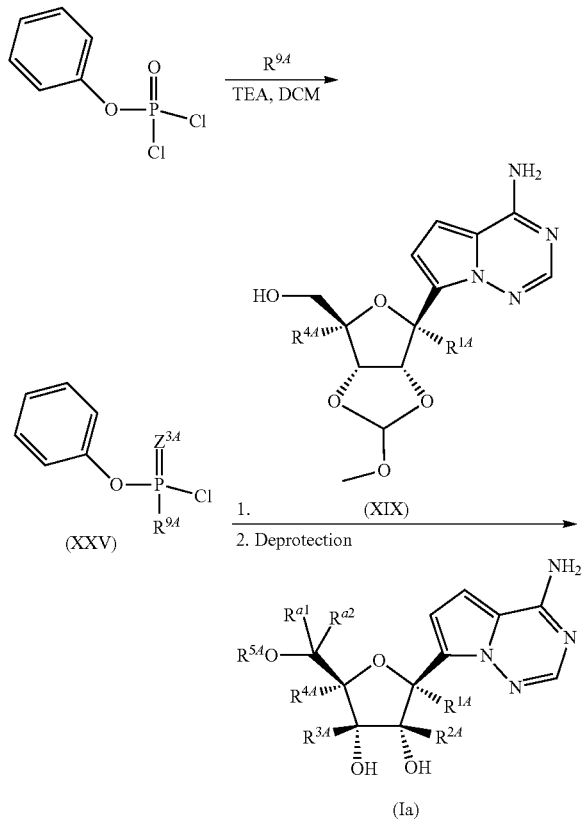

SCHEME 10

According to SCHEME 10, a chlorophosphoramidate of formula (XXV), where $Z^{3A}$ is O, and $R^{9A}$ is an N-linked amino acid or an optionally substituted N-linked amino acid ester derivative, is prepared by reacting phenyl phosphorodichloridate with a commercially available or synthetically accessible amino acid or an optionally substituted amino acid ester derivative, a base such as triethylamine (TEA), and the like, in a suitable solvent such as DCM. Employing the Uchiyama procedure (Uchiyama, M.; Aso, Y.; Noyori, R.; Hayakawa, Y. O-selective phosphorylation of nucleosides without N-protection. J. Org. Chem. 1993, 58, 373-379), a chlorophosphoramidate compound of formula (XXV) is reacted with a compound of formula (XIX), where $R^{1A}$ is CN and $R^{4A}$ is F, in the presence of N-methylimidazole, in a suitable solvent such as ACN. Subsequent deprotection of the tethered oxomethylene is accomplished employing an acid such as HCl, HCOOH, and the like, in a suitable solvent such as dioxane, water, or a mixture thereof, to provide a compound of Formula (Ia), where $R^{1A}$ is CN, $R^{2A}$ and $R^{3A}$ are H, and $R^{4A}$ is F.

Compounds of Formula (I) may be converted to their corresponding salts using methods known to one of ordinary skill in the art. For example, an amine of Formula (I) is treated with trifluoroacetic acid, HCl, or citric acid in a solvent such as Et$_2$O, CH$_2$Cl$_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds described herein have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The specific examples described below are provided to further illustrate the invention and various preferred embodiments. In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Normal-phase silica gel chromatography (FCC) was performed on silica gel (SiO$_2$) using prepacked cartridges.

Preparative reverse-phase high performance liquid chromatography (RP HPLC) was performed on an Agilent HPLC with an Xterra Prep RP18 column (5 µM, 30×100 or 50×150 mm) or an XBridge C18 OBD column (5 µM, 30×100 or 50×150 mm), and a mobile phase of 5% ACN in 20 mM NH$_4$OH was held for 2 min, then a gradient of 5-99% ACN over 15 min, then held at 99% ACN for 5 min, with a flow rate of 40 or 80 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker 400 MHz model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Intermediate 1

(2R,3R,4S,5R)-2-(4-Aminopyrrolo[2,1-f][1,2,4]triazin-7-yl)-3,4-dihydroxy-5-(hydroxymethyl)tetrahydrofuran-2-carbonitrile

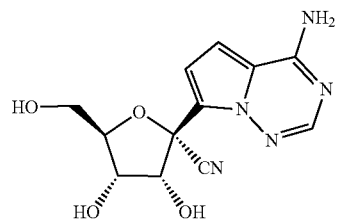 [SMILES: N#C[C@@]1(c2ccc3c(N)ncnn23)O[C@H](CO)[C@@H](O)[C@H]1O]

Step A. 7-Bromopyrrolo[2,1-f][1,2,4]triazin-4-amine

To a solution of pyrrolo[2,1-f][1,2,4]triazin-4-amine (2.1 g, 15.66 mmol, 1.00 equiv) in DMF (20 mL) was added 1,3-dibromo-5,5-dimethylimidazolidine-2,4-dione (2.24 g, 7.83 mmol, 0.53 equiv) at −20° C. in batches. The resulting solution was stirred for 1 h at −20° C., then quenched by the addition of 30 mL of sat. sodium sulfite (aq). After filtration, the filter was dissolved in 200 ml of ethyl acetate, washed with 100 mL of sat. sodium carbonate (aq.), dried over sodium sulfate and concentrated under reduced pressure. This resulted in 2.50 g (75%) of the title compound as a white solid. MS m/z [M+H]⁺ (ESI): 213, 215.

Step B. (3R,4R,5R)-2-(4-Aminopyrrolo[2,1-f][1,2,4]triazin-7-yl)-3,4-bis(benzloxy)-5-((benzyloxy)methyl)tetrahydrofuran-2-ol To a solution of 7-bromopyrrolo[2,1-f][1,2,4]triazin-4-amine (2 g, 9.39 mmol, 2.98 equiv) in anhydrous THF (200 mL) under inert atmosphere, was added 1,1,4,4-tetramethyl-1,4-dichlorodisilyethylene(2.2 g, 9.46 mmol, 1.1 equiv) along with sodium hydride (754 mg, 18.92 mmol, 2.2 equiv) and the mixture was stirred for 20 min at room temperature. The reaction was then cooled to −78° C. before n-butyllithium (11.4 mL, 28.38 mmol, 2.5 M in hexanes) was added slowly over 10 min. The reaction was allowed to stir for a further 15 min before (3R,4 R, 5R)-3,4-bis(benzyloxy)-5-[(benzyloxy)methyl]oxolan-2-one (3.6 g, 8.60 mmol, 1.00 equiv) (dissolved in 5 mL THF) was added dropwise. The resulting solution was stirred for 1 h at −78° C., then quenched by the addition of 200 mL sat. ammonium chloride (aq.). The resulting solution was extracted with of ethyl acetate (200 mL×3) and the organic layers combined, dried over sodium sulfate and concentrated under reduced pressure. The crude product was purified by reverse phase flash chromatography (ACN/H₂O). This resulted in 2 g (42%) of the title compound as a yellow solid. MS m/z [M+H]⁺ (ESI):553.

Step C. (3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile To a solution of (3R,4R,5R)-2-(4-aminopyrrolo[2,1-f][1,2,4]triazin-7-yl)-3,4-bis(benzyloxy)-5-((benzyloxy)methyl) tetrahydrofuran-2-ol (2.2 g, 3.98 mmol, 1.00 equiv) in DCM (80 mL) under inert atmosphere, was added trimethylsilanecarbonitrile (1.86 mL, 3.50 equiv) dropwise at 0° C. The resulting solution was stirred for 10 min. To this was added trimethylsilyl trifluoromethanesulfonate (3.26 mL, 4.50 equiv) dropwise at 0° C. The resulting solution was stirred for 2 h at 0° C. then quenched by the addition of 200 mL of sat. sodium bicarbonate (aq.). The resulting solution was extracted with 200 mL of DCM and the organic layers combined and dried over anhydrous sodium sulfate and concentrated under reduced pressure. The residue was purified on silica gel column with ethyl acetate/petroleum ether (1:10-2:1). This resulted in 1.2 g (54%) of the title compound as a yellow solid. MS m/z [M+H]⁺ (ESI): 562.

Step D. (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile To a solution of (3R,4R,5R)-2-(4-aminopyrrolo[2,1-f][1,2,4]triazin-7-yl)-3,4-bis(benzyloxy)-5-((benzyloxy)methyl) tetrahydrofuran-2-carbonitrile (1 g, 1.78 mmol, 1.00 equiv) in DCM (5 mL) under inert atmosphere, was added a solution of boron trichloride (1M in DCM, 8 mL, 3.4 eq) dropwise at 0° C. The resulting solution was stirred for 1 h at 0° C., then quenched by the addition of potassium carbonate in methanol. After filtration, the resulting solution was concentrated under reduced pressure. The crude product was purified by reverse phase flash chromatography (ACN/H₂O). This resulted in 207 mg (40%) of the title compound as a white solid. MS m/z [M+H]⁺ (ESI): 292. ¹H-NMR (DMSO-d₆): δ 7.90 (s, 1H), 7.6-8.0 (br, 2H), 6.88 (d, J=4.4 Hz, 1H), 6.86 (d, J=4.4 Hz, 1H), 6.1 (br s, 1H), 5.19 (br s, 1H), 4.91 (br s, 1H), 4.62 (d, J=5.2 Hz, 1H), 4.04 (m, 1H), 3.93 (m, 1H), 3.62 (m, 1H), 3.49 (m, 1H).

Intermediate 2

(3R,4S,5R)-3,4-Bis(benzyloxy)-5-((benzyloxy)methyl)-5-(fluoromethyl)dihydrofuran-2(3H)-one

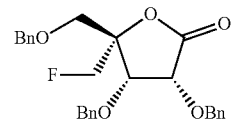

Step A. (3aR,5R,6S,6aR)-6-(Benzyloxy)-5-((benzyloxy)methyl)-5-(fluoromethyl)-2,2-dimethyltetrahydrofuro[2,3-d][1,3]dioxole To a solution of diethylaminosulfur trifluoride (DAST) (16 g, 99.38 mmol, 1.99 equiv) in toluene (200 mL) under inert atmosphere, was added a solution of ((3aR,5R,6S,6aR)-6-(benzyloxy)-5-((benzyloxy)methyl)-2,2-dimethyl-tetrahydrofuro[2,3-d][1,3]dioxol-5-yl)methanol (20 g, 49.94 mmol, 1.00 equiv) in toluene (100 mL) dropwise with stirring at 0° C. The resulting solution was stirred for 5 h at 60° C. The reaction was quenched by the addition of aq. NaHCO₃(3 L), and extracted with EtOAc (3×200 mL). The organic layers were combined and dried over anhydrous sodium sulfate, filtered and concentrated under reduced pressure. Purification on silica gel column with ethyl acetate/petroleum ether (1:20)) afforded 12.5 g (62%) of the title compound as yellow oil. MS m/z: 403 [M+H]+.

Step B. (3R,4S,5R)-4-(Benzyloxy)-5-((benzyloxy)methyl)-5-(fluoromethyl)-2-methoxytetrahydrofuran-3-ol To a solution of (3aR,5R,6S,6aR)-6-(benzyloxy)-5-((benzyloxy)methyl)-5-(fluoromethyl)-2,2-dimethyltetrahydrofuro[2,3-d][1,3]dioxole (10 g, 24.8 mmol, 1.00 equiv) in methanol (100 mL) was added a solution of hydrogen chloride (4M in 1,4-dioxane, 30 mL) at 0° C. The resulting solution was stirred for 1 h at 25° C., and concentrated under reduced pressure to provide 9 g (crude) of the title compound as yellow oil, which was used directly in the next step without purification. MS m/z: 377 [M+H]+.

Step C. (2R,3S,4R)-3,4-Bis(benzyloxy)-2-((benzyloxy)methyl)-2-(fluoromethyl)-5-methoxytetrahydrofuran To a solution of (3R,4S,5R)-4-(benzyloxy)-5-((benzyloxy)methyl)-5-(fluoromethyl)-2-methoxytetrahydrofuran-3-ol (20 g, 53.13 mmol, 1.00 equiv) in tetrahydrofuran (400 mL) under inert atmosphere, was added sodium hydride (4.3 g, 179.17 mmol, 2.10 equiv) at 0° C. in batches and stirred for 0.5 h. To the resulting solution was added benzyl bromide (18 g, 105.88 mmol, 2.00 equiv) and stirred for 4 h at 25° C. The reaction was then quenched by the addition of NH4C1 aq. (200 mL), and extracted with EtOAc (2×500 mL). The organic layers were combined, washed with NaCl aq. (500 mL), dried over anhydrous sodium sulfate, and concentrated under reduced pressure to afford 15 g (crude) of the title compound as yellow oil, which was used directly in next step without purification. MS m/z: 489 [M+H]+.

Step D. (3R,4S,5R)-3,4-Bis(benzyloxy)-5-((benzyloxy)methyl)-5-(fluoromethyl) tetrahydrofuran-2-ol A solution of (2R,3S,4R)-3,4-bis(benzyloxy)-2-((benzyloxy)methyl)-2-(fluoromethyl)-5-methoxytetrahydrofuran (11 g, 38.58 mmol, 1.00 equiv) in 90% TFA in water (200 mL) was stirred for 3 h at 25° C. The resulting mixture was concentrated under reduced pressure. Residue was dissolved in EtOAc and washed with sodium chloride aq. (500 mL), and dried over anhydrous sodium sulfate. Purification of the evaporated residue (silica gel column with ethyl acetate/petroleum ether (1/3)) afforded 8.9 g (46%) of the title compound as yellow oil. MS m/z: 475 [M+H]+.

Step E. (3R,4S,5R)-3,4-Bis(benzyloxy)-5-((benzyloxy)methyl)-5-(fluoromethyl) dihydrofuran-2(3H)-one To a solution of (3R,4S,5R)-3,4-bis(benzyloxy)-5-((benzyloxy)methyl)-5-(fluoromethyl)tetrahydrofuran-2-ol (1 g, 2.21 mmol, 1.00 equiv) in DMSO (20 mL), was added Ac2O (15 mL). The resulting solution was stirred for 16 h at room temperature. The reaction was then quenched by the addition aq. Na2CO3 (50 mL), and extracted with ethyl acetate (3×50 mL). The organic layers were combined and dried over anhydrous sodium sulfate, filtered and concentrated under reduced pressure. Purification (silica gel column with ethyl acetate/petroleum ether (1:5)) afforded 578 mg (58%) of the title compound as yellow oil. MS m/z: 473 [M+H]+.

Intermediate 3

(3R,4S,5R)-5-(chloromethyl)-3,4-dihydroxy-5-(hydroxymethyl)dihydrofuran-2(3H)-one

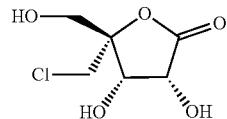

The title compound may be prepared in a manner analogous to Intermediate 2, Steps A-E, with the modification of replacing DAST with PPh3, CCl4, DCE, higher temperature, in Step A.

Example 1

Compound 1: (2R,3R,4S,5S)-2-(4-Aminopyrrolo[2,1-f][1,2,4]triazin-7-yl)-5-fluoro-3,4-dihydroxy-5-(hydroxymethyl)tetrahydrofuran-2-carbonitrile

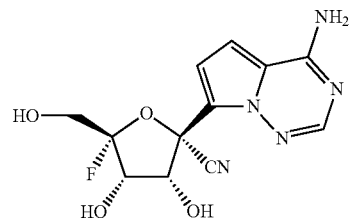 [SMILES: N#C[C@@]1(c2ccc3c(N)ncnn23)O[C@](F)(CO)[C@@H](O)[C@H]1O]

Step A. (2R,3R,4S,5S)-2-(4-Aminopyrrolo[2,1-f][1,2,4]triazin-7-yl)-3,4-dihydroxy-5-(iodomethyl)tetrahydrofuran-2-carbonitrile To a solution of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (Intermediate 1, 6 g, 20.5 mmol) in tetrahydrofuran (120 mL) under inert atmosphere was added triphenylphosphine (10.8 g, 41.2 mmol, 2.00 equiv) and imidazole (6.99 g, 102.7 mol, 5.00 equiv). A solution of iodine (10.4 g, 41.2 mmol, 2.00 equiv) in tetrahydrofuran (10 mL) was added dropwise to the reaction mixture with stirring at room temperature. The resulting solution was stirred for 2 h at 50° C. After concentration under reduced pressure, the residue was purified by reverse phase chromatography with ACN/H2O to afford 6 g (72.6%) of the title compound as a yellow solid. MS m/z: 402 [M+H]+.

Step B. (2R,3R,4S)-2-(4-Aminopyrrolo[2,1-f][1,2,4]triazin-7-yl)-3,4-dihydroxy-5-methylenetetrahydrofuran-2-carbonitrile To a solution of (2R,3R,4S,5S)-2-(4-aminopyrrolo[2,1-f][1,2,4]triazin-7-yl)-3,4-dihydroxy-5-(iodomethyl)tetrahydrofuran-2-carbonitrile (12 g, 29.9 mmol) in acetonitrile (240 mL) was added 1,8-diazabicyclo[5.4.0]undec-7-ene (15 g, 59.8 mmol, 2.00 equiv) at room temperature. The resulting solution was stirred for 4 h at 60° C. After concentration under reduced pressure, the residue was purified by reverse phase chromatography with ACN/H₂O to afford 7 g (79%) of the title compound as a yellow solid. MS m/z: 274 [M+H]⁺.

Step C. (2R,3R,4S,5R)-2-(4-Aminopyrrolo[2,1-f][1,2,4]triazin-7-yl)-5-fluoro-3,4-dihydroxy-5-(iodomethyl)tetrahydrofuran-2-carbonitrile To a solution of (2R,3R,4S)-2-(4-aminopyrrolo[2,1-f][1,2,4]triazin-7-yl)-3,4-dihydroxy-5-methylenetetrahydrofuran-2-carbonitrile (2 g, 7.32 mmol, 1.00 equiv) in tetrahydrofuran (60 mL) under inert atmosphere was added triethylamine trihydrofluoride (2.94 g, 18.3 mmol, 2.50 equiv) and N-iodosuccinimide (2.47 g, 10.98 mmol, 1.50 equiv) at room temperature. The resulting solution was stirred for 2 h. After concentration under reduced pressure, the residue was purified by reverse phase chromatography with ACN/H₂O to afford 1 g (33%) of the title compound as a yellow solid. MS m/z: 420 [M+H]⁺.

Step D. (2R,3R,4S,5R)-2-(4-Benzamidopyrrolo[2,1-f][1,2,4]triazin-7-yl)-2-cyano-5-fluoro-5-(iodomethyl)tetrahydrofuran-3,4-diyl dibenzoate To a solution of (2R,3R,4S,5R)-2-(4-aminopyrrolo[2,1-f][1,2,4]triazin-7-yl)-5-fluoro-3,4-dihydroxy-5-(iodomethyl)tetrahydrofuran-2-carbonitrile (1.1 g, 2.62 mmol) in pyridine (22 mL) under inert atmosphere was added benzoyl chloride (1.66 g, 11.8 mmol, 4.50 equiv) dropwise with stirring at 0° C. The resulting solution was stirred for 2 h at 0° C., and then quenched by the addition of water (100 mL). The resulting solution was extracted with dichloromethane (100 mL×2) and the combined organic extracts dried over anhydrous sodium sulfate. After filtration, the resulting solution was concentrated under reduced pressure. Purification (silica gel column with ethyl acetate/petroleum ether (1:10-1:2)) afforded 1.1 g (58%) of the title compound as a yellow solid. MS m/z: 732 [M+H]⁺.

Step E. (2R,3R,4S,5S)-2-(4-benzamidopyrrolo[2,1-f][1,2,4]triazin-7-yl)-5-((benzoyloxy)methyl)-2-cyano-5-fluorotetrahydrofuran-3,4-diyl dibenzoate To a solution of (2R,3R,4S,5R)-2-(4-benzamidopyrrolo[2,1-f][1,2,4]triazin-7-yl)-2-cyano-5-fluoro-5-(iodomethyl)tetrahydrofuran-3,4-diyl dibenzoate (700 mg, 0.96 mmol) in N,N-dimethylformamide (70 mL) was added potassium benzoate (767 mg, 4.79 mmol, 5.00 equiv) and 18-Crown-6 (507.5 mg, 1.92 mmol, 2.00 equiv). The resulting solution was stirred for 16 h at 100° C. The resulting solution was diluted with ethyl acetate, washed with water and dried over anhydrous sodium sulfate. After filtration, the resulting solution was concentrated under reduced pressure. Purification (silica gel column with ethyl acetate/petroleum ether (1:10-1:2)) afforded 350 mg (50%) of the title compound as a yellow solid. MS m/z: 726 [M+H]⁺.

Step F. (2R,3R,4S,5S)-2-(4-Aminopyrrolo[2,1-f][1,2,4]triazin-7-yl)-5-fluoro-3,4-dihydroxy-5-(hydroxymethyl)tetrahydrofuran-2-carbonitrile A solution of (2R,3R,4S,5S)-2-(4-benzamidopyrrolo[2,1-f][1,2,4]triazin-7-yl)-5-((benzoyloxy)methyl)-2-cyano-5-fluorotetrahydrofuran-3,4-diyl dibenzoate. (590 mg, 0.58 mmol, 1.00 equiv) in 2 N NH₃/MeOH (20 mL) was stirred for 20 h at room temperature. The resulting mixture was concentrated under reduced pressure. Purification (silica gel column with DCM/MeOH (6:1)) afforded 150 mg (60%) of the title compound as a white solid. MS m/z: 310 [M+H]⁺. ¹H-NMR (CD₃OD): δ 7.89 (s, 1H), 7.01 (d, J=4.6 Hz, 1H), 6.90 (d, J=4.6 Hz, 1H), 4.75 (d, J=6.3 Hz, 1H), 4.49 (dd, J=20.0, 6.4 Hz, 1H), 3.90-3.71 (m, 2H). ¹⁹F-NMR (CD₃OD): δ–125.07.

Example 2

Compound 2: (2R,3R,4S,5S)-2-(4-Aminopyrrolo[2,1-f][1,2,4]triazin-7-yl)-5-azido-3,4-dihydroxy-5-(hydroxymethyl)tetrahydrofuran-2-carbonitrile

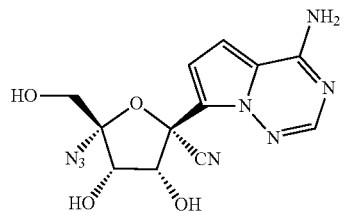 [SMILES: N#C[C@@]1(c2ccc3c(N)ncnn23)O[C@@](CO)(N=[N+]=[N-])[C@@H](O)[C@H]1O]

Step A. (2R,3R,4S,5S)-2-(4-aminopyrrolo[2,1-f][1,2,4]triazin-7-yl)-5-azido-3,4-dihydroxy-5-(iodomethyl)tetrahydrofuran-2-carbonitrile To a solution of IC1 (1.19 g, 7.3 mmol, 2.50 equiv) in DMF (4 mL) was added NaN₃ (951 mg, 14.6 mmol, 5.00 equiv). After stirring for 30 min at 30° C., a solution of (2R,3R,4S)-2-(4-aminopyrrolo[2,1-f][1,2,4]triazin-7-yl)-3,4-dihydroxy-5-methylenetetrahydrofuran-2-carbonitrile (Compound 1, product from Step B, 800 mg, 2.92 mmol, 1.00 equiv) in DMF (8 mL) was added to the stirred solution at room temperature. The resulting solution was stirred for 1 h at room temperature, and then quenched by the addition of 8 mL of Na₂S₂O₃ (aq.). The resulting mixture was concentrated under reduced pressure and purified by reverse-phase flash chromatography (ACN/H₂O) to afford 0.88 g (60%) of the title compound as a light yellow solid. MS m/z: 443 [M+H]⁺.

Step B. (2S,3S,4R,5R)-2-Azido-5-(4-benzamidopyrrolo[2,1-f][1,2,4]triazin-7-yl)-5-cyano-2-(iodomethyl)tetrahydrofuran-3,4-diyl dibenzoate To a solution of (2R,3R,4S,5S)-2-(4-aminopyrrolo[2,1-f][1,2,4]triazin-7-yl)-5-azido-3,4-dihydroxy-5-(iodomethyl)tetrahydrofuran-2-carbonitrile (500 mg, 1.13 mmol) in anhydrous pyridine (6 mL) under inert atmosphere was added benzoyl chloride (715 mg, 5.1 mmol, 4.5 equiv) at 0° C. and the mixture was stirred for 1.5 h at 0° C. The reaction was quenched by the addition of MeOH (2 mL), and concentrated under reduced pressure, then dissolved in ethyl acetate (100 mL), washed with aq. NaHCO₃ (30 mL), aq. NaCl (30 mL) and the organic layers were dried over sodium sulfate, filtered and concentrated under reduced pressure. Purification (silica gel column with PE/EA=2/1) afforded 597 mg (70%) of the title compound as a yellow solid. MS m/z: 755 [M+H]⁺.

Step C. (2R,3S,4R,5R)-2-azido-5-(4-benzamidopyrrolo[2,1-f][1,2,4]triazin-7-yl)-5-cyano-2-((2,2,2-trifluoroacetoxy)methyl)tetrahydrofuran-3,4-diyl dibenzoate and (2R,3S,4R,5R)-2-azido-5-(4-benzamidopyrrolo[2,1-f][1,2,4]triazin-7-yl)-5-cyano-2-(hydroxymethyl)tetrahydrofuran-3,4-diyl dibenzoate To a solution of (2S,3S,4R,5R)-2-azido-5-(4-benzamidopyrrolo[2,1-f][1,2,4]triazin-7-yl)-5-cyano-2-(iodomethyl)tetrahydrofuran-3,4-diyl dibenzoate (500 mg, 0.66 mmol) in 1,2-dichloroethane (10 mL) was added CF$_3$COOAg (1.46 g, 6.6 mmol, 10 equiv) at room temperature. The resulting solution was stirred for 8 h at 90° C. protected from light. The resulting solution was diluted with ethyl acetate (100 mL), and washed with aq. NaHCO$_3$ (30 mL), aq. NaCl (30 mL), dried over sodium sulfate, filtered and concentrated under reduced pressure to afford 450 mg of m(2R,3S,4R,5R)-2-azido-5-(4-benzamidopyrrolo[2,1-f][1,2,4]triazin-7-yl)-5-cyano-2-((2,2,2-trifluoroacetoxy)methyl)tetrahydrofuran-3,4-diyl dibenzoate and (2R,3S,4R,5R)-2-azido-5-(4-benzamidopyrrolo[2,1-f][1,2,4]triazin-7-yl)-5-cyano-2-(hydroxymethyl)tetrahydrofuran-3,4-diyl dibenzoate as a yellow solid. Crude mixture was used directly for the next step. MS m/z: 741[M+H]$^+$ for (2R,3S,4R,5R)-2-azido-5-(4-benzamidopyrrolo[2,1-f][1,2,4]triazin-7-yl)-5-cyano-2-((2,2,2-trifluoroacetoxy)methyl)tetrahydrofuran-3,4-diyl dibenzoate and 645[M+H]$^+$ for (2R,3S,4R,5R)-2-azido-5-(4-benzamidopyrrolo[2,1-f][1,2,4]triazin-7-yl)-5-cyano-2-(hydroxymethyl)tetrahydrofuran-3,4-diyl dibenzoate.

Step D. (2R,3R,4S,5R)-2-(4-aminopyrrolo[2,1-f][1,2,4]triazin-7-yl)-5-azido-3,4-dihydroxy-5-(hydroxymethyl)tetrahydrofuran-2-carbonitrile The mixture of (2R,3S,4R,5R)-2-azido-5-(4-benzamidopyrrolo[2,1-f][1,2,4]triazin-7-yl)-5-cyano-2-((2,2,2-trifluoroacetoxy)methyl)tetrahydrofuran-3,4-diyl dibenzoate and (2R,3S,4R,5R)-2-azido-5-(4-benzamidopyrrolo[2,1-f][1,2,4]triazin-7-yl)-5-cyano-2-(hydroxymethyl)tetrahydrofuran-3,4-diyl dibenzoate (400 mg, 1.78 mmol) was dissolved in 2N NH$_3$ in methanol (10 mL) and stirred for 20 h at room temperature. The resulting solution was concentrated under reduced pressure. Purification by RP-HPLC (XBridge Prep C18 OBD Column, 19×150 mm, 5 μm; mobile phase, A: 10 mM NH$_4$HCO$_3$ in water, B: 10 mM NH$_4$HCO$_3$ in ACN (5.0% ACN up to 27.0% in 7 min); Detector, UV 254/220 nm) afforded 56.3 mg (34%) of the title compound as a light yellow solid. MS m/z: 333 [M+H]$^+$. $^1$H NMR (CD$_3$OD) δ 7.88 (s, 1H), 7.03 (d, J=4.6 Hz, 1H), 6.93 (d, J=4.6 Hz, 1H), 5.02 (d, J=5.8 Hz, 1H), 4.43 (d, J=5.8 Hz, 1H), 3.82 (d, J=12.2 Hz, 1H), 3.69 (d, J=12.2 Hz, 1H).

Example 3

Compound 3: (2R,3R,4S,5R)-2-(4-Aminopyrrolo[2,1-f][1,2,4]triazin-7-yl)-5-(fluoromethyl)-3,4-dihydroxy-5-(hydroxymethyl)tetrahydrofuran-2-carbonitrile

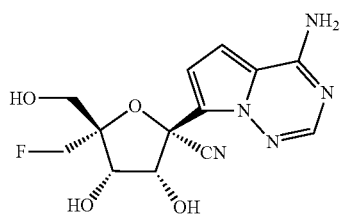 [SMILES: N#C[C@@]1(c2ccc3c(N)ncnn23)O[C@@](CO)(CF)[C@@H](O)[C@H]1O]

Step A. (3R,4S,5R)-2-(4-Aminopyrrolo[2,1-f][1,2,4]triazin-7-yl)-3,4-bis(benzyloxy)-5-((benzyloxy)methyl)-5-(fluoromethyl)tetrahydrofuran-2-ol To a solution of 7-bromopyrrolo[2,1-f][1,2,4]triazin-4-amine (0.781 g, 3.667 mmol, 1.1 equiv) in anhydrous THF (200 mL) under inert atmosphere, was added sodium hydride (60%, 293 mg, 7.33 mmol, 2.2 equiv), then immediately added 1,1,4,4-tetramethyl-1,4-dichlorodisilethylene (0.78 g, 3.667 mmol, 1.1 equiv). The mixture was stirred for 20 min at room temperature. The reaction was then cooled to −78° C. and n-butyllithium (2.5 M in hexanes, 4.4 mL, 11 mmol, 3.3 equiv) was added slowly over 10 min. The reaction was allowed to stir for 20 min before (3R,4S,5R)-3,4-bis(benzyloxy)-5-((benzyloxy)methyl)-5-(fluoromethyl)dihydrofuran-2(3H)-one (Intermediate 2, 1.5 g, in 5 mL THF, 3.33 mmol, 1.00 equiv) was added dropwise. The resulting solution was stirred for 1 h at −78° C., and then quenched by the addition of aq. NH$_4$C$_1$ (200 mL). The resulting solution was extracted with ethyl acetate (200 mL×3) and the organic layers were combined, dried over anhydrous sodium sulfate, filtered and concentrated under reduced pressure. The crude product was purified by reverse phase flash chromatography (ACN/H$_2$O) to afford 1.15 g (59%) of the title compound (two isomers, ratio: 1/1) as a yellow solid. MS m/z: 585 [M+H]$^+$.

Step B. (2R,3R,4S,5R)-2-(4-Aminopyrrolo[2,1-f][1,2,4]triazin-7-yl)-3,4-bis(benzyloxy)-5-((benzyloxy)methyl)-5-(fluoromethyl)tetrahydrofuran-2-carbonitrile and (2S,3R,4S,5R)-2-(4-Aminopyrrolo[2,1-f][1,2,4]triazin-7-yl)-3,4-bis(benzyloxy)-5-((benzyloxy)methyl)-5-(fluoromethyl)tetrahydrofuran-2-carbonitrile To a solution of (3R,4S,5R)-2-(4-aminopyrrolo[2,1-f][1,2,4]triazin-7-yl)-3,4-bis(benzyloxy)-5-((benzyloxy)methyl)-5-(fluoromethyl)tetrahydrofuran-2-ol (1.15 g, 1.97 mmol, 1.00 equiv) in DCM (20 mL) under inert atmosphere, was added trimethylsilanecarbonitrile (682 mg, 6.90 mmol, 3.50 equiv) dropwise at 0° C. The resulting solution was stirred for 10 min. To this solution was added trimethylsilyl trifluoromethanesulfonate (1.96 g, 8.87 mmol, 4.50 equiv) dropwise at 0° C. The resulting solution was stirred for 2 h at 0° C., and then quenched by the addition of aq. NaHCO$_3$ (200 mL). The resulting solution was extracted with DCM (2×200 mL) and the organic layers were combined and dried over anhydrous sodium sulfate, filtered and concentrated under reduced pressure. Purification by reverse phase flash chromatography (ACN/H$_2$O) afforded 397 mg (35%) of (2R,3R,4S,5R)-2-(4-aminopyrrolo[2,1-f][1,2,4]triazin-7-yl)-3,4-bis(benzyloxy)-5-((benzyloxy)methyl)-5-(fluoromethyl)tetrahydrofuran-2-carbonitrile as a yellow solid and 390 mg (35%) of (2S,3R,4S,5R)-2-(4-aminopyrrolo[2,1-f][1,2,4]triazin-7-yl)-3,4-bis(benzyloxy)-5-((benzyloxy)methyl)-5-(fluoromethyl)tetrahydrofuran-2-carbonitrile as a yellow solid. MS m/z: 594 [M+H]$^+$.

Step C. (2R,3R,4S,5R)-2-(4-Aminopyrrolo[2,1-f][1,2,4]triazin-7-yl)-5-(fluoromethyl)-3,4-dihydroxy-5-(hydroxymethyl)tetrahydrofuran-2-carbonitrile To a solution of (2R,3R,4S,5R)-2-(4-aminopyrrolo[2,1-f][1,2,4]triazin-7-yl)-3,4-bis(benzyloxy)-5-((benzyloxy)methyl)-5-(fluoromethyl)tetrahydrofuran-2-carbonitrile (350 mg, 0.59 mmol, 1.00 equiv) in DCM (1 mL) under inert atmosphere, was added a solution of boron trichloride (1M in DCM, 20 mL) dropwise at −20° C. The resulting solution was stirred for 1 h at −20° C., and then quenched by the addition of $K_2CO_3$/MeOH. The pH value of the solution was adjusted to 7 with TEA. The solids were filtered off and the resulting filtrate was concentrated under reduced pressure. The crude product (100 mg) was purified by RP-HPLC (XBridge Prep C18 OBD Column, 19×150 mm 55 μm; Mobile phase, A:10 mM aq. $NH_4HCO_3$, B: 10 mM $NH_4HCO_3$ in MeCN; Gradient 5 to 27% B; Detector, UV 254/220 nm) to afford 59.3 mg (31.3%) of the title compound as a white solid. MS m/z: 324 [M+H]$^+$. $^1$H-NMR (CD$_3$OD): δ 7.86 (s, 1H), 6.89 (d, J=4.8 Hz, 1H), 6.82 (d, J=4.8 Hz, 1H), 5.09 (d, J=5.6 Hz, 1H), 4.60-4.80 (m, 2H), 4.37 (d, J=5.6 Hz, 1H), 3.20-3.23 (m, 2H). $^{19}$F-NMR (CD$_3$OD): δ−237.30.

Example 4

Compound 4: (2R,3R,4S,5R)-2-(4-Aminopyrrolo[2,1-f][1,2,4]triazin-7-yl)-3,4-dihydroxy-5-(hydroxymethyl)tetrahydrofuran-2,5-dicarbonitrile

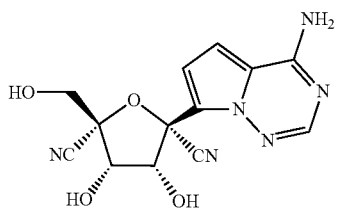 [SMILES: N#C[C@]1(CO)O[C@@](C#N)(c2ccc3c(N)ncnn23)[C@H](O)[C@@H]1O]

Step A. (2R,3R,4S)-2-(4-Aminopyrrolo[2,1-f][1,2,4]triazin-7-yl)-3,4-bis((tert-butyldimethylsilyl)oxy)-5-methylenetetrahydrofuran-2-carbonitrile To a solution of (2R,3R,4S)-2-(4-aminopyrrolo[2,1-f][1,2,4]triazin-7-yl)-3,4-dihydroxy-5-methylenetetrahydrofuran-2-carbonitrile (800 mg, 2.92 mmol) in DMF (8 mL) under inert atmosphere, was added imidazole (981 mg, 14.7 mmol, 5 equiv), DMAP (356.2 mg, 2.92 mmol, equiv), tert-butyl(chloro)dimethylsilane (TBDMSCl) (2.2 g, 14.7 mmol, 5 equiv) and the mixture was stirred for 5 h at 60° C. The reaction was quenched by the addition of CH$_3$OH (5 mL), diluted with ethyl acetate (100 mL), washed with aq. NaHCO$_3$ (30 mL×2), aq. NaCl (30 mL). The combined organic layers were dried over sodium sulfate, filtered and concentrated under reduced pressure. Purification on silica gel column with DCM/MeOH (30:1) afforded 1 g (68%) of the title compound as a light yellow solid. MS m/z [M+H]$^+$ (ESI): 502.

Step B. N-(7-((2R,3R,4S)-3,4-Bis((tert-butyldimethylsilyl)oxy)-2-cyano-5-methylenetetrahydrofuran-2-yl)pyrrolo[2,1-f][1,2,4]triazin-4-yl)benzamide To a solution of (2R,3R,4S)-2-(4-aminopyrrolo[2,1-f][1,2,4]triazin-7-yl)-3,4-bis((tert-butyldimethylsilyl)oxy)-5-methylenetetrahydrofuran-2-carbonitrile (1 g, 2.0 mmol, 1.0 equiv) in anhydrous pyridine (10 mL) under inert atmosphere, was added benzoyl chloride (330 mg, 2.4 mmol, 1.2 equiv) at 0° C. and the mixture was stirred for 2 h at 0° C. The reaction was quenched by the addition of MeOH (2 mL), and the reaction mixture was concentrated under reduced pressure. The crude evaporated residue was dissolved in ethyl acetate (100 mL), washed with aq. NaHCO$_3$ (30 mL), aq. NaCl (30 mL). The organic layer was dried over sodium sulfate, filtered and concentrated under reduced pressure. Purification on silica gel column with PE/EA (5:1) afforded 700 mg (58%) of the title compound as a yellow solid. MS m/z [M+H]$^+$ (ESI): 606.

Step C. N-(7-((5R,6R,7S)-6,7-Bis((tert-butyldimethylsilyl)oxy)-5-cyano-1,4-dioxaspiro[2.4]heptan-5-yl)pyrrolo[2,1-f][1,2,4]triazin-4-yl)benzamide To a solution of N-(7-((2R,3R,4S)-3,4-bis((tert-butyldimethylsilyl)oxy)-2-cyano-5-methylenetetrahydrofuran-2-yl)pyrrolo[2,1-f][1,2,4]triazin-4-yl)benzamide (700 mg, 1.16 mmol, 1.00 equiv) in DCM (10 mL), was added NaHCO$_3$ (1.46 g, 17.4 mmol, 15 equiv), H$_2$O (7 mL) and acetone (4.03 g, 69.6 mmol, 60 equiv). The reaction mixture was cooled to 0° C. then a solution of oxone (2.85 g, 4.64 mmol, 4 equiv) in H$_2$O (20 mL) was added dropwise at 0° C. The resulting solution was stirred for 3 h at 0° C. then diluted with ethyl acetate (100 mL) and washed with aq. Na$_2$S$_2$O$_3$ (20 mL) and brine (30 mL). The organic layer was dried over sodium sulfate, filtered and concentrated under reduced pressure to afford 750 mg of the title compound as a yellow solid. The crude compound was used directly for the next steps without further purification. MS m/z [M+H]$^+$ (ESI): 622.

Step D. N-(7-((2R,3R,4S)-3,4-Bis((tert-butyldimethylsilyl)oxy)-2,5-dicyano-5-(((trimethylsilyl)oxy)methyl)tetrahydrofuran-2-yl)pyrrolo[2,1-f][1,2,4]triazin-4-yl)benzamide To a solution of N-(7-((5R,6R,7S)-6,7-bis((tert-butyldimethylsilyl)oxy)-5-cyano-1,4-dioxaspiro[2.4]heptan-5-yl)pyrrolo[2,1-f][1,2,4]triazin-4-yl)benzamide (750 mg, 1.20 mmol) in DCM (20 mL), was added TMSCN (831 mg, 8.4 mmol, 7.0 eq). To this mixture was added InBr$_3$ (1.1 g, 3.0 mmol, 2.5 eq) at 0° C. The reaction mixture was stirred for 3 h at 0° C. The reaction mixture was diluted with ethyl acetate (100 mL), washed with aq. NaHCO$_3$ (30 mL×2), then brine (30 mL). The organic layer was dried over sodium sulfate, filtered and concentrated under reduced pressure to afford 800 mg of crude title compound (two isomers, ratio 3/1) as a yellow solid which was used directly for the next steps. MS m/z [M+H]$^+$ (ESI): 721.

Step E. N-(7-((2R,3R,4S)-2,5-Dicyano-3,4-dihydroxy-5-(hydroxymethyl) tetrahydrofuran-2-yl)pyrrolo[2,1-f][1,2,4]triazin-4-yl)benzamide To a solution of N-(7-((2R,3R,4S)-3,4-bis((tert-butyldimethylsilyl)oxy)-2,5-dicyano-5-(((trimethylsilyl)oxy)methyl)tetrahydrofuran-2-yl)pyrrolo[2,1-f][1,2,4]triazin-4-yl)benzamide (800 mg, 1.11 mmol, 1.00 equiv) in DCM (8 mL), was added TEA 3HF (2.14 g, 13.3 mmol, 12 equiv) and TEA (2.69 g, 26.6 mmol, 24 equiv). The resulting solution was stirred for 20 h at room temperature. The reaction mixture was concentrated under reduced pressure and the residue dissolved in ethyl acetate (100 mL) and washed with aq. NaHCO$_3$ (30 mL×2), and brine (30 mL). The organic layer was dried over sodium sulfate, filtered and concentrated under reduced pressure to afford 450 mg of crude title compound (two isomers, ratio 3/1) as a red oil. MS m/z [M+H]$^+$ (ESI): 421.

Step F. (2R,3R,4S,5R)-2-(4-Aminopyrrolo[2,1-f][1,2,4]triazin-7-yl)-3,4-dihydroxy-5-(hydroxymethyl)tetrahydrofuran-2,5-dicarbonitrile and (2R,3R,4S,5S)-2-(4-Aminopyrrolo[2,1-f][1,2,4]triazin-7-yl)-3,4-dihydroxy-5-(hydroxymethyl)tetrahydrofuran-2,5-dicarbonitrile A solution of N-(7-((2R,3R,4S)-2,5-dicyano-3,4-dihydroxy-5-(hydroxymethyl)tetrahydrofuran-2-yl)pyrrolo[2,1-f][1,2,4]triazin-4-yl)benzamide (450 mg, 1.07 mmol) in in methanolic ammonia (2N, 14 mL) was stirred for 20 h at room temperature. The resulting solution was concentrated under reduced pressure. Purification by RP-HPLC (XBridge Prep C18 OBD Column, 19×150 mm 5 um; mobile phase, A: 10 mM aq., NH$_4$HCO$_3$, B: 10 mM NH$_4$HCO$_3$ in ACN; gradient 5% to 27% B in 7 min; detector, UV 254/220 nm) afforded 60 mg (16% for four steps) of (2R,3R,4S,5R)-2-(4-Aminopyrrolo[2,1-f][1,2,4]triazin-7-yl)-3,4-dihydroxy-5-(hydroxymethyl)tetrahydrofuran-2,5-dicarbonitrile (Compound 4) as a light yellow solid. MS: m/z 317 [M+H]$^+$. $^1$H NMR (CD$_3$OD) δ 7.91 (s, 1H), 6.98 (d, J=4.6 Hz, 1H), 6.94 (d, J=4.6 Hz, 1H), 5.39 (d, J=4.6 Hz, 1H), 4.68 (d, J=4.6 Hz, 1H), 4.05 (s, 2H).

Example 5

Compound 5: Isopropyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-D-alaninate

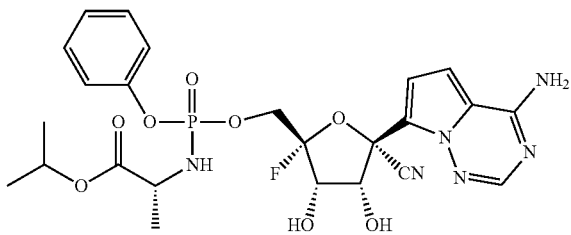

Step A. (3aR,4R,6R,6aS)-4-(4-Aminopyrrolo[2,1-f][1,2,4]triazin-7-yl)-6-fluoro-6-(iodomethyl)-2-methoxytetrahydrofuro[3,4-d][1,3]dioxole-4-carbonitrile To a solution of (2R,3R,4S,5R)-2-(4-aminopyrrolo[2,1-f][1,2,4]triazin-7-yl)-5-fluoro-3,4-dihydroxy-5-(iodomethyl)tetrahydrofuran-2-carbonitrile (Compound 1, product from Step C, 500 mg, 1.19 mmol) in dioxane (10 mL) under inert atmosphere was added trimethoxymethane (10 mL), and PTSA (158.2 mg, 0.92 mmol, 0.77 equiv). The resulting solution was stirred for 3 h at 50° C. The reaction was then quenched by the addition of triethylamine, and concentrated under reduced pressure. Purification on silica gel column with DCM/MeOH (100:1-20:1) afforded 340 mg (62%) of the title compound as a yellow oil. MS m/z [M+H]$^+$ (ESI): 462.

Step B. ((3aS,4S,6R,6aR)-6-(4-Aminopyrrolo[2,1-f][1,2,4]triazin-7-yl)-6-cyano-4-fluoro-2-methoxytetrahydrofuro[3,4-d][1,3]dioxol-4-yl)methyl benzoate To a solution of (3aR,4R,6R,6aS)-4-(4-aminopyrrolo[2,1-f][1,2,4]triazin-7-yl)-6-fluoro-6-(iodomethyl)-2-methoxytetrahydrofuro[3,4-d][1,3]dioxole-4-carbonitrile (1.0 g, 2.2 mmol) in DMF (100 mL) under inert atmosphere was added BzOK (1.74 g, 11 mmol, 5.00 equiv), and 18-Crown-6 (1.15 g, 4.4 mmol, 2.00 equiv). The resulting solution was stirred for 16 h at 100° C. The resulting solution was diluted with of EtOAc, washed with H$_2$O and dried over anhydrous sodium sulfate, filtered, and then concentrated under reduced pressure. Purification on silica gel column with EA/PE (1:10-3:1) afforded 600 mg (61%) of the title compound as a yellow solid. MS m/z [M+H]$^+$ (ESI): 456.

Step C. (3aR,4R,6S,6aS)-4-(4-Aminopyrrolo[2,1-f][1,2,4]triazin-7-yl)-6-fluoro-6-(hydroxymethyl)-2-methoxytetrahydrofuro[3,4-d][1,3]dioxole-4-carbonitrile A solution of ((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methyl benzoate (170 mg, 0.37 mmol) in 2N methanolic ammonia (2N, 10 mL) was stirred for 20 h at room temperature. The resulting solution was concentrated under reduced pressure. Purification on silica gel column with DCM/MeOH (100:1-20:1) afforded 72 mg (55%) of the title compound as a white solid. MS m/z [M+H]$^+$ (ESI): 352.

Step D. Isopropyl ((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-D-alaninate To a solution of (3aR,4R,6S,6aS)-4-(4-aminopyrrolo[2,1-f][1,2,4]triazin-7-yl)-6-fluoro-6-(hydroxymethyl)-2-methoxytetrahydrofuro[3,4-d][1,3]dioxole-4-carbonitrile (25 mg, 0.07 mmol) in ACN (1 mL) under inert atmosphere was added 1-methyl-1H-imidazole (58.4 mg, 0.71 mmol, 10.00 equiv). Isopropyl (chloro(phenoxy)phosphoryl)-D-alaninate (39.1 mg, 0.13 mmol, 1.80 equiv) (prepared according to McGuigan et al. J. Med. Chem. 2005, 48(10), 3504-3515) in ACN (0.4 mL) was added to the reaction mixture dropwise with stirring at 0° C. The resulting solution was stirred for 1 h at room temperature. Reaction mixture was diluted with EtOAc, washed with H$_2$O and dried over anhydrous sodium sulfate, filtered, and then concentrated under reduced pressure. Purification on silica gel column with DCM/MeOH (10:1)) afforded 25 mg (57%) of the title compound as a yellow oil. MS m/z [M+H]$^+$ (ESI): 621.

Step E. Isopropyl ((((2S,3 S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-D-alaninate A solution of isopropyl ((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-D-alaninate (69 mg, 0.11 mmol) in 80% aq. HCOOH (2 mL) was stirred for 16 h at room temperature. The resulting mixture was concentrated under reduced pressure. The crude product (70 mg) was purified by RP-HPLC (XBridge Shield RP18 OBD Column, 5 um, 19×150 mm; mobile phase, A; 0.1% aq. HCOOH, B: 0.1% HCOOH in can; gradient 19% to 44% B in 9 min; detector, UV 254 nm) to afford 24 mg (37%) of the title compound as a white solid. MS: m/z 579 [M+H]$^+$. $^1$H-NMR (CD$_3$OD): δ 7.80 (d, J=7.2 Hz, 1H), 7.29-7.23 (m, 2H), 7.15-7.11 (m, 3H), 6.89-6.82 (m, 2H), 4.94-4.89 (m, 1H), 4.77-4.71 (m, 1H), 4.56-4.44 (m, 1H), 4.37-4.27 (m, 2H), 3.85-3.81 (m, 1H), 1.25-1.14 (m, 9H). $^{19}$F-NMR (CD$_3$OD): δ −123.67, −123.88. $^{31}$P-NMR (CD$_3$OD): δ 3.43, 3.17.

Example 6

Compound 6: Isopropyl (((((2S,3 S,4R,5R)-5-(4-aminopyrrolo[2, 1-f][1,2,4]triazin-7-yl)-5-cyano-2-fluoro-3,4-dihydroxytetrahydrofuran-2-yl)methoxy)(phenoxy)phosphoryl)-L-alaninate

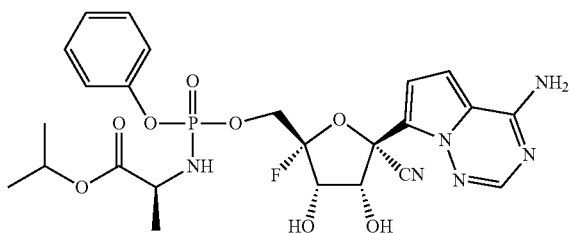

Step A. Isopropyl (((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-L-alaninate To a solution of (3aR,4R,6S,6aS)-4-(4-aminopyrrolo[2,1-f][1,2,4]triazin-7-yl)-6-fluoro-6-(hydroxymethyl)-2-methoxytetrahydrofuro[3,4-d][1,3]dioxole-4-carbonitrile (Compound 5, product from Step C) (29 mg, 0.08 mmol) in ACN (1.16 mL) under inert atmosphere was added 1-methyl-1H-imidazole (67.7 mg, 0.82 mmol, 10.00 equiv). This was followed by the addition of a solution of isopropyl (chloro(phenoxy)phosphoryl)-L-alaninate (45.36 mg, 0.15 mmol, 1.80 equiv) (prepared according to McGuigan et al. J. Med. Chem. 2005, 48(10), 3504-3515) in ACN (0.5 mL) dropwise with stirring at 0° C. The resulting solution was stirred for 1 h at room temperature. Reaction mixture was diluted with EtOAc, washed with H$_2$O and dried over anhydrous sodium sulfate, filtered, and then concentrated under reduced pressure. Purification on silica gel column with DCM/MeOH (10:1) afforded 29 mg (57%) of the title compound as a yellow oil. MS m/z [M+H]$^+$ (ESI): 621.

Step B. Isopropyl (((((2S,3 S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-L-alaninate A solution of isopropyl (((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-L-alaninate (80 mg, 0.13 mmol) in 80% aq. HCOOH (8 mL) was stirred for 16 h at room temperature. The resulting mixture was concentrated under reduced pressure. The crude evaporated residue was purified by RP-HPLC (XBridge Shield RP18 OBD Column, 5 um, 19×150 mm; mobile phase, A: 0.1% aq. HCOOH, B: 0.1% HCOOH in ACN; gradient 19% to 44% B in 9 min; detector, UV 254 nm) to afford 31.8 mg (43%) of the title compound as a white solid. MS: m/z 579 [M+H]$^+$. $^1$H-NMR (CD$_3$OD): δ 7.80 (d, J=4.6 Hz, 1H), 7.29-7.24 (m, 2H), 7.16-7.10 (m, 3H), 6.93-6.83 (m, 2H), 4.92-4.85 (m, 1H), 4.75 (d, J=6.5 Hz, 1H), 4.55-4.46 (m, 1H), 4.34-4.29 (m, 2H), 3.87-3.70 (m, 1H), 1.27-1.13 (m, 9H). $^{19}$F-NMR (CD$_3$OD): δ−123.83, −124.03. $^{31}$P-NMR (CD$_3$OD): δ 3.45, 3.29.

Example 7

Compound 7: Diisopentyl (((((2S,3S,4R,5R)-5-(4-aminopyrrolo[2,1-f][1,2,4]triazin-7-yl)-5-cyano-2-fluoro-3,4-dihdroxytetrahydrofuran-2-yl)methoxy)(phenoxy)phosphoryl)-L-aspartate

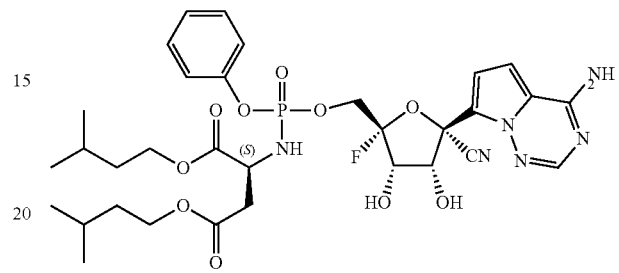

Step A. Diisopentyl L-aspartate hydrochloride

To a solution of L-aspartic acid (1 g, 7.51 mmol) in 3-methylbutan-1-ol (40 mL) was added chlorotrimethylsilane (5.72 mL, 6.00 equiv) dropwise with stirring at 0° C. The resulting solution was stirred for 48 h at rt. The reaction mixture was concentrated under reduced pressure, the residue was purified on silica gel column with dichloromethane/methanol (50:1-10:1) to afford 2.1 g (91%) of the title compound as a yellow oil. MS m/z [M+H]$^+$ (ESI): 274.

Step B. Diisopentyl (chloro(phenoxy)phosphoryl)-L-aspartate

To a solution of phenoxyphosphonoyl dichloride (340 mg, 1.61 mmol) in dichloromethane (8 mL) was added diisopentyl L-aspartate hydrochloride (521 mg, 1.69 mmol, 1.05 equiv), followed by the addition of TEA (0.47 mL, 3.38 mmol, 2.10 equiv) dropwise with stirring at −78° C. The resulting solution was stirred for 3 h at −78° C. to rt. Reaction mixture was diluted with dry cyclohexane, filtered and concentrated under reduced pressure. Purification on silica gel column with hexane:EA (10:1) afforded 340 mg (47%) of the title compound as a yellow oil. $^{31}$P-NMR (CDCl$_3$): δ 8.39, 8.29.

Step C. Diisopentyl (((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-L-aspartate To a solution of (3aR,4R,6S,6aS)-4-(4-aminopyrrolo[2,1-f][1,2,4]triazin-7-yl)-6-fluoro-6-(hydroxymethyl)-2-methoxytetrahydrofuro[3,4-d][1,3]dioxole-4-carbonitrile (Compound 5, product from Step C, 25 mg, 0.07 mmol) in ACN (1 mL) was added Me-Im (58.4 mg, 0.71 mmol, 10.00 equiv), followed by the addition of a solution of diisopentyl (chloro(phenoxy)phosphoryl)-L-aspartate (57.4 mg, 0.13 mmol, 1.80 equiv) in ACN (0.4 mL) dropwise with stirring at 0° C. The resulting solution was stirred for 1 h at room temperature. The resulting solution was diluted with EtOAc, washed with H$_2$O and the organic layers dried over anhydrous sodium sulfate, filtered, and concentrated under Step D. Diisopentyl ((((2S,3 S,4R,5R)-5-(4-amino-pyrrolo[2,1-f][1,2,4]triazin-7-yl)-5-cyano-2-fluoro-3, 4-dihydroxytetrahydrofuran-2-yl)methoxy)(phenoxy)phosphoryl)-L-aspartate A solution of diisopentyl ((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-L-aspartate (85 mg, 0.11 mmol, 1.00 equiv) in 80% aq. HCOOH (10 mL) was stirred for 16 h at room temperature. The resulting mixture was concentrated under reduced pressure. The crude product (85 mg) was purified by RP-HPLC (XBridge Shield RP18 OBD Column, 5 um, 19×150 mm; mobile phase, A: 0.1% aq. HCOOH, B: 0.1% HCOOH in ACN; gradient 15% to 46% B in 10 min; detector, UV 254 nm) to afford 37.4 mg (47%) of the title compound as a white solid. MS: m/z 721 [M+H]$^+$. $^1$H-NMR (CD$_3$OD): δ 7.88 (d, J=7.0 Hz, 1H), 7.43-7.27 (m, 2H), 7.20 (m, 3H), 7.06-6.83 (m, 2H), 4.79 (d, J=6.4 Hz, 1H), 4.61-4.31 (m, 3H), 4.26 (m, 1H), 4.22-3.79 (m, 4H), 2.89-2.54 (m, 2H), 1.74-1.56 (m 2H), 1.56-1.28 (m, 4H), 0.91 (m, 12H). $^{19}$F-NMR (CD$_3$OD): δ−123.52, −123.78. $^{31}$P-NMR (CD$_3$OD): δ 3.29, 3.07.

Example 8

Compound 8: Neopentyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-L-alaninate

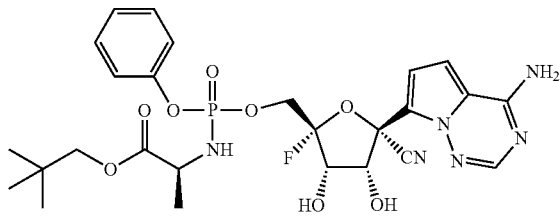

A mixture of (2R,3R,4S,5R)-2-(4-Aminopyrrolo[2,1-f][1,2,4]triazin-7-yl)-3,4-dihydroxy-5-(hydroxymethyl)tetrahydrofuran-2,5-dicarbonitrile (Compound 4, 11 mg, 0.04 mmol), neopentyl (chloro(phenoxy)phosphoryl)-L-alaninate (prepared according to PCT Publication WO 2012/12776 A1) (40 mg, 0.12 mmol) and N-methylimidazole (NMI) (40 μL, 0.48 mmol) in anhydrous acetonitrile (0.4 mL) was stirred overnight under Ar at r.t. then concentrated and purified by RP-HPLC (5-95% B; A: 0.1% aq. HCOOH, B: 0.1% HCOOH in MeCN) to yield 3.2 mg (13%) of the title compound. MS m/z: 607.1 [M+1]$^+$. $^{31}$P-NMR (CD$_3$CN, D$_2$O): δ 2.89 (s), 19F-NMR (CD$_3$CN, D$_2$O): δ−122.63, −123.0 (2 m).

Example 9

Compound 9: 2-Ethylbutyl ((((2S,3S,4R,5R)-5-(4-aminopyrrolo[2,1-f][1,2,4]triazin-7-yl)-5-cyano-2-fluoro-3,4-dihydroxytetrahydrofuran-2-yl)methoxy)(phenoxy)phosphoryl)-D-alaninate

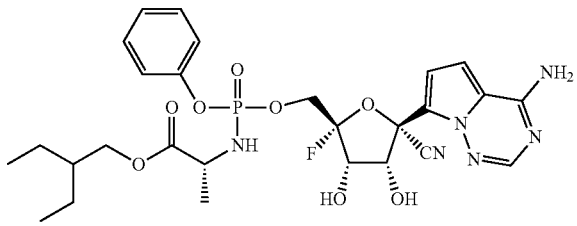

Step A. 2-Ethylbutyl ((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-L-alaninate A mixture of (3aR,4R,6S,6aS)-4-(4-aminopyrrolo[2,1-f][1,2,4]triazin-7-yl)-6-fluoro-6-(hydroxymethyl)-2-methoxytetrahydrofuro[3,4-d][1,3]dioxole-4-carbonitrile (Compound 5, product from Step C, 14 mg, 0.04 mmol), NMI (40 μL, 0.48 mmol) and 2-ethylbutyl (chloro(phenoxy)phosphoryl)-L-alaninate (43 mg, 0.12 mmol) in acetonitrile (0.5 mL) was stirred at r. t. overnight under Ar. The mixture was then diluted with EtOAc and washed consecutively with 1N citric acid, water, sat. aq. NaHCO$_3$, brine and dried (Na$_2$SO$_4$). Crude evaporated residue was purified by flash chromatography on silica gel with a gradient of 4-10% MeOH in DCM to yield the title compound as a colorless crisp foam (20 mg, 76%). MS m/z: 663.1 [M+1]$^+$.

Step B: 2-Ethylbutyl ((((2S,3S,4R,5R)-5-(4-aminopyrrolo[2,1-f][1,2,4]triazin-7-yl)-5-cyano-2-fluoro-3, 4-dihydroxytetrahydrofuran-2-yl)methoxy)(phenoxy)phosphoryl)-L-alaninate A solution of 2-ethylbutyl ((((3aS,4S,6R,6aR)-6-(4-aminopyrrolo[2,1-f][1,2,4]triazin-7-yl)-6-cyano-4-fluoro-2-methoxytetrahydrofuro[3,4-d][1,3]dioxol-4-yl)methoxy)(phenoxy)phosphoryl)-L-alaninate (20 mg, 0.03 mmol) in 80% aq. formic acid (1 mL) was stirred for 4 h at r. t., then concentrated and several times co-evaporated with a mixture of toluene and MeCN, and finally with MeOH containing 1 drop of Et$_3$N. Crude evaporated residue was purified by flash chromatography on silica gel with a gradient of 4-10% MeOH in DCM to yield 14 mg (77%) of the title compound. MS m/z: 618.9 [M−1]$^-$. $^{31}$P-NMR (CD$_3$OD): δ 3.34, 3.20 (2s), $^{19}$F-NMR (CD$_3$CN, D$_2$O): δ−124.03, −123.80 (2 m).

Example 10

Compound 10

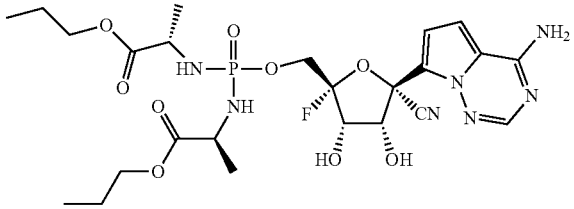

Step A. propyl L-alaninate hydrochloride

To a solution of L-alanine (500 mg, 5.61 mmol) in propan-1-ol (20 mL) was added thionyl chloride (4 g, 33.62 mmol, 6.00 equiv) dropwise with stirring at 0° C. The resulting solution was stirred for 3 h at 90° C., and concentrated under reduced pressure. The resulting solution was diluted with n-hexane. The solids were collected by filtration. This resulted in 900 mg (95%) of propyl L-alaninate hydrochloride as a white solid. MS m/z [M+H]$^+$ (ESI): 132.

Step B. dipropyl 2,2'-((chlorophosphoryl)bis(azanediyl))(2S,2'S)-dipropionate To a solution of propyl L-alaninate hydrochloride (855 mg, 6.52 mmol, 2.00 equiv) in dichloromethane (20 mL) under inert atmosphere was added POCl$_3$ (500 mg, 3.26 mmol, 1.00 equiv) at room temperature. This was followed by the addition of TEA (2.73 mL, 19.56 mmol, 6.00 equiv) dropwise with stirring at −70° C. The resulting solution was stirred for 3 h from −70° C. to room temperature. The resulting solution was diluted with dry cyclohexane. The solids were filtered out and then concentrated under reduced pressure. The residue was purified on a silica gel column with hexane: EA (10:1-2:1). This resulted in 400 mg (36%) of dipropyl 2,2'-((chlorophosphoryl)bis(azanediyl))(2S,2'S)-dipropionate as yellow oil. $^{31}$P-NMR (CDCl$_3$, 400 MHz): δ 16.2.

Step C

To a solution of (3aR,4R,6S,6aS)-4-(4-aminopyrrolo[2,1-f][1,2,4]triazin-7-yl)-6-fluoro-6-(hydroxymethyl)-2-methoxytetrahydrofuro[3,4-d][1,3]dioxole-4-carbonitrile (product from Step C of Example 5) (27 mg, 0.08 mmol) in THF (1.5 mL) under inert atmosphere was added t-BuMgCl (1 M in THF, 0.23 mL, 3.00 equiv) dropwise with stirring at −78° C. The resulting solution was stirred for 30 min at room temperature. To this was added a solution of dipropyl 2,2'-((chlorophosphoryl)bis(azanediyl))(2S,2'S)-dipropionate (131.8 mg, 0.38 mmol, 5.00 equiv) in tetrahydrofuran (0.2 mL) dropwise with stirring at −78° C. The resulting solution was stirred for 1 h at room temperature. The reaction was then quenched with aq. NH$_4$Cl (50 ml), extracted with ethyl acetate (50 ml×2) and combined organic extracts dried over anhydrous sodium sulfate, filtered and concentrated under reduced pressure. The residue was purified on a silica gel column with dichloromethane/methanol (10:1). This resulted in 26 mg (51%) of compound 10A as yellow oil. MS m/z [M+H]$^+$ (ESI): 658. Compound 10A has the following structure:

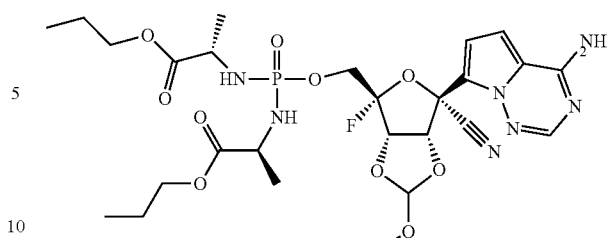

Compound 10 was prepared as follows: A solution of Compound 10A (110 mg, 0.17 mmol, 1.00 equiv) in 80% HCOOH/H$_2$O (8 mL) was stirred for 15 h at room temperature. The resulting mixture was concentrated under reduced pressure. The crude product was purified by RP-HPLC (XBridge Prep OBD C18 Column, 19×250 mm, 5 um; mobile phase, A: 0.1% aq. HCOOH, B: 0.1% HCOOH in ACN; gradient 27% to 42.% B in 8 min; detector, UV 220 nm). This resulted in 31.7 mg (31%) of Compound 10 as a light yellow solid. MS m/z [M+H]$^+$ (ESI): 616. $^1$H-NMR (CD$_3$OD): δ 7.93 (s, 1H), 7.01 (d, J=4.6 Hz, 1H), 6.93 (d, J=4.6 Hz, 1H), 4.83 (d, J=6.6 Hz, 1H), 4.61 (dd, J=20.3, 6.6 Hz, 1H), 4.34-4.17 (m, 2H), 4.13-3.97 (m, 4H), 3.94-3.80 (m, 2H), 1.75-1.59 (m, 4H), 1.33-1.27 (m, 6H), 0.95-0.89 (m, 6H). $^{19}$F-NMR (CD$_3$OD): δ−124.38 $^{31}$P-NMR (CD$_3$OD): δ 13.675.

Example 11

Compound 11: Isopropyl (((((2R,3 S,4R,5R)-5-(4-aminopyrrolo[2,1-f][1,2,4]triazin-7-yl)-2-azido-5-cyano-3,4-dihydroxytetrahydrofuran-2-yl)methoxy)(phenoxy)phosphoryl)-D-alaninate

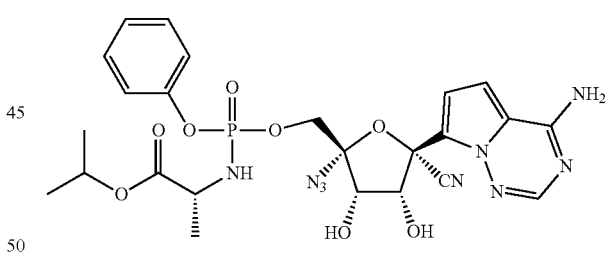

A mixture of nucleoside (2R,3R,4S,5R)-2-(4-aminopyrrolo[2,1-f][1,2,4]triazin-7-yl)-5-azido-3,4-dihydroxy-5-(hydroxymethyl)tetrahydrofuran-2-carbonitrile (Compound 2, 10 mg, 0.03 mmol), NMI (30 μL, 0.36 mmol) and isopropyl (chloro(phenoxy)phosphoryl)-L-alaninate (28 mg, 0.1 mmol) in acetonitrile (0.4 mL) was stirred at r. t. under Ar for 1 h. The mixture was concentrated and residue partitioned between CH$_2$Cl$_2$ and 1N citric acid. Organic layer was washed with water, sat. aq. NaHCO$_3$, and brine. Combined aqueous washings were reextracted with CH$_2$Cl$_2$. Combined organic extracts were dried (Na$_2$SO$_4$), evaporated and purified by flash chromatography on silica gel with a gradient of 3-12% MeOH in DCM to yield 4 mg (22%) of the title compound. MS m/z: 602.1 [M+1]+$^-$. $^{31}$P-NMR (CD$_3$OD): δ 3.21, 3.18 (2s).

Example 12

Compound 12: ((2S,3S,4R,5R)-5-(4-Aminopyrrolo[2,1-f][1,2,4]triazin-7-yl)-5-cyano-2-fluoro-3,4-dihydroxytetrahydrofuran-2-yl)methyl tetrahydrogen triphosphate

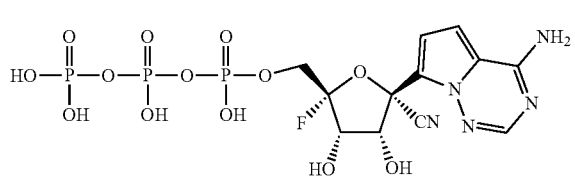

Dry (2R,3R,4S,5S)-2-(4-Aminopyrrolo[2,1-f][1,2,4]triazin-7-yl)-5-fluoro-3,4-dihydroxy-5-(hydroxymethyl)tetrahydrofuran-2-carbonitrile (Compound 1, 0.05 mmol) was dissolved in dry PO(OMe)$_3$ (0.7 mL). N-methylimidazole (0.009 mL, 0.11 mmol) was added followed by POCl$_3$ (0.009 mL, 0.11 mmol), and the mixture was kept at rt for 20-40 mins. The reaction was controlled by LCMS and monitored by the appearance of corresponding nucleoside 5'-monophosphate. After completion of the reaction, tetrabutylammonium salt of pyrophosphate (150 mg) was added, followed by DMF (0.5 mL) to get a homogeneous solution. After 1.5 hours at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH 7.5). Triphosphate was eluted at 75-80% B. Corresponding fractions were concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer to provide the title compound (see Table 5).

Example 13

Compound 13: ((2R,3S,4R,5R)-5-(4-Aminopyrrolo[2,1-f][1,2,4]triazin-7-yl)-5-cyano-2-(fluoromethyl)-3,4-dihydroxytetrahydrofuran-2-yl)methyl tetrahydrogen triphosphate

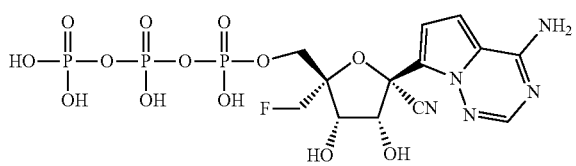

The title compound was prepared in the manner described in Example 12 using (2R,3R,4S,5R)-2-(4-aminopyrrolo[2,1-f][1,2,4]triazin-7-yl)-5-(fluoromethyl)-3,4-dihydroxy-5-(hydroxymethyl)tetrahydrofuran-2-carbonitrile (Compound 3) as a starting material (see Table 5).

Example 14

Compound 14: ((2R,3S,4R,5R)-5-(4-Aminopyrrolo[2,1-f][1,2,4]triazin-7-yl)-2-azido-5-cyano-3,4-dihydroxytetrahydrofuran-2-yl)methyl tetrahydrogen triphosphate

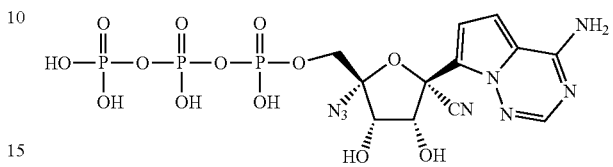

The title compound was prepared in the manner described in Example 12 using (2R,3R,4S,5R)-2-(4-aminopyrrolo[2,1-f][1,2,4]triazin-7-yl)-5-azido-3,4-dihydroxy-5-(Hydroxymethyl)tetrahydrofuran-2-carbonitrile (Compound 2) as a starting material (see Table 5).

Example 15

Compound 15: (2R,3R,4S,5R)-2-(4-Aminopyrrolo[2,1-f][1,2,4]triazin-7-yl)-5-(chloromethyl)-3,4-dihydroxy-5-(hydroxymethyl)tetrahydrofuran-2-carbonitrile

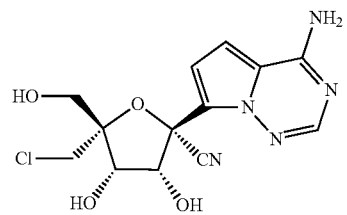 [SMILES: N#C[C@@]1(c2ccc3c(N)ncnn23)O[C@@](CO)(CCl)[C@@H](O)[C@H]1O]

The title compound may be prepared in a manner analogous to Compound 3, using (3R,4S,5R)-5-(chloromethyl)-3,4-dihydroxy-5-(hydroxymethyl)dihydrofuran-2 (3H)-one instead of (3R,4S,5R)-3,4-bis(benzyloxy)-5-((benzyloxy)methyl)-5-(fluoromethyl)dihydrofuran-2(3H)-one (Intermediate 2) in Step A.

TABLE 5

| Compound | MS (M−1) | P(γ) | P(β) | P(α) |
| --- | --- | --- | --- | --- |
| 12 | 548.3 | −10.91 (d) | −22.27(t) | −12.22 (d) |
| 13 | 561.8 | −10.98 (d) | −23.43(t) | −11.96 (d) |
| 14 | 571.2 | −11.00 (d) | −22.40(t) | −12.45 (d) |

Example A

Dengue Antiviral Assay (DENV)

The Dengue virus type 2 strain New Guniea C (NG-C) and the Dengue virus type 4 strain H241 were purchased from ATCC (Manassas, Va.; item numbers VR-1584 and VR-1490, respectively). 24 hours prior to dosing, Huh-7.5 cells were plated in 96 well plates at a density of $1.5 \times 10^5$/ml in DMEM medium supplemented with 10% fetal bovine serum, 1% HEPES buffer, 1% Penicillin/Streptomycin and 1% non-essential amino acids (all Mediatech, Manassas, Va.). At the day of infection, serially diluted compounds were added to cells and incubated for 4 hours. After the end of the 4 hour pre-incubation period, cells were infected with either Dengue virus type 2 NG-C or Dengue virus type 4 H241. The virus inoculum was selected to cause 80-90% cytopathic effect in five to six days. Infected cells were incubated for five (NG-C) to six (H241) days at 37° C., 5% $CO_2$. To develop the assay, 100 µl media was replaced with 100 µl CellTiter-Glo® reagent (Promega, Madison, Wis.), and incubated for 10 min at room temperature. Luminescence was measured on a Victor X3 multi-label plate reader. Potential compound cytotoxicity was determined using uninfected parallel cultures. Compounds of Formula (I) showed activity in this DENV assay as indicated by the $EC_{50}$ values provided in Table 6. Compounds of Formula (I) also showed relatively low values of toxicity in the assay as indicated by the $CC_{50}$ values provided in Table 6.

Example B

Rhinovirus antiviral assay (HRV1B)

HeLa-OHIO cells (Sigma-Aldrich, St. Louis, Mo.) were plated in 96 well plates at a density of $1.5 \times 10^5$ cells per well in assay media (MEM without phenol red or L-glutamine, supplemented with 1% FBS, 1% penicillin/streptomycin, 2 mM GlutaGro, and 1×MEM nonessential amino acids, all from Cellgro, Manassas, Va.). Assay setup took place after allowing cells to adhere for 24 h. Compounds dissolved in DMSO were serially diluted in assay media to 2× final concentration. Media was aspirated from the cells, and 100 µl media with compound was added in triplicate. Human rhinovirus 1B (ATCC, Manassas, Va.) was diluted in assay media, and 100 µL was added to cells and compound. The virus inoculum was selected to cause 80-90% cytopathic effect in 4 d. Infected cells were incubated for 4 d at 33° C., 5% $CO_2$. To develop the assay, 100 µL media was replaced with 100 µL CellTiter-Glo® reagent (Promega, Madison, Wis.), and incubated for 10 mins at RT. Luminescence was measured on a Victor X3 multi-label plate reader. Compounds of Formula (I) showed activity in this HRV1B assay as indicated by the $EC_{50}$ values provided in Table 6. Compounds of Formula (I) also showed relatively low values of toxicity in the assay as indicated by the $CC_{50}$ values provided in Table 6.

Example C

RSV Antiviral Assay (RSV)

The HeLa-derived cells containing the stable RSV replicon were cultured in DMEM containing 4500 mg/L D-glucose, L-glutamine, and 110 mg/L sodium pyruvate. The medium was further supplemented with 10% (v/v) FBS (Mediatech), 1% (v/v) penicillin/streptomycin (Mediatech), and 10 µg/mL of Blasticidin (BSD) (Invivogen). Cells were maintained at 37° C. in a humidified 5% $CO_2$ atmosphere. On the first day, 5000 RSV replicon cells per well were plated in a 96-well plate. On the following day, compounds to be tested were solubilized in 100% DMSO to 100×the desired final testing concentration. Cells were incubated with compounds for 7 days at 37° C. in a 5% $CO_2$ atmosphere before measurement of the luciferase readout. Cell viability ($CC_{50}$) was measured with a CellTiter-Glo cell proliferation assay (Promega). Compounds of Formula (I) showed activity in this RSV assay as indicated by the $EC_{50}$ values provided in Table 6. Compounds of Formula (I) also showed relatively low values of toxicity in the assay as indicated by the $CC_{50}$ values provided in Table 6.

Example D

Ebola Antiviral Assay (EBOV)

HEp-2 cells were plated in 96-well plates at the density of 40,000 cells/well. On the next day, modified vaccinia virus Ankara-T7 (MVA-T7) at the multiplicity of infection of 1 was added to provide T7 RNA polymerase. After 2 hours of viral transduction, each well was transfected with Lipofectamine2000 (Thermo Fisher) with 0.01 g mixture of 6 plasmids including Ebola minigenome, plasmids encoding Ebola L, NP, VP-35, VP-30 proteins. After 48 hours of further incubation, cells were lysed with RIPA buffer (Pierce), transferred to a black 96-well plate and the fluorescence was read at 0.1 sec/well at ex485 nm, emission 535 nm on a Victor plate reader. Sigmoidal dose-response curves used to generate 50% inhibitory or effective concentrations were analyzed by nonlinear regression using the four-parameter logistic equation (GraphPad Prism). Compounds of Formula (I) showed activity in this EBOV assay as indicated by the $EC_{50}$ values provided in Table 6. Compounds of Formula (I) also showed relatively low values of toxicity in the assay as indicated by the $CC_{50}$ values provided in Table 6.

Example E

Coronavirus Antiviral Assay

The human β-coronavirus strain OC43 was purchased from ATCC (Manassas, Va.; item numbers VR-1558 and VR-740, respectively). 24 hours prior to dosing, HeLa human cervix epithelial cells (ATCC, CCL-2) or MRC-5 human lung fibroblast (ATCC, CCL-171) were plated in 96 well plates at a density of $1.5 \times 10^5$/ml in DMEM medium supplemented with 10% fetal bovine serum, 1% HEPES buffer, 1% Penicillin/Streptomycin and 1% non-essential amino acids (all Mediatech, Manassas, Va.). At the day of infection, serially diluted compounds were added to cells and incubated for 4 hours. After the end of the 4 hour pre-incubation period, cells were infected with either coronavirus strain OC43 or 229E. The virus inoculum was selected to cause 80-90% cytopathic effect. Infected cells were incubated for five days at 37° C., 5% $CO_2$. To develop the assay, 100 µl media was replaced with 100 µl CellTiter-Glo® reagent (Promega, Madison, Wis.), and incubated for 10 min at room temperature. Luminescence was measured on a Victor X3 multi-label plate reader. Potential compound cytotoxicity was determined using uninfected parallel cultures. Compounds of Formula (I) showed activity in this assay against the human β-coronavirus strain OC43 as indicated by the $EC_{50}$ values provided in Table 6. Compounds of Formula (I) also showed relatively low values of toxicity in the assay as indicated by the $CC_{50}$ values provided in Table 6.

TABLE 6

| | EBOV | | HRV 1B | | OC43CoV | | DENV | | RSV | |
|---|---|---|---|---|---|---|---|---|---|---|
| No. | EC50 (uM) | CC50 (uM) | EC50 (uM) | CC50 (uM) | EC50 (uM) | CC50 (uM) | EC50 (uM) | CC50 (uM) | EC50 (uM) | CC50 (uM) |
| C1 | 0.8 | 51 | 0.12 | 6 | 0.065 | 69 | 0.13 | 22 | 0.02 | 3 |
| 5 | | | | | 25.3 | >100 | 7.37 | >100 | 2.74 | >100 |
| 6 | 2.5 | >100 | 4.1 | >100 | 1.7 | >100 | 0.25, 0.33 | 78, 69 | 0.02 | 43 |
| 7 | 0.2 | 14 | 0.15 | 12.4 | 0.056 | 13 | 0.0014 | 15, 21 | 0.03 | 21 |
| 8 | 0.5, 0.8 | >100 | 1.3, 0.4 | 64 | 0.1 | >50 | 0.11, 0.14 | >100, 25 | 0.03, 0.026 | 30, 7.1 |
| 9 | 0.25 | ~50 | 0.13 | 33 | 0.025 | 34 | 0.07 | 12 | 0.018 | 8.1 |
| 10 | | | 3.1 | >100 | 2.3 | >50 | | | 0.17 | >100 |
| 11 | | | >100 | 59 | >50 | >50 | | | 1.3 | 13.6 |

Compound No. "C1" is a comparison compound having the following structure:

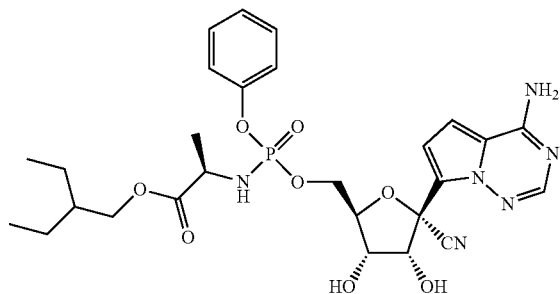

(C1)

Example F

Dengue Polymerase Assay (DENVpol)

The enzyme activity of dengue virus NS5 polymerase domain (DENVpol, serotype 2, New Guinea C strain) was measured as an incorporation of tritiated NMP into acid-insoluble RNA products. DENVpol assay reactions contained 100 nM recombinant enzyme, 50 nM heteropolymeric RNA, about 0.5 µCi tritiated NTP, 0.33 µM of competing cold NTP, 40 mM HEPES (pH 7.5), 3 mM dithiothreitol, and 2 mM MgCl$_2$. Standard reactions were incubated for 3 hours at 30° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radiolabeled RNA products were detected according to standard procedures with a Trilux Topcount scintillation counter. The compound concentration at which the enzyme-catalyzed rate was reduced by 50% (IC$_{50}$) was calculated by fitting the data to a non-linear regression (sigmoidal). The IC$_{50}$ values were derived from the mean of several independent experiments and are shown in Table 7. Compounds of Formula (I) showed activity in this assay.

Example G

Rhinovirus Polymerase (HRV16pol) and HCV Polymerase (HCVpol) Assays

The enzyme activity of hepatitis C virus RNA polymerase (HCVpol) and human rhinovirus 16 RNA polymerase (HRV16pol) is measured as an incorporation of tritiated NMP into acid-insoluble RNA products. HCVpol and HRV16pol assay reactions contain 30-100 nM recombinant enzyme, 50-500 nM heteropolymeric RNA, 0.5 µCi tritiated NTP, 0.1-1 µM of other NTPs, in a standard reaction buffer containing MgCl$_2$. Enzymatic reactions are incubated for 2.5 hours at 30° C., in the presence of increasing concentration of inhibitor. At the end of the reaction, the total RNA is precipitated with 10% TCA, and acid-insoluble RNA products are filtered on a size exclusion 96-well plate. After washing of the plate, scintillation liquid is added and radiolabeled RNA products are detected according to standard procedures with a Trilux Microbeta scintillation counter. The compound concentration at which the enzyme-catalyzed rate is reduced by 50% (IC$_{50}$) is calculated by fitting the data to a non-linear regression (sigmoidal). Compounds of Formula (I) showed activity in these assays.

Example H

RSV Polymerase Assay (RSVpol)

Standard RSV polymerase assays were conducted in the presence of 3 µL extract of RSV-infected cells in a reaction buffer containing 50 mM tris-acetate pH 8, 120 mM K-acetate, 4.5 mM MgCl$_2$, 5% glycerol, 2 mM EDTA, 50 µg/ml BSA, and 3 mM DTT. Varying concentration of NTPs were used to initiate RNA synthesis for 120 minutes at 30 degrees, and radioactive 33P GTP (15 µCi) was used as tracer. The reaction was stopped by adding 50 mM EDTA, and RNA samples were purified through G-50 size exclusion spin columns and phenol-chloroform extraction. The radio-labeled RNA products were resolved by electrophoresis on a 6% polyacrylamide TBE gel, and visualized and quantitated after being exposed on a phosphorImager screen. Polymerase inhibition experiments (IC50s) were conducted the same way in the presence of increasing concentration of NTP analogs. Compounds of Formula (I) showed activity in these assays.

Compound No. "C2" is a comparison compound having the following structure:

TABLE 7

| No. | HRV16pol IC$_{50}$ (uM) | HCVpol IC$_{50}$ (uM) | DENVpol IC$_{50}$ (uM) | RSVpol IC$_{50}$ (uM) |
|---|---|---|---|---|
| C2 | 0.27 | 1 | 3.6 | 0.12 |
| 12 | 0.13 | 0.4 | 1.1 | 0.03 |
| 13 | 0.21 | >10 | >10 | >10 |
| 14 | 0.04 | 0.3 | 1.1 | 0.03 |

(C2)

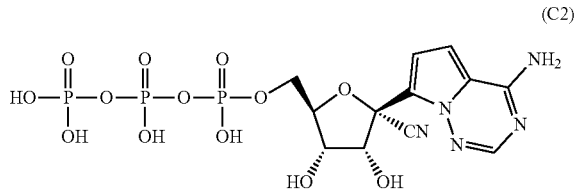 [SMILES: N#C[C@@]1(c2ccc3c(N)ncnn23)O[C@H](COP(=O)(O)OP(=O)(O)OP(=O)(O)O)[C@@H](O)[C@H]1O]

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I) having the structure:

(I)

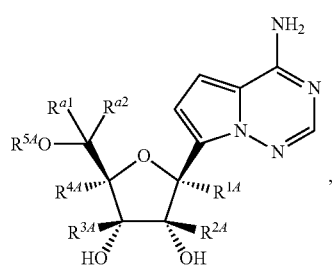

or a pharmaceutically acceptable salt thereof, wherein:

$R^{1A}$ is selected from the group consisting of fluoro, cyano, azido, an unsubstituted $C_{2-4}$ alkenyl, an unsubstituted $C_{2-4}$ alkynyl, an unsubstituted $C_{1-4}$ alkoxy, an unsubstituted $C_{1-4}$ alkyl and a substituted $C_{1-4}$ alkyl, wherein said substituted $C_{1-4}$ alkyl is substituted with one or more substituents selected from fluoro and chloro;

$R^{4A}$ is selected from the group consisting of fluoro, cyano, azido, an unsubstituted $C_{2-4}$ alkenyl, an unsubstituted $C_{2-4}$ alkynyl, an unsubstituted $C_{1-4}$ alkoxy, an unsubstituted $C_{1-4}$ alkyl and a substituted $C_{1-4}$ alkyl, wherein said substituted $C_{1-4}$ alkyl is substituted with one or more substituents selected from fluoro and chloro;

$R^{2A}$, $R^{3A}$, $R^{a1}$ and $R^{a2}$ are each independently hydrogen or deuterium;

$R^{5A}$ is selected from the group consisting of hydrogen, an optionally substituted acyl, an optionally substituted O-linked amino acid,

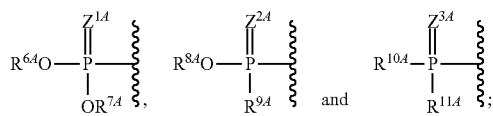

$R^{6A}$, $R^{7A}$ and $R^{8A}$ are independently selected from the group consisting of absent, hydrogen, an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *($cR^{15A}R^{16A})_p$-O-$C_{1-24}$ alkyl, an optionally substituted *-$(CR^{17A}R^{18A})_q$-O-$C_{1-24}$ alkenyl,

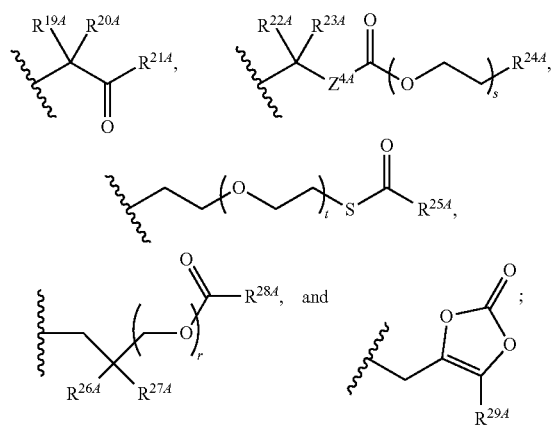

or $R^{6A}$ is

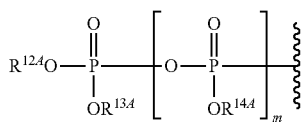

and $R^{7A}$ is absent or hydrogen; or $R^{6A}$ and $R^{7A}$ and R are taken together to form a moiety selected from the group consisting of an optionally substituted

and an optionally substituted

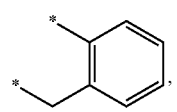

wherein the oxygens connected to $R^{6A}$ and $R^{7A}$, the phosphorus and the moiety form a six-membered to ten-membered ring system;

$R^{9A}$ is independently selected from the group consisting of an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative;

$R^{10A}$ and $R^{11A}$ are independently an optionally substituted N-linked amino acid or an optionally substituted N-linked amino acid ester derivative;

$R^{12A}$, $R^{13A}$ and $R^{14A}$ are independently absent or hydrogen;

each $R^{15A}$, each $R^{16A}$, each $R^{17A}$ and each $R^{18A}$ are independently hydrogen, an optionally substituted $C_{1-24}$ alkyl or alkoxy;

$R^{19A}$, $R^{20A}$, $R^{22A}$ and $R^{23A}$ are independently selected from the group consisting of hydrogen, an optionally substituted $C_{1-24}$ alkyl and an optionally substituted aryl;

$R^{21A}$ and $R^{24A}$ are independently selected from the group consisting of hydrogen, an optionally substituted $C_{1-24}$ alkyl, an optionally substituted aryl, an optionally substituted —O—$C_{1-24}$ alkyl, an optionally substituted —O-aryl an optionally substituted —O-heteroaryl, an optionally substituted —O-monocyclic heterocyclyl and

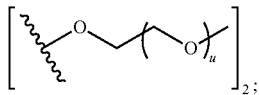

$R^{25A}$ and $R^{29A}$ are independently selected from the group consisting of hydrogen, an optionally substituted $C_{1-24}$ alkyl and an optionally substituted aryl;

$R^{26A}$ and $R^{27A}$ are independently or an optionally substituted substituent selected from the group consisting of $C_{2-8}$ organylcarbonyl, $C_{2-8}$ alkoxycarbonyl and $C_{2-8}$ organylaminocarbonyl;

$R^{28A}$ is selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R^{30A}$ and $R^{31A}$ are independently selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

m and t are independently 0 or 1;
p and q are independently selected from the group consisting of 1, 2 and 3;
r is 1 or 2;
s is 0, 1, 2 or 3;
u is 1 or 2; and
$Z^{1A}$, $Z^{2A}$, $Z^{3A}$ and $Z^{4A}$ are independently O or S.

2. The compound of claim 1, or a pharmaceutically acceptable salt thereof, wherein $R^{1A}$ is cyano.

3. The compound of claim 1, or a pharmaceutically acceptable salt thereof, wherein $R^{4A}$ is selected from the group consisting of fluoro, cyano, azido, a substituted $C_{1-4}$ alkyl and an unsubstituted $C_{1-4}$ alkyl.

4. The compound of claim 3, or a pharmaceutically acceptable salt thereof, wherein the substituted $C_{1-4}$ alkyl is selected from the group consisting of —$(CH_2)_{1-4}Cl$, —$(CH_2)_{1-4}F$ and —$CHF_2$.

5. The compound of claim 4, or a pharmaceutically acceptable salt thereof, wherein the substituted $C_{1-4}$ alkyl is selected from the group consisting of chloromethyl, fluoromethyl and difluoromethyl.

6. The compound of claim 1, or a pharmaceutically acceptable salt thereof, wherein $R^{5A}$ is hydrogen.

7. The compound of claim 1, or a pharmaceutically acceptable salt thereof, wherein $R^{5A}$ is

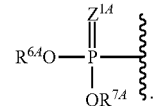

8. The compound of claim 7, or a pharmaceutically acceptable salt thereof, wherein $R^{6A}$ and $R^{7A}$ are hydrogen.

9. The compound of claim 7, or a pharmaceutically acceptable salt thereof, wherein $R^{6A}$ is

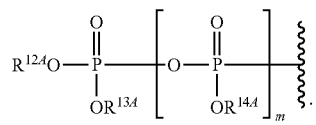

10. The compound of claim 9, wherein $R^{12A}$, or a pharmaceutically acceptable salt thereof, $R^{13A}$ and $R^{14A}$ are hydrogen.

11. The compound of claim 7, or a pharmaceutically acceptable salt thereof, wherein $Z^{1A}$ is O.

12. The compound of claim 1, or a pharmaceutically acceptable salt thereof, wherein $R^{5A}$ is

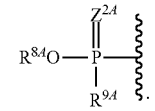

13. The compound of claim 12, or a pharmaceutically acceptable salt thereof, wherein $R^{8A}$ is an optionally substituted aryl; and $R^{9A}$ is an optionally substituted N-linked amino acid or an optionally substituted N-linked amino acid ester derivative.

14. The compound of claim 12, or a pharmaceutically acceptable salt thereof, wherein $Z^{2A}$ is O.

15. The compound of claim 1, wherein the compound of Formula (I) is selected from the group consisting of:

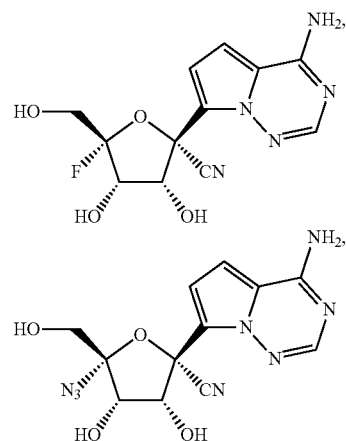

101

-continued

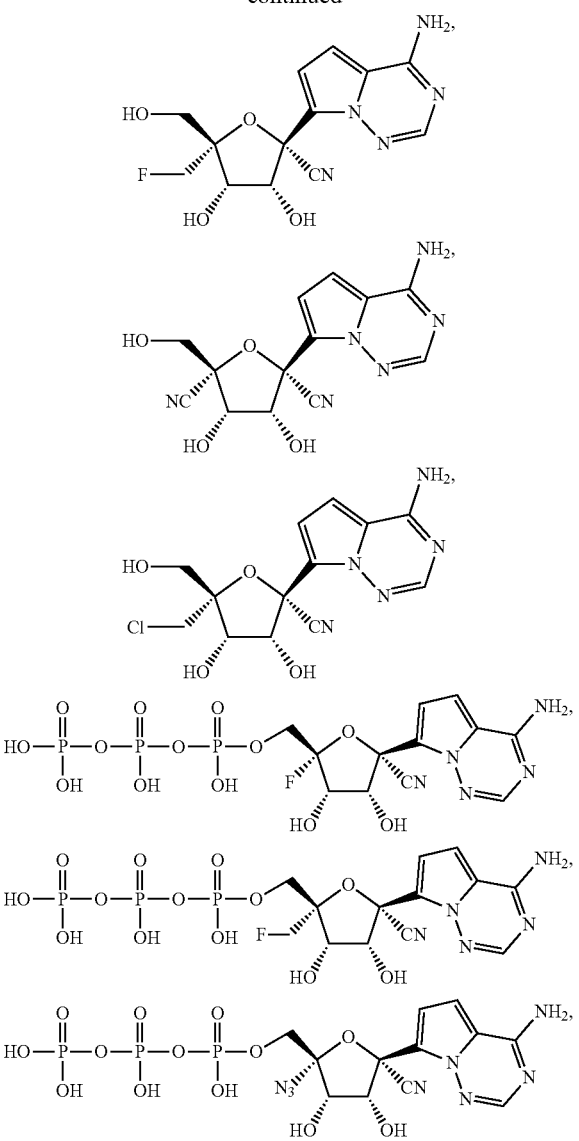

102

-continued

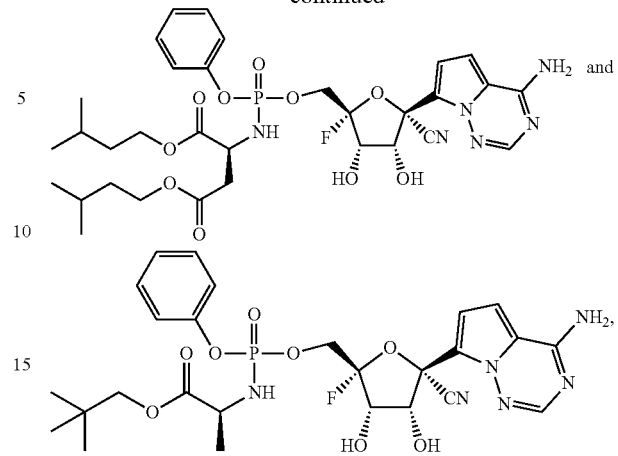

or a pharmaceutically acceptable salt of any of the foregoing.

16. A pharmaceutical composition comprising an effective amount of a compound of claim 1, or a pharmaceutically acceptable salt thereof, and a pharmaceutically acceptable carrier, diluent, excipient, or combination thereof.

17. A method of ameliorating or treating a viral infection comprising administering an effective amount of a compound of claim 1, or a pharmaceutically acceptable salt thereof, or the pharmaceutical composition of claim 16, to a subject suffering from the viral infection, wherein the viral infection is a Picornaviridae, Flaviviridae, Filoviridae, Pneumoviridae, or Coronaviridae viral infection.

18. The method of claim 17, wherein the Picornaviridae viral infection is a Rhinovirus infection; the Flaviviridae viral infection is a Dengue virus infection or a Hepacivirus infection; the Filoviridae viral infection is an Ebolavirus infection; the Pneumoviridae viral infection is a human respiratory syncytial virus (HRSV) infection; the Pneumoviridae viral infection is a human respiratory syncytial virus (HRSV) infection; and the Coronaviridae viral infection is a human α-coronavirus viral infection or a human β-coronavirus viral infection.

19. The method of claim 17, wherein the compound is selected from the group consisting of:

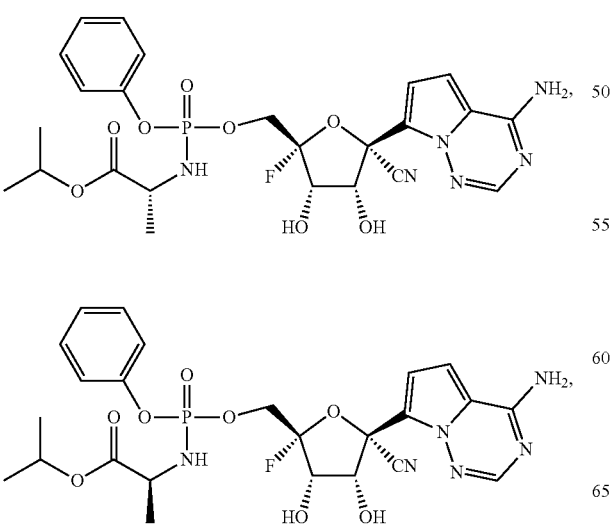

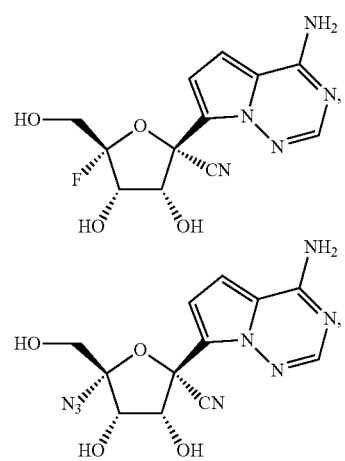

-continued
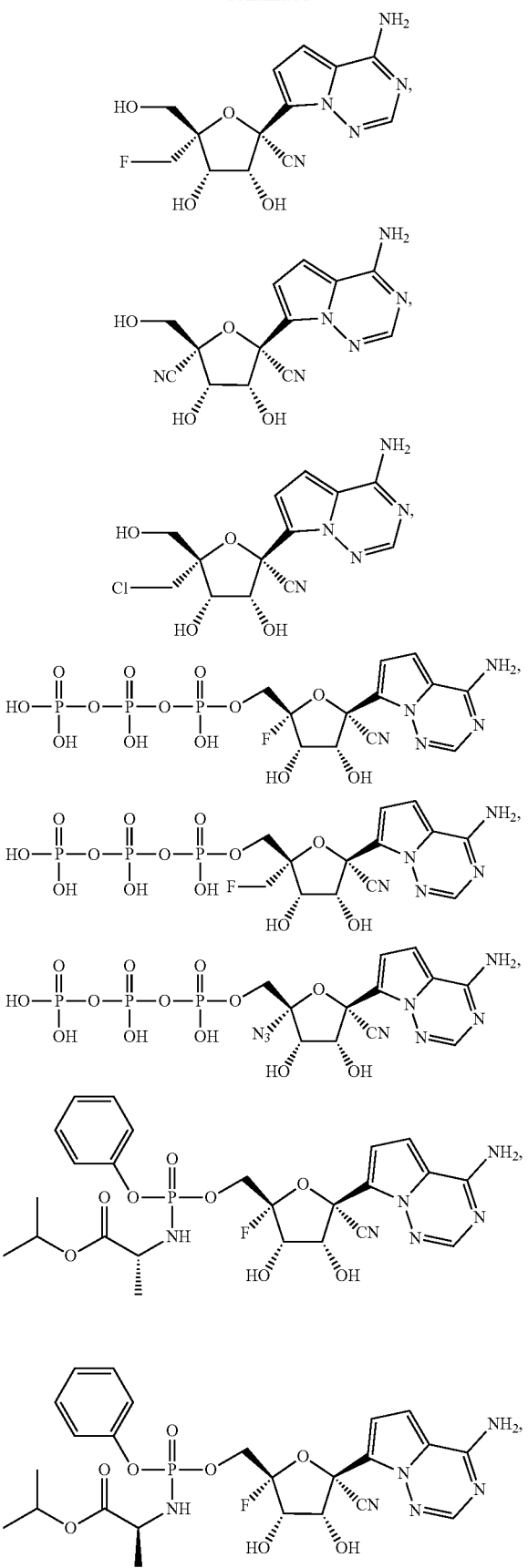
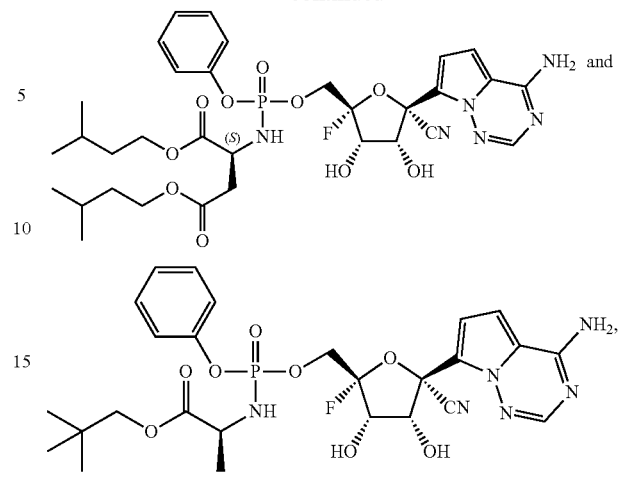
or a pharmaceutically acceptable salt of any of the foregoing.
20. A compound of Formula (Ia2) having the structure:
or a pharmaceutically acceptable salt thereof,
wherein:
(Ia2)
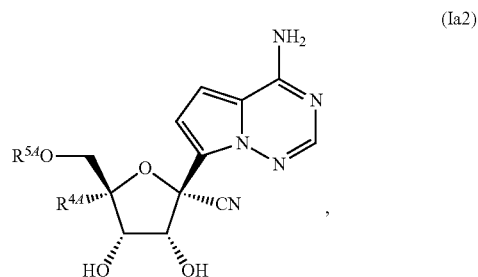
$R^{4A}$ is selected from the group consisting of: fluoro, cyano, azido and $C_{1-4}$ alkyl substituted with one or more substituents selected from fluoro and chloro;
$R^{5A}$ is hydrogen,
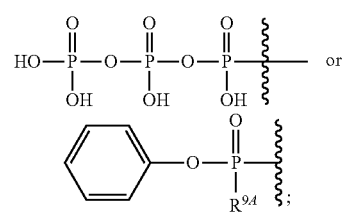
$R^{9A}$ is
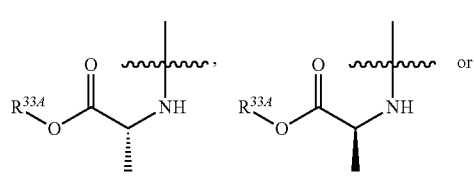

-continued
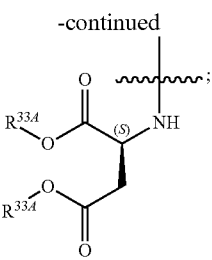
and
$R^{33A}$ is $C_{1-6}$ alkyl.
* * * * *